United States Patent [19]
Popper et al.

[11] 3,932,388
[45] Jan. 13, 1976

[54] -AZIDO-4,6-PREGNADIENO(3,2-C)PYRAZOLES, PROCESSES FOR THEIR PREPARATION AND INTERMEDIATES USEFUL THEREIN

[75] Inventors: Thomas L. Popper, West Caldwell; Richard W. Draper, East Orange; Elliot L. Shapiro, Cedar Grove; Arthur S. Watnick, South Orange, all of N.J.

[73] Assignee: Schering Corporation, Kenilworth, N.J.

[22] Filed: Apr. 22, 1974

[21] Appl. No.: 462,687

[52] U.S. Cl.... 260/239.55 R; 260/349; 260/397.45; 260/239.55 D; 424/241
[51] Int. Cl.² .......................................... C07J 1/00
[58] Field of Search .......................... 260/239.5, 349

[56] References Cited
UNITED STATES PATENTS

| | | | |
|---|---|---|---|
| 3,376,292 | 4/1968 | Beard et al. ...................... | 260/239.5 |
| 3,475,417 | 10/1969 | Nelson .............................. | 260/239.5 |
| 3,475,418 | 10/1969 | Hirschmann et al. ............. | 260/239.5 |
| 3,784,603 | 1/1974 | Shapiro et al. ................... | 260/397.45 |

*Primary Examiner*—Elbert L. Roberts
*Attorney, Agent, or Firm*—Mary S. King

[57] ABSTRACT

Steroidal 6-azido-4,6-pregnadieno[3,2-c]pyrazoles having glucocorticoid activity are prepared by treating a 6-unsubstituted-4,6-pregnadieno[3,2-c]pyrazole with a halogen azide followed by treatment of the thereby formed 6-azido-7-halogeno-6,7-dihydro-4-pregnene[3,2-c]pyrazole with a dehydrohalogenating agent. Other methods of preparing these compounds are described, including the process of treating a 6-azido-17α,20; 20,21-bismethylenedioxy-4,6-pregnadiene-3-one with an alkyl formate in the presence of base followed by treatment of the resulting 2-hydroxymethylene derivative with a hydrazine or, alternatively, by converting said 2-hydroxymethylene to a 2-alkoxymethylene derivative followed by treatment thereof with a hydrazine.

Preferred compounds include 6-azido-11β,17α,21-trihydroxy-20-keto-4,6-pregnadieno[3,2-c]pyrazoles, particularly 2'-phenyl-9α-fluoro(and 9α-chloro)-16-methyl-derivatives thereof which possess potent anti-inflammatory activity. Of interest is 2'-phenyl-6-azido-9α-fluoro-11β,17α,21-trihydroxy-16α-methyl-20-keto-4,6-pregnadieno[3,2-c]pyrazole.

26 Claims, No Drawings

-AZIDO-4,6-PREGNADIENO(3,2-C)PYRAZOLES, PROCESSES FOR THEIR PREPARATION AND INTERMEDIATES USEFUL THEREIN

FIELD OF INVENTION

This invention relates to novel steroidal compositions-of-matter, to methods for their manufacture and to novel intermediates useful therein.

More specifically, this invention relates to compositions-of-matter having glucocorticoid activity which may be classified as 6-azido-20-keto-4,6-pregnadieno [3,2-c] pyrazoles, to methods for their manufacture, and to novel intermediates useful therein, including 6-azido-7-halogeno-6,7-dihydro-20-keto-4-pregneno [3,2-c] pyrazoles.

In particular, this invention relates to 6-azido-20-keto-4,6-pregnadieno [3,2-c] pyrazoles unsubstituted at C-21 or having a 21-fluoro-, 21-chloro, 21-hydroxy or a 21-acyloxy group, said pregnadienopyrazoles exhibiting anti-inflammatory activity and in the case of the 21-unsubstituted-, 21-chloro-and 21-fluoro derivatives, also exhibiting progestational activity. This invention also relates to methods for the manufacture of the foregoing 4,6-pregnadieno [3,2-c] pyrazoles and to novel intermediates useful therein, including 21-unsubstituted, 21-fluoro-, 21-chloro-, 21-hydroxy-, and 21-acyloxy-6-azido-7-halogeno-6,7-dihydro-20-keto-4-pregneno [3,2-c] pyrazoles.

Our invention also includes the method of using said 6-azido-17α-hydroxy-20-keto-21-unsubstituted-(or 21-fluoro-, 21-chloro-, 21-hydroxy-, or 21-acyloxy-)-4,6-pregnadieno [3,2-c] pyrazoles as anti-inflammatory agents; the method of using 6-azido-17α- lower alkanoyloxy-20-keto-21-unsubstituted (or 21- fluoro- or 21-chloro-)-4,6-pregnadieno[3,2-c]pyrazoles as progestational agents, and to pharmaceutical formulations useful in said methods.

Description of the Prior Art

Known in the art are 6-unsubstituted-20-keto-4,6-pregnadieno[3,2-c]pyrazoles having anti-inflammatory activity and their method of preparation from the corresponding 6-unsubstituted-3-keto-1,2-dihydro-4,6-pregnadiene by treatment with an alkyl formate and thence treatment of the resulting 2-hydroxy-methylene-3-keto-4,6-pregnadiene derivative with a hydrazine.

Also known in the art are 3,20-diketo-6-azido-21-unsubstituted (also 21-chloro and 21-fluoro)-4,6-pregnadienes having progestational activity and 3,20-diketo-6-azido-17α,21-dihydroxy-4,6-pregnadienes and acyloxy derivatives thereof having corticoid activity, and methods for their preparation from the corresponding 6-unsubstituted analogs by epoxidation at C-6,7, followed by cleavage of the resulting 6α,7α-oxido derivative with an alkali metal azide and thence treatment of the 3,20-diketo-6β-azido-7α-hydroxy-4-pregnene thereby formed or a 7α-ester thereof, with concentrated hydrochloric acid in a lower alkanoic acid, or alternatively, treating said 3,20-diketo-6β-azido-7α-acyloxy-4-pregnene with a tetraalkylammonium halide in an aprotic solvent.

By our invention, we have discovered novel 6-azido-20-keto-4,6-pregnadieno[3,2-c]pyrazoles having corticoid activity, and methods for their preparation, such as by treatment of the corresponding 6-unsubstituted-20-keto-4,6-pregnadieno[3,2-c]-pyrazole with a halogen azide followed by dehydrohalogenation of the novel 6-azido-7-halogeno-20-keto-4,6-pregnadieno[3,2-c]-pyrazole thereby formed.

By our invention, we have also discovered that 6-azido-11β,17α,21-trihydroxy-20-keto-4,6-pregnadieno[3,2-c]pyrazole derivatives exhibit enhanced anti-inflammatory activity over that exhibited by the corresponding 6-unsubstituted-4,6-pregnadieno[3,2-c]pyrazole or by the corresponding 3-keto-6-azido-4,6-pregnadieno-des[3,2-c]pyrazole derivative.

GENERAL DESCRIPTION OF THE INVENTION

Composition of Matter Aspect

The invention sought to be patented in one composition-of-matter aspect resides in the concept of a chemical compound exhibiting glucocorticoid activity and having a molecular structure comprising a steroid with a 6-azido-20-keto-4,6-pregnadieno-[3,2-c]pyrazole nucleus unsubstituted at C-21 or having at C-21 a member selected from the group consisting of a halogen of atomic weight less than 40, hydroxy- and acyloxy and preferably also having hydroxyl groups at the 11β- and 17α- positions, and a halogen of atomic weight less than 40 at the 9α-position. Of the foregoing, preferred as anti-inflammatory agents are the 21-hydroxy and 21-acyloxy derivatives, particularly preferred species of this invention being 6-azido-9α-fluoro-11β,17α,21-trihydroxy-16-methyl-20-keto-4,6-pregnadieno[3,2-c]pyrazoles and their 21 esters.

Included among the pharmacologically active 6-azido-20-keto-4,6-pregnadieno[3,2-c]pyrazoles of this invention are compounds of following formula I:

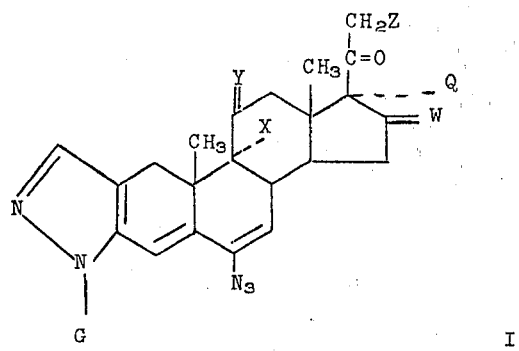

I wherein G is a member selected from the group consisting of hydrogen, lower alkyl, cycloalkyl, aralkyl, aryl and lower hydrocarbon carboxylic acyl;

Q is a member selected from the group consisting of hydroxy, OR wherein R is an acyl radical of a hydrocarbon carboxylic acid having up to 12 carbon atoms, and hydrogen provided W is a member selected from the group consisting of hydrogen and (H, lower alkyl);

W is a member selected from the group consisting of

(H, lower alkyl), (H,α-hydroxy) and (H,α-OR$_1$), wherein R$_1$ is an acyl radical of a hydrocarbon carboxylic acid having up to 12 carbon atoms, =CHT wherein T is a member selected from the group consisting of hydrogen, lower alkyl, fluorine and chlorine and W and Q taken together is 16α,17α-lower alkylidenedioxy;

X is a member selected from the group consisting of hydrogen and halogen having an atomic weight less than 100;

Y is a member selected from the group consisting of

oxygen, (H,βOH), (H,βOCOH), and (H,β-halogen of atomic weight less than 100) providing X is halogen;

Z is a member selected from the group consisting of hydrogen, hydroxy, halogen having an atomic weight up to 40, $OR_2$ wherein $R_2$ is an acyl radical of an acid selected from the group consisting of a hydrocarbon carboxylic acid having up to 12 carbon atoms, phosphoric acid and the mono- and di-alkali and alkaline earth metal salts thereof, and Z together with Q is a member selected from the group consisting of alkylidenedioxy and alkyl orthoalkanoate.

Alkyl groups included within the definition of G and W are preferably lower alkyl, particularly those having up to four carbon atoms such as methyl, ethyl, n-propyl, iso-propyl, n-butyl, sec.-butyl and tert.-butyl, although higher homologs such as pentyl and hexyl fall within the scope of this invention.

Other groups contemplated for the substituent "G" are cycloalkyl groups preferably having up to 8 carbon atoms including cyclopentyl, cyclohexyl, cycloheptyl, cyclooctyl and substituted alkyl groups such as β-hydroxyethyl-; aralkyl groups such as benzyl, α or β-phenethyl, aryl groups derived from any aromatic nucleus including phenyl and substituted phenyl derivatives such as o-, m-, and p-halogenophenyl, particularly p-fluorophenyl-; p-trifluoromethylphenyl-; o-, m-, and p-tolyl; o-, m-, and p-alkoxyphenyl-, o-, m-, and p-nitrophenyl-, 1″-naphthyl-, 2″-pyridyl-, 3″-pyridyl-, 4″-pyridyl-, 4″-pyridyloxide and 2″-pyrimidyl-; and acyl radicals of hydrocarbon carboxylic acids having up to 12 carbon atoms as listed hereinbelow. Of the foregoing substituents included within the definition of G, preferred are phenyl-, p-fluorophenyl-, p-nitrophenyl-, and p-trifluoromethylphenyl.

As used in the specification and claims of this application, the term "acyl" denotes a radical derived from an acid by the removal of the hydroxyl group, e.g. acetyl is the acyl radical of acetic acid, benzenesulfonyl is the acyl radical of benzenesulfonic acid, and benzoyl is the acyl radical of benzoic acid.

The acyl radicals of the compounds of this invention as defined by G, R, $R_1$ and $R_2$ in Formula I hereinabove include those derived from hydrocarbon carboxylic acids having up to 12 carbon atoms which may be saturated, unsaturated, straight chain or branched chain, aliphatic, cyclic, cyclic-aliphatic, aromatic, aryl-aliphatic, or alkyl-aromatic, and may be substituted by hydroxy, alkoxy containing from 1 to 5 carbon atoms or by halogen such as fluorine, chlorine, or bromine. Typical ester groups of the 6-azido-20-keto-4,6-pregnadieno[3,2-c]pyrazoles of our invention are thus derived from hydrocarbon carboxylic acids such as alkanoic acids exemplified by formic, acetic, propionic, trimethylacetic, butyric, iso-butyric, valeric, iso-valeric, caproic, tert.-butylacetic, enanthic, caprylic, capric, cyclopentylpropionic, undecylic, lauric, and adamantanecarboxylic acids; substituted alkanoic acids such as phenoxyacetic, trifluoroacetic, and β-chloropropionic acids; aromatic and substituted aromatic acids including benzoic, toluic, p-chlorobenzoic acids; aryl-alkanoic acids such as phenylacetic, phenylpropionic and isonicotinic acids; unsaturated acids such as acrylic and sorbic acids; and dibasic acids such as succinic, tartaric, phthalic and benzene disulfonic acids.

The term "lower alkanoyloxy" is contemplated as including acid radicals of lower alkanoic acids having preferably up to 8 carbon atoms such as radicals obtained from acetic, propionic, butyric, valeric, caprylic, caproic, tert. -butylacetic acid and the like.

The halogens at C-9 as defined by X in about Formula I are bromine, chlorine, and preferably fluorine. The halogens at C-21 as defined by Z in above Formula I are fluorine and chlorine.

The alkylidene groups contemplated in the compounds of our invention are preferably lower alkylidenes, i.e. hydrocarbon radicals having preferably up to four carbon atoms and having a terminal double bond attached to the steroid nucleus, including radicals such as methylene, ethylidene, n-propylidene, iso-propylidene, n-butylidene, and sec.-butylidene and the like. The 16-lower alkylidene derivatives of this invention (i.e. when W in above Formula I is =CHT) are double bonded to the D ring at C-16. The 16α,17α-alkylidenedioxy derivatives have the alkylidene terminal bonds attached to different oxygen atoms, i.e. to the oxygens at C-16 and C-17 in the case of the 16α,17α-alkylidenedioxy derivatives, and to oxygens at C-17 and C-21 in the case of the 17α,21-alkylidenedioxy derivatives.

The physical embodiments of the 6-azido-20-keto-4,6-pregadieno[3,2-c]pyrazoles of formula I are characterized by being crystalline solids, usually off-white to tan in color, which are insoluble in water (with the exception of alkali metal salts of esters such as the hemisuccinate and phosphate esters thereof) and soluble in most organic solvents, particularly in acetone, dioxane, dimethylformamide and dimethylsulfoxide, although of limited solubility in non-polar solvents such as dialkyl ethers and alkyl hydrocarbons.

The above-defined 6-azido-20-keto-4,6-pregnadieno-[3,2-c]pyrazoles produced in accordance with our invention, particularly those wherein Z is hydroxy, acyloxy, or together with Q is a 17α,21-alkylidenedioxy, exhibit corticoid activity. Of these, the 6-azido-20-keto-21-oxygenated-4,6-pregnadieno[3,2-c]-pyrazoles devoid of oxygen at C-17 and unsubstituted at C-16, particularly those which are also unsubstituted at C-9 and C-11 (i.e. those wherein X and Y are each hydrogen) possess mineralo-corticoid properties and, as such, are useful in the treatment of conditions requiring retention of sodium, e.g. adrenal insufficiency (i.e. Addison's disease) and salt losing syndromes.

The 6-azido-20-keto-21-oxygenated-4,6-pregnadieno-[3,2-c]pyrazoles defined by Formula I which have halogens at C-9 and at C-11 or an oxygen function at C-11 possess glucocorticoid activity and are particularly valuable as anti-inflammatory agents. Of these, preferred are 11,17-bis-oxygenated derivatives, particularly 6-azido-17α,21-dihydroxy-20-keto-4,6-pregnadieno[3,2-c]pyrazoles and esters thereof having an 11β-hydroxyl function, and preferably also having a 2′-phenyl or a 2′-substituted phenyl substituent, which compounds possess enhanced anti-inflammatory activity, particularly valuable compounds being those having 9α-fluoro- and 16-methyl-substituents.

The enhanced anti-inflammatory activity of the preferred compounds of this invention, i.e. such as the aforementioned 2'-phenyl-6-azido-4,6-pregnadieno[3,2-c]pyrazoles oxygenated at C-11, C-17, and C-21-, particularly 9α-fluoro-11β-hydroxy derivatives thereof, are demonstrated by pharmacological tests in animals as set forth in Table I hereinbelow. Thus, for example, 2'-phenyl-6-azido-11β,17α,21-trihydroxy-20-keto-4,6-pregnadieno-[3,2-c]pyrazole 21-acetate, when tested for anti-inflammatory activity by the well-known systemic granuloma pouch assay described by Selye and modified by Robert and Nezamis, exhibits anti-inflammatory activity greater than 18 times that of prednisolone-acetate, thus demonstrating that 2'-phenyl-6-azido-11β,17α,21-trihydroxy-20-keto-4,6-pregnadieno[3,2-c]pyrazole 21-acetate is about 4.5 times more active as an anti-inflammatory agent in the systemic pouch test than the corresponding 6-unsubstituted analog, i.e. 2'-phenyl-11β,17α,21-trihydroxy-20-keto-4,6-pregnadieno [3,2-c]pyrazole 21-acetate, and about 15 times more active than the corresponding despyrazole-3-keto-analog, i.e., 6-azido-4,6-pregnadiene-11β-17α,21-triol-3,20-dione 21-acetate. Similarly, 2'-phenyl-6-azido-9α-fluoro-11β,17α,21trihydroxy-16α-methyl-20-keto-4,6-pregnadieno[3,2-c]pyrazole 21-acetate exhibits anti-inflammatory activity greater than 84 times that of prednisolone acetate when tested in the granuloma pouch assay, thus demonstrating that this compound is about 2.4 times more active as an anti-inflammatory agent in the systemic pouch test than the corresponding 6-unsubstituted analog, i.e. 2'-phenyl-9α-fluoro-16α-methyl-11β,17α-21-trihydroxy-20-keto-4,6-pregnadieno[3,2-c]pyrazole 21-acetate and about 8.6 times more active than the corresponding despyrazole-3-keto analog, i.e. 6-azido-9α-fluoro-11β,17α,21-trihydroxy-16α-methyl-4,6-pregnadiene-3,20-dione.

Table 1

| Relative Anti-Inflammatory Potencies of 6-Azido Steroids and Analogues in the Systemic Granuloma Pouch Assay | |
|---|---|
| Compound | Relative Potency |
| Prednisolone acetate | 1 |
| 6-Azido-4,6-pregnadiene-11β,17α,21-triol-3,20-dione 21-acetate | 1.2 |
| 2'-Phenyl-11β,17α,21-trihydroxy-20-keto-4,6-pregnadieno[3,2-c]-pyrazole 21-acetate | 3.8 |
| 2'-Phenyl-6-azido-11β,17α,21-trihydroxy-20-keto-4,6-pregnadieno-[3,2-c]pyrazole 21-acetate | 17.9 |
| 6-Azido-9α-fluoro-16α-methyl-4,6-pregnadiene-11β,17α,21-triol-3,20-dione | 9.8 |
| 2'-Phenyl-9α-fluoro-11β,17α,21-trihydroxy-16α-methyl-4,6-pregnadieno[3,2-c]pyrazole 21-acetate | 36.2 |
| 2'-Phenyl-6-azido-9α-fluoro-11β,17α,21-trihydroxy-16α-methyl-20-keto-4,6-pregnadieno-[3,2-c]-pyrazole 21-acetate | 84.9 |

Illustrative of the preferred 6-azido-20-keto-4,6-pregnadieno[3,2-c]pyrazole anti-inflammatory agents defined by formula I, i.e. those wherein Y, Q and Z are oxygen functions, particularly 6-azido-17α,21-dihydroxy-20-keto-4,6-pregnadieno-[3,2-c]pyrazoles and esters thereof having an 11β-hydroxyl function or an 11-formate ester and preferably also having a 2'-phenyl or a 2'-p-substituted phenyl and a 9α-halogeno substituent, are the following:

2'-phenyl-6-azido-11β,17α,21-trihydroxy-20-keto-4,6-pregnadieno[3,2-c]pyrazole and the 21-acetate, 17-valerate, 17,21-dipropionate and 17,21-iso-propylidene derivatives thereof;

2'-phenyl-6-azido-9α-fluoro-11β,17α,21-trihydroxy-20-keto-4,6-pregnadieno[3,2-c]pyrazole;

2'-phenyl-6-azido-9α-fluoro-11β-formyloxy-17α,21-dihydroxy-20-keto-4,6-pregnadieno[3,2-c]pyrazole;

2'-phenyl-6-azido-9α-chloro-11β,17α,21-trihydroxy-20-keto-4,6-pregnadieno[3,2-c]pyrazole;

2'-phenyl-6-azido-11β,17α,21-trihydroxy-16α-methyl-20-keto-4,6-pregnadieno[3,2-c]pyrazole;

2'-p-fluorophenyl-6-azido-11β, 17α,21-trihydroxy-16α-methyl-20-keto-4,6-pregnadieno[3,2-c]pyrazole;

2'-phenyl-6-azido-9α-fluoro-11β,17α,21-trihydroxy-16α-methyl-20-keto-4,6-pregnadieno[3,2-c]pyrazole and the 21-acetate, 17-valerate, 17,21-dipropionate and 17,21-iso-propylidene derivatives thereof;

2'-p-fluorophenyl-6-azido-9α-fluoro-11β,17α,21-trihydroxy-16α-methyl-20-keto-4,6-pregnadieno[3,2-c]pyrazole;

2'-phenyl-6-azido-9α-chloro-11β,17α,21-trihydroxy-20-keto-16α-methyl-4,6-pregnadieno[3,2-c]pyrazole;

2'-phenyl-6-azido-11β,17α,21-trihydroxy-16β-methyl-20-keto-4,6-pregnadieno[3,2-c]pyrazole;

2'-p-fluorophenyl-6-azido-11β,17α,21-trihydroxy-16β-methyl-20-keto-4,6-pregnadieno[3,2-c]pyrazole;

2'-phenyl-6-azido-9α-fluoro-11β,17α,21-trihydroxy-16β-methyl-20-keto-4,6-pregnadieno[3,2-c]pyrazole and the 21-acetate, 17-valerate, 17,21-dipropionate and 17,21-iso-propylidene derivatives thereof and the corresponding 2'-p-fluorophenyl derivatives of the foregoing;

2'-phenyl-6-azido-9α-chloro-11β,17α,21-trihydroxy-16β-methyl-20-keto-4,6-pregnadieno[3,2-c]pyrazole;

2'-phenyl-6-azido-11β,16α,17α,21-tetrahydroxy-20-keto-4,6-pregnadieno[3,2-c]pyrazole, the 16,21-diacetate ester thereof, and the 16α,17α-iso-propylidene derivative thereof;

2'-phenyl-6-azido-9α-fluoro-11β,16α,17α,21-tetrahydroxy-20-keto-4,6-pregnadieno[3,2-c]pyrazole, the 16,21-diacetate ester thereof, and the 16α,17α-iso-propylidene derivative thereof;

2'-phenyl-6-azido-9α-chloro-11β-16α,17α,21-tetrahydroxy-20-keto-4,6-pregnadieno[3,2-c]pyrazole;

2'-phenyl-6-azido-11β,17α,21-trihydroxy-16-methylene-20-keto-4,6-pregnadieno[3,2-c]pyrazole;

2'-phenyl-6-azido-9α-fluoro-11β,17α,21-trihydroxy-16-methylene-20-keto-4,6-pregnadieno[3,2-c]pyrazole;

2'-phenyl-6-azido-9α-chloro-11β,17α,21-trihydroxy-16-methylene-20-keto-4,6-pregnadieno[3,2-c]pyrazole.

The 11-keto analogs of the foregoing while possessing anti-inflammatory activity, are more frequently used as intermediates in the preparation of the corresponding 11β-hydroxy-6-azido-4,6-pregnadieno[3,2-c]pyrazoles which exhibit greater anti-inflammatory activity than the 11-keto precursors.

The 6-azido-9α,11β-dihalogeno-17α,21-bisoxygenated-20-keto-4,6-pregnadieno[3,2-c]pyrazoles of this invention (especially the 17-mono- and 17,21-dilower alkanoate esters thereof) wherein X and Y are halogen (preferably wherein C-11 halogen (Y) is at least as electronegative as the C-9 halogen (X)) also possess superior anti-inflammatory activity, being useful mainly as topical anti-inflammatory agents.

Particularly valuable 6-azido-9α,11β-dihalogeno-20-keto-4,6-pregnadieno[3,2-c]pyrazoles of this group include compounds such as:

2'-phenyl-6-azido-9α,11β-dichloro-17α,21-dihydroxy-20-keto-4,6-pregnadieno[3,2-c]pyrazole, the 21-acetate, the 17-butyrate, the 17-valerate, the 17,21-dipropionate, the 17,21-dibutyrate, the 17,21-divalerate, and the 17,21-iso-propylidene derivatives thereof;

2'-phenyl-6-azido-9α,11β-dichloro-16α,17α,21-trihydroxy-20-keto-4,6-pregnadieno[3,2-c]pyrazole, the 16,21-diacetate, the 16α,17α-iso-propylidene, and the 16α,17α-iso-propylidene 21-acetate thereof;

2'-phenyl-6-azido-9α,11β-dichloro-16α-methyl-17α,21-dihydroxy-20-keto-4,6-pregnadieno[3,2-c]pyrazole, the 17-propionate, the 17,21-dipropionate, the 17,21-dibutyrate and the 17,21-divalerate thereof;

2'-phenyl-6-azido-9α,11β-dichloro-16β-methyl-17α,21-dihydroxy-20-keto-4,6-pregnadieno[3,2-c]pyrazole, the 17-propionate and the 17,21-dipropionate thereof;

2'-phenyl-6-azido-9α,11β-dichloro-16-methylene-17α,21-dihydroxy-20-keto-4,6-pregnadieno[3,2-c]pyrazole;

2'-phenyl-6-azido-9α-bromo-11β-chloro-17α,21-dihydroxy-20-keto-4,6-pregnadieno[3,2-C]pyrazole;

2'-phenyl-6-azido-9α-bromo-11β-chloro-16α-methyl-17α,21-dihydroxy-20-keto-4,6-pregnadieno[3,2-c]pyrazole;

2'-phenyl-6-azido-9α-bromo-11β-chloro-16β-methyl-17α,21-dihydroxy-20-keto-4,6-pregnadieno[3,2-c]pyrazole;

2'-phenyl-6-azido-9α-chloro-11β-fluoro-16β-methyl-17α,21-dihydroxy-20-keto-4,6-pregnadieno[3,2-c]pyrazole;

2'-phenyl-6-azido-9α-bromo-11β-chloro-16-methylene-17α,21-dihydroxy-20-keto-4,6-pregnadieno[3,2-c]pyrazole; and 2'-phenyl-6-azido-9α,11β-dibromo-17α,21dihydroxy-20-keto-4,6-pregnadieno[3,2-c]pyrazole, the 21-acetate, the 17-valerate, the 17,21-dipropionate, the 17,21-dibutyrate, the 17,21-divalerate, and the 17,21-iso-propylidene derivatives thereof.

In addition to the 11-substituted-6-azido-17α,21-dihydroxy-4,6-pregnadieno[3,2-c]pyrazoles and esters thereof of formula I listed hereinabove which are preferred as anti-inflammatory agents, our invention also includes 21-unsubstituted-, 21-fluoro and 21-chloro-6-azido-4,6-pregnadieno[3,2-c]pyrazoles having particularly useful topical anti-inflammatory properties as well as progestational activity.

Particularly useful topical anti-inflammatory agents of this group are 21-desoxy-6-azido-11-substituted -16-lower alkyl-17α-alkanoyloxy-4,6-pregnadieno[3,2-c]pyrazoles, preferably 11β-hydroxy-, 9α-halogeno-11β-hydroxy- and 9α,11β-dihalogeno derivatives thereof exemplified by 2'-phenyl-6-azido-11β,17α-dihydroxy-16α-methyl-20-keto-4,6-pregnadieno[3,2-c]pyrazole, the 9α-fluoro and 9α-chloro analogs thereof and the 17-acetate, 17-propionate, 17-n-butyrate, 17-valerate, and 11-formate-17-valerate esters of the foregoing:

2'-phenyl-6-azido-11β,17α-dihydroxy-16β-methyl-20-keto-4,6-pregnadieno[3,2-c]pyrazole, the 9α-fluoro and 9α-chloro analogs thereof and the 17-acetate, 17-propionate, 17-n-butyrate, 17-valerate, and 11-formate-17-valerate esters of the foregoing;

2'-phenyl-6-azido-11β,17α-dihydroxy-16α-methyl-20-keto-21-fluoro-4,6-pregnadieno[3,2-c]pyrazole, the 9α-fluoro and 9α-chloro analogs thereof and the 17-acetate, 17-propionate, 17-n-butyrate, 17-valerate, and 11-formate-17-valerate esters of the foregoing;

2'-phenyl-6-azido-11β,17α-dihydroxy-16β-methyl-20-keto-21-fluoro-4,6-pregnadieno[3,2-c]pyrazole, the 9α-fluoro and 9α-chloro analogs thereof and the 17-acetate, 17-propionate, 17-n-butyrate, 17-valerate, and 11-formate-17-valerate esters of the foregoing;

2'-phenyl-6-azido-11β,17α-dihydroxy-16α-methyl-20-keto-21-chloro-4,6-pregnadieno[3,2-c]pyrazole, the 9α-fluoro and 9α-chloro analogs thereof and the 17-acetate, 17-propionate, 17-n-butyrate, 17-valerate, and 11-formate-17-valerate esters of the foregoing;

2'-phenyl-6-azido-11β,17α-dihydroxy-16β-methyl-20-keto-21-chloro-4,6-pregnadieno[3,2-c]pyrazole, the 9α-fluoro and 9α-chloro analogs thereof and the 17-acetate, 17-propionate, 17-n-butyrate, 17-valerate, and 11-formate-17-valerate esters of the foregoing;

2'-phenyl-6-azido-9α,11β-dichloro-16α-methyl-17α-hydroxy-20-keto-4,6-pregnadieno[3,2-c]pyrazole and the 21-fluoro- and 21-chloro analogs thereof as well as the 17-acetate, 17-propionate, 17-n-butyrate and 17-valerate esters of the foregoing;

2'-phenyl-6-azido-9α,11β-dichloro-16β-methyl-17α-hydroxy-20-keto-4,6-pregnadieno[3,2-c]pyrazole and the 21-fluoro- and 21-chloro analogs thereof as well as the 17-acetate, 17-propionate, 17-n-butyrate and 17-valerate esters of the foregoing;

2'-phenyl-6-azido-11,20-diketo-16β-methyl-17α-hydroxy-4,6-pregnadieno[3,2-c]pyrazole, the 16α-methyl epimer thereof, and the 17-acetate, 17-caproate, and 17-valerate thereof;

2'-phenyl-6-azido-9α-fluoro-11,20-diketo-16β-methyl-17α-hydroxy-4,6-pregnadieno[3,2-c]pyrazole and the 16α-methyl epimer thereof;

2'-phenyl-6-azido-9α,21-difluoro-11,20-diketo-16α-methyl-17α-hydroxy-4,6-pregnadieno[3,2-c]pyrazole and the 16β-methyl epimer thereof;

2'-phenyl-6-azido-11,20-diketo-17α-hydroxy-16α-methyl-21-fluoro-4,6-pregnadieno[3,2-c]pyrazole and the 16β-methyl epimer thereof;

Our invention also includes 6-azido-16-lower alkyl-17α-lower alkanoyloxy-20-keto-21-desoxy-4,6-pregnadieno[3,2-c]pyrazoles unsubstituted in the C-ring which are valuable mainly as progestational agents exemplified by:

2'-phenyl-6-azido-16β-methyl-17α-acetoxy-20-keto-4,6-pregnadieno[3,2-c]pyrazole and the 16α-methyl epimer thereof;

2'-phenyl-6-azido-16β-methyl-17α-acetoxy-20-keto-21-fluoro-4,6-pregnadieno[3,2-c]pyrazole and the 16α-methyl epimer thereof; and 2'-phenyl-6-azido-16β-methyl-17α-acetoxy-20-keto-21-chloro-4,6-pregnadieno[3,2-c]pyrazole and the 16α-methyl epimer thereof.

In general, 21-desoxy compounds of our invention which are substituted in the C-ring and have a 17α-hydroxy or preferably a 17α-alkanoyloxy group possess topical anti-inflammatory activity. Those which are unsubstituted in the C-ring while possessing some corticoid activity, possess greater progestational activity and may be used as medicaments in conditions requiring a progestational agent, e.g. in fertility control and in the management of various menstrual disorders and in pregnancy maintenance.

Other 21-desoxy compounds of this invention are 6-azido-16-lower alkylidene-4,6-pregnadieno[3,2-c]pyrazoles substituted at C-17 by a hydroxy or an alkanoyloxy group (i.e. compounds of formula I wherein Q is hydroxy or alkanoyloxy having up to 12 carbon atoms, usually lower alkanoyloxy, and W is =CHT; T being H, lower alkyl, chlorine, fluorine) such as:

2'-phenyl-6-azido-16-methylene-17α-acetoxy-20-keto-4,6-pregnadieno[3,2-c]pyrazole and the corresponding 17-caproate ester thereof;

2'-phenyl-6-azido-16-n-butylidene-17α-acetoxy-20-keto-4,6-pregnadieno[3,2-c]pyrazole;

2'-phenyl-6-azido-9α,11β-dichloro-16-methylene-17α-acetoxy-20-keto-4,6-pregnadieno[3,2-c]pyrazole and the corresponding 17-caproate, 17-decanoate and the 17-dodecanoate thereof;

2'-phenyl-6-azido-16-methylene-17α-propionyloxy-20-keto-4,6-pregnadieno[3,2-c]pyrazole;

2'-phenyl-6-azido-9α,11β-dichloro-16-ethylidene-17α-acetoxy-20-keto-4,6-pregnadieno[3,2-c]pyrazole;

2'-phenyl-6-azido-9α-bromo-11β-fluoro-16-methylene-17α-acetoxy-20-keto-4,6-pregnadieno[3,2-c]pyrazole;

2'-phenyl-6-azido-9α-fluoro-11β-hydroxy-16-methylene-17α-acetoxy-20-keto-4,6-pregnadieno[3,2-c]pyrazole and the corresponding 17-caproate thereof;

2'-phenyl-6-azido-9α-fluoro-11,20-diketo-16-methylene-17α-acetoxy-4,6-pregnadieno[3,2-c]pyrazole;

2'-phenyl-6-azido-11β-hydroxy-16-methylene-17α-acetoxy-20-keto-4,6-pregnadieno[3,2-c]pyrazole;

2'-phenyl-6-azido-11,20-diketo-16-methylene-17α-acetoxy-4,6-pregnadieno[3,2-c]pyrazole;

2'-phenyl-6-azido-16-methylene-17α-acetoxy-20-keto-21-fluoro-4,6-pregnadieno[3,2-c]pyrazole;

2'-phenyl-6-azido-16-methylene-17α-acetoxy-20-keto-21-chloro-4,6-pregnadieno[3,2-c]pyrazole;

2'-phenyl-6-azido-9α,11β-dichloro-21-fluoro-16-methylene-17α-acetoxy-20-keto-4,6-pregnadieno[3,2-c]pyrazole;

2'-phenyl-6-azido-9α,11β,21-trichloro-16-methylene-17α-acetoxy-20-keto-4,6-pregnadieno[3,2-c]pyrazole;

2'-phenyl-6-azido-16-chloromethylene-17α-acetoxy-20-keto-4,6-pregnadieno[3,2-c]pyrazole;

2'-phenyl-6-azido-9α-fluoro-11β-hydroxy-16-chloromethylene-17α-acetoxy-20-keto-4,6-pregnadieno[3,2-c]pyrazole;

2'-phenyl-6-azido-16-fluoromethylene-17α-acetoxy-20-keto-4,6-pregnadieno[3,2-c]pyrazole;

2'-phenyl-6-azido-9α-fluoro-11β-hydroxy-16-fluoromethylene-17α-acetoxy-20-keto-4,6-pregnadieno[3,2-c]pyrazole;

2'-phenyl-6-azido-11β-hydroxy-16-chloromethylene-17α-acetoxy-20-keto-4,6-pregnadieno[3,2-c]pyrazole, and analogous 17α-hydroxy derivatives of the aforelisted compounds.

Other 16-substituted-21-desoxy-6-azido-4,6-pregnadieno[3,2-c]pyrazoles include 6-azido-16α,17α-dihydroxy-4,6-pregnadieno[3,2-c]pyrazoles of formula I and their 16α,17α-iso-propylidene derivatives (i.e. compounds of formula I wherein W is (H,αOH) and Q is hydroxy and their 16α,17α-alkylidene derivatives) such as:

2'-phenyl-6-azido-16α,17α-dihydroxy-20-keto-4,6-pregnadieno[3,2-c]pyrazole and the 16α,17α-iso-propylidene and 16α,17α-acetophenide derivatives thereof;

2'-phenyl-6-azido-9α,11β-dichloro-16α,17α-dihydroxy-20-keto-4,6-pregnadieno[3,2-c]pyrazole and the 16α,17α-iso-propylidene and 16α,17α-acetophenide derivatives thereof;

2'-phenyl-6-azido-9α-fluoro-11β,16α,17α-trihydroxy-20-keto-4,6-pregnadieno[3,2-c]pyrazole and the 16α,17α-iso-propylidene and 16α,17α-acetophenide derivatives thereof.

The 17α-hydroxy analogs of the aforelisted compounds are usually useful mainly as intermediates in preparing the corresponding 17α-acyloxy compounds of formula I.

Other 21-desoxy compounds of formula I of our invention are 6-azido-4,6-pregnadieno[3,2-c]pyrazoles useful mainly as progestational agents which are unsubstituted at C-9 and/or at C-11 and/or at C-17 and which are either unsubstituted at C-16 or have a 16-lower alkyl group. Some typical compounds of this class are:

2'-phenyl-6-azido-20-keto-4,6-pregnadieno[3,2-c]pyrazole and the 16α-methyl and 16β-methyl analogs thereof;

2'-phenyl-6-azido-20-keto-21-fluoro-4,6-pregnadieno[3,2-c]pyrazole and the 16α-methyl and 16β-methyl analogs thereof;

2'-phenyl-6-azido-11,20-diketo-4,6-pregnadieno[3,2-c]-pyrazole and the 16α-methyl and 16β-methyl analogs thereof;

2'-phenyl-6-azido-11β-hydroxy-20-keto-4,6-pregnadieno[3,2-c]pyrazole and the 16α-methyl and 16β-methyl analogs thereof;

2'-phenyl-6-azido-9α-fluoro-11β-hydroxy-20-keto-4,6-pregnadieno[3,2-c]pyrazole, the 16α-methyl and the 16β-methyl analogs thereof, and the corresponding 9α-chloro analogs of the foregoing;

2'-phenyl-6-azido-9α,11β-dichloro-20-keto-4,6-pregnadieno[3,2-c]pyrazole and the 16α-methyl and 16β-methyl analogs thereof;

2'-phenyl-6-azido-9α-bromo-11β-chloro-20-keto-4,6-pregnadieno[3,2-c]pyrazole and the 16α-methyl and 16β-methyl analogs thereof;

2'-phenyl-6-azido-9α,11β,21-trichloro-4,6-pregnadieno[3,2-c]pyrazole and the 16α-methyl and 16β-methyl analogs thereof; and 2'-phenyl-6-azido-9α,11β-dichloro-21-fluoro-20-keto-4,6-pregnadieno[3,2-c]pyrazole and the 16α-methyl and 16β-methyl analogs thereof.

In addition to the therapeutically active 2'-phenyl-21-oxygenated and 21-desoxy-20-keto-4,6-pregnadieno[3,2-c]-pyrazoles listed hereinabove, our invention also includes the corresponding compounds of formula I wherein the pyrazole function is unsubstituted as well as those wherein the pyrazole function is substituted by groups such as a 2'-lower alkyl (e.g. 2'-methyl, 2'-ethyl), a 2'-cycloalkyl (e.g. 2'-cyclopentyl and 2'-cyclohexyl), or by a 2'-(p-substituted phenyl) group (e.g. 2'-(p-fluorophenyl) and 2'-(p-trifluoromethylphenyl)).

Compositions-of-Matter Useful as Intermediates

Another composition-of-matter aspect of our invention includes 6-azido-7-halogeno-4-pregneno[3,2-c]pyrazoles which are useful as intermediates in preparing the therapeutically active 6-azido-4,6-pregnadieno[3,2-c]pyrazoles of this invention as described hereinbelow in the discussion of the *Process Aspect of the Invention*. These intermediates include 6-azido-7-halogeno-4-pregneno[3,2-c]pyrazoles of the following formula II:

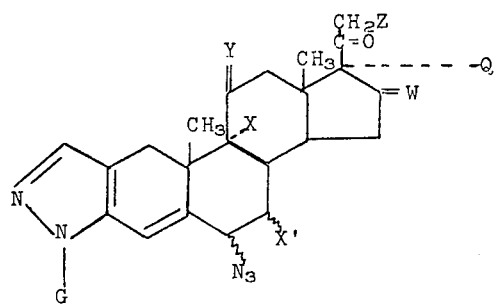

II wherein X' is a halogen of atomic weight greater than 20;

G, Q, W, X, Y and Z are as defined hereinabove for formula I;

and when Q and Z are hydroxy and W is other than (H,αOH), the (17α,20;20,21)-bisalkylidenedioxy derivatives thereof.

The above compounds of formula II are useful as intermediates in preparing the 6-azido-20-keto-4,6-pregnadieno[3,2-c]pyrazoles of formula I via one of the process aspects of our invention whereby a 6-unsubstituted-4,6-pregnadieno[3,2-c]pyrazole is treated with a halogen azide (usually bromine azide) followed by treatment of the 6-azido-7-halogeno derivative of formula II thereby formed with a dehydrohalogenating agent (e.g. tetramethyl-ammonium fluoride) whereby is obtained a compound of formula I.

The physical embodiments of the compounds of formula II, their method of preparation and use as intermediates are further illustrated in the examples hereinbelow. The requisite starting 6-unsubstituted-20-keto-4,6-pregnadieno[3,2-c]pyrazoles are either known compounds or are prepared via known procedures such as those described in the preparations hereinbelow. A convenient method for their preparation comprises treating a 3,20-diketo-6,7-unsubstituted-4,6-pregnadiene (preferably as the 17,20;20,21-bismethylenedioxy derivatives when the starting compound has a corticoid side chain at C-17, or as a 20-hydroxyl derivative when the starting compound is a 20-keto-21-desoxy-4,6-pregnadiene) with sodium hydride, sodium methoxide, and ethyl formate and thence treating the resulting 2-hydroxymethylene-3-keto-4,6-pregnadiene with hydrazine or a derivative thereof (e.g. phenylhydrazine) whereby is obtained the corresponding 20-keto-4,6-pregnadieno[3,2-c]pyrazole in the form of the 17α,20;20,21-bismethylenedioxy or 20-hydroxyl derivative. Treatment of the foregoing with acid yields the requisite 20-keto-4,6-pregnadieno[3,2-c]pyrazole having free 17α and 21-hydroxy groups and a 20-keto function. Treatment of the latter with a mild oxidizing agent, yields starting compounds having a free 20-keto-21-desoxy side chain at C-17.

Typical intermediates of formula II include compounds such as:

2'-phenyl-6-azido-7-bromo-9α-fluoro-11α,21-trihydroxy-16α-methyl-20-keto-4-pregneno[3,2-c]pyrazole 21-acetate, 16β-methyl epimer thereof, and the corresponding 7-chloro-derivatives;

2'-phenyl-67-azido-7-bromo-9α-fluoro-11,20-diketo-16α-methyl-17α,21-dihydroxy-4-pregneno[3,2-c]pyrazole 21-acetate, the 16β-methyl epimer thereof, and the corresponding 7-chloro derivatives;

2'-phenyl-6-azido-7-bromo-11β,17α,21-trihydroxy-20-keto-4,6-pregnadieno[3,2-c]pyrazole 21-acetate, the 16α-methyl and 16β-methyl homologs thereof, and the corresponding 7-chloro derivatives;

2'-phenyl-6-azido-7-bromo-11,20-diketo-17α,21-dihydroxy-4-pregneno[3,2-c]pyrazole 21-acetate, the 16α-methyl and 16β-methyl homologs thereof, and the corresponding 7-chloro derivatives.

Another composition-of-matter aspect of our invention are compounds which are valuable mainly as intermediates, i.e. compounds defined by following formula III:

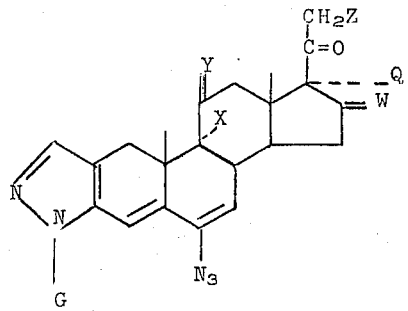

III wherein Z is a member selected from the group consisting of iodine, bromine, and hydrocarbonsulfonyloxy, said hydrocarbon having up to 7 carbon atoms; and G, Q, W, X and Y are as hereinabove defined for formula I.

The 21-hydrocarbonsulfonate ester intermediates of formula III include the 21-methanesulfonate esters, the 21-ethanesulfonate esters, the 21-benzenesulfonate esters and the 21-p-toluenesulfonate esters of the 21-hydroxy-6-azido-4,6-pregnadieno[3,2-c]pyrazoles defined by formula I. They are prepared from the corresponding 21-hydroxy precursors utilizing known methods such as that wherein the steroidal 21-alcohol (e.g. 2'-phenyl-6-azido-9α-fluoro-11β,17α,21-trihydroxy-16α-methyl-20-keto-4,6-pregnadieno[3,2-c]pyrazole) is treated with hydrocarbonsulfonyl chloride (e.g. methanesulfonyl chloride) in pyridine at low temperatures whereby is formed the corresponding steroidal 21-hydrocarbonsulfonate (e.g. 2'-phenyl-6-azido-9α-fluoro-11β,17α,21-trihydroxy-16α-methyl-20-keto-4,6-pregnadieno[3,2-c]pyrazole 21-methanesulfonate). The hydrocarbonsulfonate esters of formula III are useful intermediates in the preparation of 21-phosphate esters of formula I utilizing procedures analogous to those known in the art. Thus a 6-azido-4,6-pregnadieno[3,2-c]pyrazole 21-hydrocarbonsulfonate of formula III (e.g. 2'-phenyl-6-azido- 9α-fluoro-11β,17α,21-trihydroxy-16α-methyl-20-keto-4,6-pregnadieno[3,2-c]pyrazole 21-methanesulfonate), upon treatment with sodium bromide or preferably sodium iodide in actone, is converted to the corresponding 21-bromo- or 21-iodo derivative of formula III (e.g. 2'-phenyl-6-azido-9α-fluoro-21-iodo (or 21-bromo)-11β,17α-dihydroxy-16α-methyl-20-keto-4,6-pregnadieno[3,2-c]pyrazole), which upon treatment with phosphoric acid in methanol, yields a 21-phosphate ester of formula I (e.g. 2'-phenyl-6-azido-9α-fluoro-11β,17α,21-trihydroxy-16α-methyl-20-keto-4,6-pregnadieno[3,2-c]pyrazole 21-phosphate).

The 21-phosphate esters are also conveniently prepared by treatment of the corresponding 21-hydroxy steroid with pyrophosphoryl chloride in tetrahydrofuran whereby is obtained the 21-trichloropyrophosphate ester which decomposes in water to produce the 21-phosphate ester.

Because of their solubility characteristics, the 21-phosphate esters of 6-azido-20-keto-4,6,-pregnadieno[3,2-c]pyrazoles of formula I are particularly valuable for administration via the oral route and the intravenous route as aqueous solutions of their salts.

In addition to the foregoing, the 21-methanesulfonate esters of formula III may be used as intermediates in preparing the corresponding 21-unsubstituted steroids since, after conversion thereof to the 21-bromo- or 21-iodo-pregnane intermediate as discussed hereinabove, the resulting 6-azido-21-iodo-(or 21-bromo-)-4,6-pregnadieno[3,2-c]pyrazole (e.g. 2'-phenyl-6-azido-9α-fluoro-21-iodo-11β,17α-dihydroxy-16α-methyl-20-keto-4,6-pregnadieno[3,2-c]pyrazole may be reduced by known methods such as with sodium iodide in acetic acid to obtain the corresponding 21-desoxy-6-azido-4,6-pregnadieno [3,2-c]pyrazole of formula I, e.g. 2'-phenyl-6-azido-9α-fluoro-11β,17α-dihydroxy-16α-methyl-20-keto-4,6-pregnadieno [3,2-c]pyrazole. Alternatively, the 21-iodo (or 21-bromo-) intermediates of formula III may be converted to the corresponding 21-fluoro or 21-chloro compound of formula I by treatment thereof with silver fluoride, lithium chloride or tetraalkyl-ammonium chloride, respectively, in acetonitrile.

Another composition-of-matter aspect of this invention relates to 17α,20;20,21-bismethylenedioxy derivatives of compounds of formula I which are valuable as intermediates, said compounds being defined by the following formula IV:

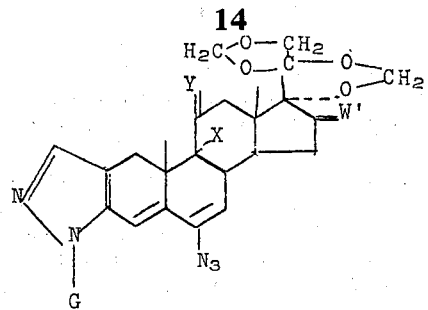

IV wherein G, X and Y are as defined for formula I and W' is a member selected from the group consisting of

(H, lower alkyl), =CHT wherein T is a member selected from the group consisting of hydrogen, lower alkyl, fluorine and chlorine.

Other valuable intermediates are 2-hydroxymethylene-6-azido-9α-X-11-Y-16-W' -17α,20;20,21-bis-methylenedioxy-4,6-pregnadiene-3-ones wherein X and Y are as defined for formula I and W' is as defined for formula IV. These compounds and those defined by formula IV are valuable as intermediates in the process aspects of our invention wherein a 3-keto-6-azido-17α,20;20,21, bismethylenedioxy-4,6-pregnadiene (e.g. 6-azido-9α-fluoro-16α-methyl-17α,20;20,21-bismethylenedioxy-4,6-pregnadiene-3-one-11β-ol) is treated with ethyl formate in strong base followed by treatment of the corresponding 2-hydroxymethylene derivative thereby formed with hydrazine or a substituted derivative thereof (e.g. phenylhydrazine) whereby is obtained a 6-azido-17α,20;20,21 bismethylenedioxy-4,6-pregnadieno[3,2-c]pyrazole of formula IV (e.g. 2'-phenyl-6-azido-9α-fluoro-17α,20;20,21-bismethylenedioxy-11β-hydroxy-16α-methyl-4,6-pregnadieno[3,2-c]pyrazole) which, upon treatment with acid or with triphenylcarbenium tetrafluoroborate according to known procedures is converted to a free 17α,21-dihydroxy-20-keto compound of formula I (e.g. 2'-phenyl-6-azido-9α-fluoro-11β,17α,21-trihydroxy-16α-methyl-20-keto-4,6-pregnadieno[3,2-c]-pyrazole having corticoid activity.

Process Aspects of the Invention

The pharmacologically active 6-azido-20-keto-4,6-pregnadieno[3,2-c]pyrazoles of formula I, particularly the 9α-halogeno derivatives thereof, are conveniently prepared via one process-aspect of our invention from the corresponding 6-unsubstituted-20-keto-4,6-pregnadieno[3,2-c]pyrazole wherein the 21-hydroxyl group is preferably protected by an ester group or by formation of a 17α,21-alkylidenedioxy derivative (e.g. 2'-phenyl-9α-fluoro-11β-17α,21-trihydroxy-16α-methyl-20-keto-4,6-pregnadieno[3,2-c]pyrazole 21-acetate and 2'-phenyl-9α-fluoro-11β-hydroxy-16α-methyl-17α,21-isopropylidenedioxy-20-keto-4,6-pregnadieno[3,2-c]pyrazole, respectively) by treatment thereof with a halogen azide (i.e. chlorine azide, iodine azide or, preferably, bromine azide) in a polar solvent system followed by treatment of the resulting 6-azido-7-halogeno -20-keto-4-pregneno[3,2-c]pyrazole (e.g. 2'-phenyl-6-azido-7-bromo-9α-fluoro-11β,17α,21- trihydroxy-16α-methyl-20-keto-4-pregneno [3,2-c]-pyrazole 21-acetate (a novel intermediate of formula II)) with a dehydrohalogenating agent in an aprotic solvent (e.g. tetramethylammonium fluoride in acetonitrile).

In preparing the 6-azido-7-halogeno intermediates or formula II bromine azide is the preferred reagent because of its greater ease of handling over chlorine azide and iodine azide. In our process, we prefer to prepare the bromine azide in situ in slight excess in the presence of the 6,7-unsubstituted-20-keto-4,6-pregnadieno[3,2-c]pyrazole (usually about 10% over the molar quantity of 6,7-unsubstituted-20-keto-4,6-pregnadieno[3,2-c]pyrazole) and to isolate the resulting novel 6-azido-7-halogeno-20-keto-4,6-pregnadieno[3,2-c]pyrazole of formula II prior to reaction thereof in an aprotic solvent with a dehydrohalogenating agent (preferably tetramethylammonium fluoride in acetonitrile).

In a preferred mode of preparing the 6-azido-7-halogeno-4,6-pregnadieno[3,2-c]pyrazoles of our invention, to 1 mole of a 6,7-unsubstituted-4,6-pregnadieno[3,2-c]pyrazole (e.g. 2'-phenyl-9α-fluoro-11β,17α,21-trihydroxy-16α-methyl-20-keto-4,6-pregnadieno[3,2-c]pyrazole or preferably the 21-acetate ester thereof) in dichlormethane to which a few drops of tertiary butanol have been added, there is first added 1.1 moles of N-bromosuccinimide and then a solution of hydrazoic acid in dichloromethane prepared from 2.5 moles of sodium azide and 2.75 moles of hydrochloric acid. The reaction mixture is stirred at room temperature from about 30 minutes to about three hours, preferably under an atmosphere of nitrogen, thence poured into water, and the resulting product isolated utilizing known techniques, such as by extraction with an organic solvent (e.g. dichloromethane), washing the resulting organic extract with aqueous sodium thiosulfate, aqueous sodium bicarbonate, then water, drying the organic solvent, thence evaporating the solution to a residue comprising a novel 6-azido-7-halogeno-20-keto4,6-pregnadieno[3,2-c]pyrazole of formula II (e.g. 2G2-phenyl-6-azido-7-bromo-9G2a-fluoro-11β,17α,21-trihydroxy-20-keto-4,6-pregnadieno[3,2-c]pyrazole 21-acetate).

In the foregoing procedure, in place of N-bromosuccinimide there may be used acyl amides such as N-bromoacetamide, 1,3-dibromo-5,5-dimethylhydantoin, and the like.

Solvents preferred for use in the foregoing process are halogenated hydrocarbons such as chloroform, ethylene dichloride, dichloromethane; however, other solvents may also be used such as ethers, 1,2-dimethoxyethane, acetonitrile, tetrahydrofuran and the like.

The 6-azido-7-halogeno-20-keto-4,6-pregnadieno[3,2-c]pyrazoles of formula II are usually off-white, crystalline solids of sufficient purity to use without further purification in the dehydrohalogenation process of our invention.

When dehydrohalogenating a 6-azido-7-halogeno-20-keto-4,6-pregnadieno[3,2-c]pyrazole according to our process, the preferred reagent is a tetraalkylammonium halide, usually tetramethylammonium fluoride as the pentahydrate. Other dehydrohalogenating agents which may be used are calcium carbonate, diazabicyclooctane (DABCO), diazabicyclononane (DBN), diazabicycloundecane (DBU), and concentrated hydrochloric acid in a lower alkanoic acid.

Generally, when carrying out a preferred mode of our dehydrohalogenation process, to a mole of the 6-azido-7-halogeno-20-keto-4-pregneno[3,2-c]pyrazole (e.g. 2G2-phenyl-6-azido-7-bromo-9G2a-fluoro-11β,17α,21-trihydroxy-16G2a-methyl-20-keto-4-pregneno[3,2-c]pyrazole or the 21-acetate thereof, in solution or suspension in an aprotic solvent (usually acetonitrile) there is added (either in the solid state or in solution) tetraalkylammonium halide (preferably tetramethylammonium fluoride) in quantities ranging from 1.5 to 5 moles per mole of steroid. The reaction mixture is stirred or left standing at temperatures ranging from about 0°C to about 80°C until the dehydrohalogenation at C-7(6) is completed as evidenced by thin layer chromatography or by spectroscopic evaluation (Reaction times usually range from a few hours to several days.) The resulting 6-azido-20-keto-4,6-pregnadieno[3,2-c]pyrazole (e.g. 2G2-phenyl-6-azido-9G2a-fluoro-11β,17α,21-trihydroxy-16G2a-methyl-20-keto-4,6-pregnadieno[3,2-c]pyrazole or 21-acetate thereof) is isolated utilizing known techniques. Usually, the reaction mixture is poured into water, extracted with ether, the organic extract washed with water, dried and evaporated to a residue comprising the desired 6-azido-20-keto-4,6-pregnadieno[3,2-c]pyrazole (e.g. 2G2-phenyl-6-azido-9G2a -fluoro-11β,17α,21-trihydroxy-16G2a-methyl-20-keto-4,6-pregnadieno[3,2-c]pyrazole or the 21-acetate thereof). Purification is effected utilizing known techniques including chromatography and crystallization methods.

Aprotic solvents suitable for use in our process include dimethylsulfoxide, dimethylacetamide, dioxane, tetrahydrofuran, and preferably acetonitrile or dimethylformamide.

The tetraalkylammonium halide reagents necessary to our process are known in the art. We have found it most convenient to use tetramethylammonium chloride, or, preferably, tetramethylammonium fluoride, since they are commercially available and good product yields are obtained thereby. When utilizing the commercially available tetramethylammonium fluoride pentahydrate as reagent, the water of hydration may be removed therefrom by azeotropic distillation with acetonitrile although the reaction will proceed when the pentahydrate is used as reagent. When preparing the anhydrous form of the tetramethylammonium fluoride reagent, the azeotropic distillation is continued until the reagent is a solid at 50°C, at which point it is most suitable for use as a dehydrohalogenating reagent to convert a 6-azido-7-halogeno-4-pregneno[3,2-c]pyrazole to a 6-azido-4,6-pregnadieno[3,2-c]pyrazole.

The tetraalkylammonium halide reagents have limited solubility in the aprotic solvents utilized in this process; therefore, it is preferable to stir the reaction mixture when dehydrohalogenating at C-7(6). The reaction will proceed without stirring, however, with the tetraalkylammonium halide dissolving as the reaction proceeds.

Our process whereby a 6-unsubstituted-4,6-pregnadieno[3,2-c]pyrazole upon treatment with a halogen azide, is converted to the corresponding 6-azido-7-halogeno-4-pregneno[3,2-c]pyrazole and thence dehydrohalogenated to produce a 6-azido-4,6-pregnadieno[3,2-c]pyrazole, is advantageously carried out under mild conditions at temperatures in the range of from about 0°C to about 80°C (usually at room temperature) in a media which is close to neutrality. Our process is of particular value, therefore, when preparing a 6-azido-4,6-pregnadieno[3,2-c]pyrazole which possesses groupings sensitive to strong acids or strong bases, for example, when preparing a 6-azido-4,6-pregnadieno[3,2-c]pyrazole of the corticoid series possessing the dihydroxyacetone side chain at C-17 or a 6-azido-4,6-pregnadieno[3,2-c]pyrazole of the progesterone series having a 17G2a-acetoxy function, both of which groupings are known to react with strong bases.

Substituents present in the 6-unsubstituted-4,6-pregnadieno[3,2-c]pyrazole starting steroids of our process usually remain unchanged under the conditions of this process; thus, by way of example, the 6-azido-4,6-pregnadieno[3,2-c]pyrazole starting steroids of this process aspect of our invention may be substituted at C-1 by a lower alkyl group; at C-9 by halogen; at c-11 by oxygen, hydroxyl, formyloxy and halogen; at C-16 by lower alkyl, lower alkylidene, halogenoalkylidene, halogen, or alkanoyloxy; and at C-17 there may be present a corticoid side chain or 17G2a-substituted progesterone side chain, as well as esters and derivatives thereof.

This process aspect of our invention provides a convenient method for introducing a 6-azido group into 4,6-pregnadieno[3,2-c]pyrazoles utilizing novel 6-azido-7-halogeno-4-pregneno[3,2-c]pyrazoles heretofore unknown in the art. This process is particularly useful when the starting 6-unsubstituted steroid possesses a 9G2a-halogeno-11G2s-hydroxyl function since the desired 6-azido-9G2a-halogeno-11G2s-hydroxy-pregnadieno pyrazole is produced in two reaction steps whereas it takes a minimum of four steps to produce a 9,11-halohydrin of this invention from a despyrazolo-6-azido steroid by the other process of this invention discussed hereinbelow. This process is also of particular value since it has been found one cannot produce isolatable quantities of 6-azido derivatives of 4,6-pregnadieno[3,2-c]pyrazoles by methods analogous to those known in the art for preparing 6-azido derivatives of 3-keto-4,6-pregnadienes, such as the method whereby a 3-keto-4,6-pregnadiene is converted to the corresponding 6α,7G2a-oxido derivative, thence to a 6G2s-azido-7G2a-acyloxy derivative which is dehydrocylated with a tetraalkylammonium halide or with hydrochloric acid in the presence of a lower alkanoic acid in an inert solvent.

The 6-unsubstituted-4,6-pregnadieno[3,2-c]pyrazole starting steroids of this process are all either known compounds or are prepared conveniently from the corresponding 3-keto-6-unsubstituted -4,6-pregnadienes utilizing known techniques such as disclosed specifically in the Preparations herein. In general, a 6-unsubstituted-3-keto-4,6-pregnadiene wherein the cortical side chain is preferably protected as a bismethylenedioxy group or wherein the progesterone side chain is protected by reduction of the 20-keto group to a 20-hydroxyl function by means known in the art, is treated with alkyl formate in the presence of a strong base under an inert atmosphere, whereby is formed the corresponding 2-hydroxymethylene derivative which, in turn, may either be treated with hydrazine or a mono-substituted hydrazine, whereby is formed a 4,6-pregnadieno[3,2-c]pyrazole or substituted pyrazole. Alternatively, the 2-hydroxymethylene intermediate may be converted to the corresponding 2-alkoxymethylene derivative by treatment with a lower alkanol in the presence of acid and the resulting alkoxymethylene derivative treated with hydrazine or a mono-substituted hydrazine whereby a 6-unsubstituted-4,6-pregnadieno[3,2-c]pyrazole is formed. Thus, for example, 1,2-dihydro-6-dehydrodexamethasone in the form of the 17α,20;20,21-bismethylenedioxy derivative (i.e. 9G2a-fluoro-16G2a-methyl-17α,20;20,21-bismethylenedioxy-4,6-pregnadiene-11G2s-ol-3-one) in anhydrous tetrahydrofuran/benzene, upon treatment with ethyl formate in the presence of sodium hydride and sodium methoxide, is converted to the corresponding 2-hydroxymethylene derivative which, upon treatment with phenylhydrazine in ethanol at reflux temperature, produces a 2G2-phenylpyrazole derivative, namely 2G2-phenyl-9G2a-fluoro-11G2s-hydroxy-16G2a-methyl-17α,20;20,21-bismethylenedioxy-4,6-pregnadieno[3,2-c]pyrazole which upon treatment with an acid (e.g. 60% aqueous formic acid), is converted to the steroidal pyrazole having a free cortical side chain, namely 2G2 -phenyl-9G2a-fluoro-11β,17α,21-trihydroxy-16α-methyl-20-keto-4,6-pregnadieno[3,2-c]pyrazole.

In another process of this invention, the 6-azido-20-keto-4,6-pregnadieno[3,2-c]pyrazoles of formula I are prepared by treating a 3,20-diketo-6-azido-4,6-pregnadiene in the form of its 17α,20;20,21-bis-methylenedioxy derivative with an alkyl formate in the presence of strong base and followed by treatment of the resulting 2-hydroxymethylene derivative with hydrazine (whereby is formed a 6-azido-4,6-pregnadieno[3,2-c]pyrazole) or with a mono-substituted hydrazine (whereby is formed predominantly a 2G2-substituted-6-azido-4,6-pregnadieno[3,2-c]pyrazole). Alternatively, the 2-hydroxymethylene derivative is converted to the corresponding 2-alkoxymethylene derivative by treatment with a lower alkanol in the presence of acid and thence treatment of the resulting alkoxymethylene derivative with hydrazine or a monosubstituted hydrazine whereby is formed a 6-azido-4,6-pregnadieno[3,2-c]pyrazole or a 2G2-substituted derivative thereof, respectively.

Among the monosubstituted hydrazines which may be used for the process of our invention are: alkylhydrazines, such as methylhydrazine, ethylhydrazine, propylhydrazines, butylhydrazines, cycloalkylhydrazines; arylhydrazines including phenylhydrazine and the substituted phenylhydrazines, such as o-, m-, and p-halophenylhydrazines, o-, m-, and p-tolyhydrazines, o-, m-, and p-alkoxyphenylhydrazines, o-, m-, and p-nitrophenylhydrazines, 1-hydrazinonaphthalene, 2-hydrazinopyridine, 3-hydrazinopyridine, 4-hydrazinopyridine, 4-hydrazinopyridine oxide, and 2-hydrazinopyrimidine; aralkylhydrazines, such as benzylhydrazine and α(or β)-phenylethylhydrazine.

There are thereby produced 2G2-substituted-6-azido-4,6-pregnadieno[3,2-c]pyrazoles including: 2G2-alkyls such as 2G2-methyl-, 2G2-ethyl-, 2G2-butyl-, 2G2-propyl-, 2G2-(β-hydroxyethyl)-; 2G2-cycloalkyl-; 2G2-aryl- which may be derived from any aromatic nucleus, including 2G2-phenyl- and the 2G2-substituted-phenyl derivatives such as o-, m-, and p-halogenophenyl; o-, m-, and p-tolyl; o-, m-, and p-alkoxyphenyl-, o-, m-, and p-nitrophenyl-; 2G2-(1G2-naphthyl)-, 2G2-(2G2-pyridyl)-, 2G2-(3G2-pyridyl)-, 2G2-(4G2-pyridyl)-, 2G2-(4G2-pyridyloxide)-, 2G2-(2G2-pyrimidyl)-; 2G2-aralkyl-, such as 2G2-benzyl- and 2G2-phenylethenyl-4,6-pregnadieno[3,2-c]pyrazoles.

Preferred hydrazine reagents for this process aspect of our invention are phenylhydrazine and p-fluorophenylhydrazine whereby are produced preferred compounds of this invention, namely, 2G2-phenyl-6-azido-4,6-pregnadieno[3,2-c]pyrazoles and 2G2-(p-fluorophenyl)-6-azido-4,6-pregnadieno[3,2-c]pyrazoles of formula I.

The 2G2-alkyl-6-azido-4,6-pregnadieno[3,2-c]pyrazoles of formula I (i.e. those compounds wherein G is alkyl or cycloalkyl) may also be prepared by direct alkylation of the N-unsubstituted-6-azido-4,6-pregnadieno[3,2-c]pyrazoles of formula I (i.e. those compounds wherein G is H).

In this process, prior to reaction with an alkyl formate, starting compounds having a cortical side chain at C-17 and an 11G2s-hydroxyl group, particularly those also having a 9G2a-halogeno substituent, can be converted to the corresponding 11-keto-17α,20;20,21-bismethylenedioxy derivative; in the case of starting compounds having a progesterone side chain at C-17, the 20-keto is converted to the 20-hydroxyl derivative. The 3,11-diketo-6-azido-or the 3-keto-6-azido-9G2a-halogeno-11-keto-4,6-pregnadiene intermediate is then treated with ethyl formate in the presence of strong base and the resulting 2-hydroxymethylene derivative is reacted with hydrazine or a monosubstituted hydrazine to give a 6-azido-11-keto-4,6-pregnadieno[3,2-c]pyrazole or 6-azido-9G2a-halogeno-11-keto-4,6-pregnadieno[3,2-c]pyrazole of this invention in the form of the 17α,20;20,21-bismethylenedioxy or 20-hydroxy derivative. The 11-keto-4,6-pregnadieno pyrazole derivatives are then reduced to the corresponding 11G2a-hydroxy derivative, by methods known in the art. Alternatively, compounds of this invention containing an 11G2s-hydroxyl function are prepared by this process utilizing 11G2a-hydroxy intermediates. Thus, for example, when preparing 2G2-phenyl-6-azido-9G2a-fluoro-11β,17α,21-trihydroxy-16G2a-methyl-20-keto-4,6-pregnadieno[3,2-c]pyrazole by this process, 6-azido-1,2-dihydro-6-dehydrodexamethasone is first converted to the 17α,20;20,21-bismethylenedioxy derivative (i.e. 6-azido-9G2a-fluoro-16G2a-methyl-17α,20;20,21-bismethylenedioxy-4,6-pregnadiene-11G2s-ol-3-one), thence treated with ethyl formate and sodium hydride, followed by treatment of the 2-hydroxymethylene derivative thereby formed with phenylhydrazine to yield 2G2-phenyl-6-azido-9G2a-fluoro-11G2s-hydroxy-16G2a-methyl-17α,20;20,21-bismethylenedioxy-4,6-pregnadieno[3,2-c]pyrazole, which upon treatment with a dilute acid (e.g. 60% aqueous formic acid) or with triphenylcarbenium tetrafluoroborate yields a 9G2a-fluoro-11β,17α,21-trihydroxy compound of formula I, i.e. 2G2-phenyl-6-azido-9G2a-fluoro-11β,17α,21-trihydroxy-16G2a-methyl-20-keto-4,6-pregnadieno[3,2-c]pyrazole.

The 2G2-N-acyl derivatives of our invention (i.e. those compounds of formula I wherein G is a lower hydrocarboncarboxylic acyl) are prepared by treating an N-unsubstituted-17α,20;20,21-bis-methylenedioxy derivative of formula IV or an N-unsubstituted-20-keto-21-desoxy derivative of formula I with an acylating agent, e.g. a lower hydrocarbon carboxylic acid acylating agent such as benzoic anhydride or tertiary butyl acetyl chloride; a lower alkanoic anhydride such as acetic anhydride or propionic anhydride; a lower alkanoyl halide such as acetyl chloride; or a polybasic anhydride such as β,β-dimethylglutaric anhydride, succinic anhydride, and the like, in the presence of an organic base such as pyridine.

As mentioned hereinabove, upon treatment of a 6-azido-17α,20;20,21-bis-methylenedioxy-4,6-pregnadieno[3,23,2]pyrazoles with a dilute acid or with triphenylcarbenium tetrafluoroborate, the BMD protecting group is removed and there is obtained the corresponding 6-azido-17α,21-dihydroxy-20-keto-4,6-pregnadieno[3,2-c]pyrazoles of formula I.

Any acyl groups present in the 2G2-position (i.e. those compounds wherein G is a hydrocarbon carboxylic acyl) may be removed by treating the steroidal pyrazole as the BMD derivative with sodium methoxide in methanol to form the corresponding compound of formula I wherein G is hydrogen. Under these conditions, a 9,11-halohydrin may convert to a 9β,11β-epoxide, thus requiring regeneration to the 9,11-halohydrin by treatment with a hydrogen halide according to known procedures.

2'-acyl-21-acrylate derivatives of our invention (i.e. compounds of formula I wherein G is a hydrocarbon carboxylic acyl and Z is —OR₂, R₂ being a hydrocarbon carboxylic acid radical) in which both acyl derivatives are the same, may be prepared (1) by reacting a 6-azido-21-hydroxy-20-keto-4,6-pregnadieno[3,2-c]pyrazole of formula I wherein G is H and Z is hydroxy with two equivalents of an acylating agent or (2) by reaction of a 2G2-acyl-21-hydroxy-20-keto-4,6-pregnadieno[3,2-c]pyrazole (i.e. a compound of formula I wherein G is acyl and Z is hydroxy) with one equivalent of an acylating agent in which the acyl group of the acylating agent is the same as the acyl group already present at the 2G2-position of the pyrazole.

The 2'-acyl-21-acylate derivatives of the above described 6-azido-17α,21-dihydroxy-20-keto-4,6-pregnadieno[3,2-c]pyrazoles in which the acyl groups are different are prepared by reaction of a 2'-acyl-17α,21-dihydroxy-20-keto-4,6-pregnadieno[3,2-c]pyrazole of formula I with an acylating agent in which the acyl group of the acylating agent is diffferent from the acyl group already present at the 2'-position of the pyrazole.

Acylating agents which can be used for this purpose include a lower hydrocarbon carboxylic acid acylating agent such as benzoic anhydride, tertiary butyl acetyl chloride; a lower alkanoic anhydride or lower alkanoyl halide such as acetic anhydride, propionic anhydride; or a polybasic anhydride such as β,β-dimethylglutaric anhydride, succinic anhydride and the like, in the presence of an organic base such as pyridine.

A 6-azido-20-keto-4,6-pregnadieno[3,2-c]pyrazole of formula I wherein Z is hydroxyl may be converted to a 21-desoxy compound of formula I (i.e. wherein Z is hydrogen) by treating a 6-azido-20-keto-17α,21-dihydroxy-4,6-pregnadieno[3,2-c]pyrazole of formula I with methanesulfonyl chloride in a nonaqueous base (e.g. pyridine, triethylamine, collidine, N-methylmorpholine) whereby is formed a 21-methanesulfonyl derivative of formula III. Prior to treatment with methanesulfonyl chloride, a steroid starting compound in which G is hydrogen is preferably converted to the corresponding 2G2-acyl derivative before undergoing this reaction. The 6-azido-17α,21-dihydroxy-20-keto-4,6-pregnadieno[3,2-c]pyrazole 21-mesylate of formula III is then treated with an alkali iodide to form the corresponding 21-iodo compound (i.e. a compound of formula III wherein Z is iodine). Treatment of the foregoing 6-azido-17G2a-hydroxy-20-keto-21-iodo-4,6-pregnadieno[3,2-c]pyrazole of formula III with sodium iodide in acetic acid will yield the corresponding 21-desoxy compound of this invention, i.e. a compound of formula I wherein Z is hydrogen. Alternatively, treatment of the 21-iodo (or 21-bromo) intermediates with silver fluoride or silver chloride, respectively, in acetonitrile will yield the corresponding 21-fluoro and 21-chloro compounds.

The 21-dihydrogen phosphate esters of this invention (i.e. compounds of formula I wherein Z is $OR_2$, $R_2$ being the acyl radical of phosphoric acid) are prepared by reaction of the corresponding 21-iodo-compound (compound of formula III wherein Z is iodine) with a mixture of silver phosphate and phosphoric acid or, preferably, by reaction of the corresponding 21-hydroxy compound with pyrophosphoryl chloride utilizing known techniques. Both the mono- and dialkali metal salts and alkaline earth metal salts of the dihydrogen phosphate ester thereby formed may be obtained by neutralizing said dihydrogen phosphate ester with an alkali methoxide or alkaline earth methoxide. Treatment of a dialkali or alkaline earth metal salt of a 21-phosphate ester of formula I wherein G is an acyl radical with additional alkali methoxide will convert the N-acyl compound of formula I into a free amine, i.e. a compound of formula I wherein G is hydrogen. Compounds of formula I wherein Z is a dialkali metal salt of a phosphoric acid radical may be converted to the free dihydrogen phosphate by contacting the 21-phosphate ester metal salt with an ion exchange resin.

Preparation of Esters of Our Invention 6-azido-4,6-pregnadieno[3,2-c]pyrazoles of formula I having ester groups such as at C-16, C-17, and C-21 can be converted in known manner into 6-azido-4,6-pregnadieno[3,2-c]pyrazoles having free hydroxyl groups as, for example, by the action of acidic or alkaline saponification agents. When the 6-azido-4,6-pregnadieno[3,2-c]pyrazoles of formula I contains a chlorohydrin or bromohydrin at C-9 and C-11 (i.e. wherein X is halogeno and Y is (H,βOH)), we prefer to hydrolyze in a slightly acid medium, e.g. utilizing 70% perchloric acid in methanol-chloroform to minimize epoxide formation at C-9 and C-11. When hydrolyzing ester groups of compounds of formula I not containing a 9(11)-chlorohydrin or bromohydrin, we usually prefer to use methanolic sodium hydroxide keeping the reaction medium at about 0°C and under an inert atmosphere, e.g. Argon. If an ester group is present at C-11, such as in 2G2-phenyl-6-azido-9G2a-fluoro-11β,17α,21-trihydroxy- 16G2a-methyl-20-keto-4,6-pregnadieno[3,2-c]pyrazole triacetate, it is convenient to convert the esterified compound to the free hydroxy analog by the action of the microorganism *Flavobacterium dehydrogenans*.

Similarly, alkylidenedioxy functions at C-17(21) in a 6-azido-4,6-pregnadieno[3,2-c]pyrazole of formula I can be converted in known manner to the corresponding 17,21-dihydroxy steroid in an acidic medium (e.g. 50% aqueous acetic acid) under an atmosphere of nitrogen.

Compounds of formula I, prepared in accordance with our invention, which possess a 21-hydroxyl group, can be converted into pharmacologically acceptable esters utilizing known procedures. When preparing hydrocarbon carboxylic acid esters of hydroxy groups at C-21 and most secondary hydroxy groups such as at C-16, we prefer to utilize as esterification medium an acid anhydride in pyridine at room temperature, e.g. acetic anhydride, propionic anhydride, valeric anhydride in pyridine. When an ester of an aromatic carboxylic acid is desired, the acyl halide, e.g. benzoyl chloride, toluyl chloride, in pyridine is preferably utilized as esterification agent.

Similarly, procedures known in the art are utilized to convert a 17,21-dihydroxy compound of our invention, e.g. of formula I to the corresponding 17-mono-acyl or 17,21-di-acyl derivative, e.g. of formula I. Thus, 17α,21-diesters may be prepared by acylation of the corresponding 17α,21-diols or 17G2a-hydroxy-21-acyloxy compounds. This is preferably effected by reaction of the steroid with an appropriate acid anhydride in the presence of a strong acid catalyst such as, e.g. p-toluenesulfonic acid, perchloric acid or strongly acidic cation exchange resins, or by using trifluoroacetic anhydride with an appropriate lower alkanoic acid. The reaction may be carried out in the absence of a solvent or in a non-polar solvent, e.g. carbon tetrachloride, benzene, toluene, methylenechloride and chloroform. Heating may or may not be necessary according to the reactivity of the reaction components.

When preparing a compound of formula I having different acyl groups at C-17 and C-21, one may first prepare a 21-monoester and then esterify the C-21 monoacylate under more forcing conditions to introduce a different acyl group in the 17α-position.

Prior to esterifying a 17G2a-hydroxyl group, any 11G2s-hydroxyl function ought be protected such as by preparing the 11G2s-trifluoroacetate ester which, after esterification at C-17, may be hydrolyzed with mild base (e.g. dilute aqueous sodium bicarbonate) without hydrolyzing the other ester groups at C-17 and/or at C-21.

The 17,21-diesters may also be prepared by acylation of the corresponding 21-hydroxy-17G2a-monoesters by treatment thereof with the appropriate acid anhydride or acid chloride under basic conditions, preferably in the presence of a tertiary organic base, e.g. pyridine, quinoline, N-methylpiperidine, N-methylmorpholine, p-dimethylaminopyridine or dimethylaniline. The reaction may be carried out with or without solvents or with or without heat as may be necessary.

The 17G2a-monoesters of our invention may be prepared by hydrolysis of a corresponding 17,21-orthoester or 17α,21-diester.

In preparing 17-monoesters via hydrolysis of a 17,21-orthoester, the 17,21-orthoester is conveniently prepared by reaction of the 17α, 21-diol with an alkylorthoester followed by hydrolysis of the resulting 17,21-orthoester under mild conditions, i.e. hydrolysis in the presence of an acid catalyst, e.g. a lower alkanoic acid such as acetic or propionic, or a strong mineral acid such as hydrochloric, sulfuric acid. When no substituent is present at C-16 the hydrolysis is preferably carried out under buffered conditions at a pH in the range of 4 to 6.

The acyl groups at C-17 and at C-21 of the 17-monoacyloxy and 17,21-diacyloxy-6-azido-4,6-pregnadieno[3,2-c]pyrazoles of formula I may be introduced either before or after the 6-azido function is present in the molecule. When a BMD derivative is utilized in our process, the ester groups are necessarily introduced after removal of the BMD function.

The novel 6-azido-20-keto-16α,17α,21-trihydroxy compounds of formula I may be converted to the 6-azido-16α, 17α-alkylidenedioxy derivatives utilizing procedures known in the art, e.g. by reacting an 11β,16α,17α-trihydroxy steroid of formula I (e.g. 6-azido-11β, 16α,17α,21-tetrahydroxy-20-keto-4,6-pregnadieno[3,2-c]pyrazole) with a ketone or aldehyde (e.g. acetone, acetylaldehyde, acetophenone) in the presence of a mineral acid (e.g. hydrochloric acid)

whereby is obtained the corresponding 16α,17α-alkylidenedioxy derivative (e.g. 6-azido-11β,21-dihydroxy-16α,17α-isopropylidenedioxy-20-keto-4,6-pregnadieno[3,2-c]pyrazole).

Similarly, 17,21-alkylidenedioxy derivatives of formula I may be prepared from the corresponding 17,21-dihydroxy-20-keto derivatives by treatment with a ketone, aldehyde, acetal, or lower alkyl ketal in the presence of a small amount of acid utilizing known techniques. For example, 2'-phenyl-6-azido-11β-hydroxy-20-keto-17α,21-dihydroxy-4,6-pregnadieno[3,2-c]pyrazole and 2,2-dimethoxypropane in dimethylformamide in the presence of a catalytic amount of p-toluenesulfonic acid produces 2'-phenyl-6-azido-11β-hydroxy-17α,21-isopropylidenedioxy-20-keto-4,6-pregnadieno[3,2-c]pyrazole.

The present invention includes within its scope pharmaceutical compositions comprising our novel 6-azido-20-keto-4,6-pregnadieno[3,2-c]pyrazoles of formula I in association with a compatible, pharmaceutically acceptable carrier or coating. Also included within our invention is the method of eliciting an anti-inflammatory response in a warm-blooded animal having a susceptible inflammatory disorder which comprises administering to said animal a nontoxic, anti-inflammatorily effective amount of a 6-azido-20-keto-4,6-pregnadieno[3,2-c]pyrazole of formula I.

In general, the pharmacologically active 6-azido-20-keto-4,6-pregnadieno[3,2-c]pyrazoles of this invention as defined by formula I have pharmacological effects similar to that of the corresponding 6-unsubstituted analog and may be administered in similar pharmaceutical forms and for the same indications for which the corresponding 6-unsubstituted-20-keto-4,6-pregnadieno[3,2-c]pyrazole or the corresponding 3,20-diketo-6-azido-4,6-pregnadiene would be applicable, the total daily dosage depending upon the nature and severity of the inflammation being treated, the age and size of the patient, and the specific potency of the 6-azido-20-keto-4,6-pregnadieno[3,2-c]pyrazole being administered. When administering preferred compounds of our invention, i.e. 6-azido-17α,21-dihydroxy-20-keto-4,6-pregnadieno[3,2-c]pyrazoles of formula I having an oxygen function at C-11 or a 9α,11β-dihalogeno grouping, particularly those substituted at C-16 by a methyl, methylene or α-hydroxyl group and at N-2' by a phenyl or p-fluorophenyl group, the therapeutic dosages advantageously will generally be lower than those required when administering the corresponding 6-unsubstituted analog or the corresponding 3-keto-despyrazole analog as evidenced by the therapeutic ratios set forth in Table I hereinabove.

The 6-azido-4,6-pregnadieno[3,2-c]pyrazoles of formula I may be administered orally in the form of tablets, elixirs, capsules and the like for all inflammatory disorders, particularly arthritis, rheumatism and the like; intravenously in aqueous solution as the 21-hemisuccinate or 21-phosphate ester for the treatment of shock; intramuscularly for long-term systemic activity or intra-articularly for long-term local activity with minimal systemic effects in aqueous suspension as the 17,21-dilower alkanoate esters, e.g. 17,21-dipropionate, and 17,21-dibutyrate; or topically in creams, lotions, aerosols or ointments as the 17-mono lower alkanoate (e.g. 17-valerate) or as the 17,21-diesters (e.g. 17,21-dipropionate) in the treatment of contact and allergic dermatitis and psoriasis; or in the form of ophthalmic suspensions or nasal sprays. In each instance, the pharmaceutical dosage forms are prepared according to procedures well known in the art and may contain other active ingredients, e.g. neomycin sulfate in creams for topical use.

The pharmaceutical formulations of this invention are prepared by combining the active ingredient (i.e. a compound of formula I) with conventional pharmaceutical diluents and carriers which are based upon the desired route of administration.

The following examples illustrate pharmaceutical compositions according to this invention as well as the process and compounds claimed herein.

PHARMACEUTICAL COMPOSITIONS

Following are examples of pharmaceutical compositions comprising 2'-phenyl-6-azido-11β,17α,21-trihydroxy-20-keto-4,6-pregnadieno[3,2-c] pyrazole 21-acetate and 2'-phenyl-6-azido-9α-fluoro-11β,17α,21-trihydroxy-16α-methyl-20-keto-4,6-pregnadieno[3,2-c]pyrazole 21-acetate which are illustrative of formulations in which the compounds of out invention may be incorporated.

I. Parenteral Compositions

| A. Intramuscular or Subcutaneous Aqeuous Suspension | mg/ml |
|---|---|
| 2'-phenyl-6-azido-9α-fluoro-11β,17α,21-trihydroxy-16α-methyl-20-keto-4,6-pregnadieno[3,2-c]pyrazole 21-acetate (sterile precipitated) | 0.1–0.3 |
| Monobasic Sodium Phosphate | 6.0 |
| Dibasic Sodium Phosphate Anhydrous | 0.5 |
| Polysorbate 80, USP | 0.05 |
| Benzyl Alcohol, R | 9.0 |
| Methylparaben, USP | 1.3 |
| Propylparaben, USP | 0.2 |
| Sodium Chloride, USP | 2.5 |
| Sodium Carboxymethylcellulose, USP | 3.0 |
| Disodium Edetate, USP | 0.1 |
| Water for Injection, USP q.s. ad | 1.0 ml. |

| B. Intramuscular or Subcutaneous Oil Injection | mg/ml |
|---|---|
| 2'-phenyl-6-azido-9α-fluoro-11β,17α,21-trihydroxy-16α-methyl-20-keto-4,6-pregnadieno[3,2-c]pyrazole 21-acetate (sterile precipitated | 0.1–0.3 |
| Aluminum Monostearate, USP | 20.0 |
| Propylparaben, USP | 1.0 |
| Sesame Oil, USP (heat treated) q.s ad | 1.0 ml. |

| C. Intra-articular Injection | mg/ml |
|---|---|
| 2'-phenyl-6-azido-9α-fluoro-11β,17α,21-trihydroxy-16α-methyl-20-keto-4,6-pregnadieno[3,2-c]pyrazole 21-acetate | 0.1–0.3 |
| Sodium Chloride, USP | 7.0 |
| Sodium Carboxymethylcellulose, USP | 3.0 |
| Polysorbate 80, USP | 0.05 |
| Benzyl Alcohol, R | 9.0 |
| Water for Injection, USP q.s. ad | 1.0 ml. |

| D. Intravenous Infusion | mg/ml |
|---|---|
| 2'-phenyl-6-azido-9α-fluoro-11β,17α,21-trihydroxy-16α-methyl-20-keto-4,6-pregnadieno[3,2-c]pyrazole 21-acetate | 0.1–0.3 |

-continued

| D. Intravenous Infusion | mg/ml |
|---|---|
| Dimethylacetamide q.s. ad | 1.0 ml. |

NOTE:
This infusion is to be diluted with 500 ml of 5% Dextrose Injection, USP before administration.

In above compositions IA, IB, IC, and ID 0.5 to 0.8 mg/ml of 2'-phenyl-6-azido-11β,17α,21-trihydroxy-20-keto-4,6pregnadieno[3,2-c]pyrazole 21-acetate may be used in place of the 0.1 to 0.3 mg/ml of 2'-phenyl-6-azido-9α-fluoro-11β,17α,21-trihydroxy-16α-methyl-20-keto-4,6-pregnadieno[3,2-c]pyrazole 21-acetate.

II. Ophthalmic Compositions

| A. Ointment | mg/g |
|---|---|
| 2'-phenyl-6-azido-9α-fluoro-11β,17α,21-trihydroxy-16α-methyl-20-keto-4,6-pregnadieno[3,2-c]pyrazole 21-acetate (microcrystalline, sterile) | 5.0 |
| Gentamicin base | 3.0 |
| Methylparaben, USP | 0.1 |
| Propylparaben, USP | 0.5 |
| Phenyl ethanol | 0.5 |
| Mineral Oil, USP | 179.0 |
| White Petrolatum, USP | 811.9 |

| B. Ointment | mg/g |
|---|---|
| 2'-phenyl-6-azido-9α-fluoro-11β,17α,21-trihydroxy-16α-methyl-20-keto-4,6-pregnadieno[3,2-c]pyrazole 21-acetate (microcrystalline, sterile) | 5.0 |
| Methylparaben, USP | 0.1 |
| Propylparaben, USP | 0.5 |
| Phenyl ethanol | 0.5 |
| Mineral Oil, USP | 179.0 |
| White Petrolatum, USP | 814.9 |

| C. Suspension | mg/ml |
|---|---|
| 2'-phenyl-6-azido-9α-fluoro-11β,17α,21-trihydroxy-16α-methyl-20-keto-4,6-pregnadieno[3,2-c]pyrazole 21-acetate (microcrystalline, sterile) | 5.0 |
| Dibasic Sodium Phosphate USP | 0.25 |
| Monobasic Sodium Phosphate USP | 1.25 |
| Sodium Chloride USP | 6.4 |
| Tween 80 | 0.5 |
| Benzalkonium Chloride USP | 0.1 |
| Disodium Edetate USP | 0.1 |
| Purified Water, USP Distilled q.s. ad | 1.0 ml. |

| D. Suspension | mg/ml |
|---|---|
| 2'-phenyl-6-azido-9α-fluoro-11β,17α,21-trihydroxy-16α-methyl-20-keto-4,6-pregnadieno[3,2-c]pyrazole 21-acetate (microcrystalline, sterile) | 5.0 |
| Gentamicin | 3.0 |
| Dibasic Sodium Phosphate USP | 0.25 |
| Monobasic Sodium Phosphate USP | 1.25 |
| Sodium Chloride USP | 6.4 |
| Tween 80 | 0.5 |
| Benzalkonium Chloride USP | 0.1 |
| Disodium Edetate USP | 0.1 |
| Purified Water USP Distilled q.s. ad | 1.0 ml. |

In above compositions IIA, IIB, IIC, and IID, 2'-phenyl-6-azido-11β,17α,21-trihydroxy-20-keto-4,6-pregnadieno[3,2-c]pyrazole 21-acetate may be used instead of 2'-phenyl-6-azido-9α-fluoro-11β,17α,21-trihydroxy-16α-methyl-20-keto-4,6-pregnadieno[3,2-c]pyrazole 21-acetate.

III. Otic Compositions

| A. | mg/ml |
|---|---|
| 2'-phenyl-6-azido-9α-fluoro-11β,17α,21-trihydroxy-16α-methyl-20-keto-4,6-pregnadieno[3,2-c]pyrazole 21-acetate (microcrystalline, sterile) | 5.0 |
| Disodium Edetate USP | 1.0 |
| Polyvinylpyrrolidone | 30.0 |
| Polysorbate 80, USP | 10.0 |
| Propylene Glycol USP | 100.0 |
| Glycerin USP | 700.0 |
| Purified Water, USP, Distilled, q.s. ad | 1.0 ml. |

| B. | mg/ml |
|---|---|
| 2'-phenyl-6-azido-9α-fluoro-11β,17α,21-trihydroxy-16α-methyl-20-keto-4,6-pregnadieno[3,2-c]pyrazole 21-acetate (microcrystalline, sterile) | 5.0 |
| Neomycin USP micronized | 3.5 |
| Polymyxin B sulfate USP micronized | 10,000 units |
| Disodium Edetate USP | 1.0 |
| Polyvinylpyrrolidone | 30.0 |
| Polysorbate 80 USP | 10.0 |
| Propylene Glycol USP | 100.0 |
| Glycerin USP | 700.0 |
| Purified Water, USP, Distilled q.s. ad | 1.0 |

In above compositions IIIA and IIIB 2'-phenyl-6-azido-11β,17α,21-trihydroxy-20-keto-4,6-pregnadieno[3,2-c]pyrazole- 21-acetate may be used instead of 2'-phenyl-6-azido-9α-fluoro-11β,17α,21-trihydroxy-16α-methyl-20-keto-4,6-pregnadieno[3,2-c]pyrazole 21-acetate.

IV. Oral Compositions

| A. Liquid | mg/ml |
|---|---|
| 2'-phenyl-6-azido-9α-fluoro-11β,17α,21-trihydroxy-16α-methyl-20-keto-4,6-pregnadieno[3,2-c]pyrazole 21-acetate | 0.05 |
| Methylparaben USP | 0.10 |
| Propylparaben USP | 0.02 |
| Citric Acid USP | 3.00 |
| Standard Granulated Sugar, Food Grade | 550.00 |
| FD and C Yellow No. 6 | 0.05 |
| Imitation Flavor | 1.00 |
| Alcohol USP | 5.00 |
| Purified Water USP To Make | 1.00 ml. |

In above composition IVA, there may be used 0.25 mg./ml. of 6-azido-11β,17α,21-trihydroxy-20-keto-4,6-pregnadieno[3,2-c]pyrazole 21-acetate instead of 0.05 mg./ml. of 2'-phenyl-6-azido-9α-fluoro-11β,17α,21-trihydroxy-16α-methyl-20-keto-4,6-pregnadieno[3,2-c]pyrazole 21-acetate.

| B. Tablet Compositions | mg/tablet | |
|---|---|---|
| (1) | 0.3 | 0.15 |
| 2'-phenyl-6-azido-9α-fluoro-11β,17α,21-trihydroxy-16α-methyl-20-keto-4,6-pregnadieno[3,2-c]pyrazole 21-acetate | | |
| Lactose Direct Compression Grade | 74.2 | 74.35 |
| Microcrystalline Cellulose | 10.0 | 10.0 |
| Sodium Lauryl Sulfate, USP | 5.0 | 5.0 |
| Starch Direct Compression Grade | 10.0 | 10.0 |
| Magnesium Stearate | 0.5 | 0.5 |
| | 100.0 | 100.0 |

27 -continued

(2)

| | mg/tablet | |
|---|---|---|
| 2'-phenyl-6-azido-9α-fluoro-11β,17α,21-trihydroxy-16α-methyl-20-keto-4,6-pregnadieno[3,2-c]pyrazole 21-acetate | 0.3 | 0.15 |
| Lactose USP | 79.2 | 79.35 |
| Sodium Lauryl Sulfate, USP | 5.0 | 5.0 |
| Polyvinylpyrrolidone | 5.0 | 5.0 |
| Corn Starch, Food Grade | 10.0 | 10.0 |
| Magnesium Stearate, USP | 0.5 | 0.5 |
| | 100.0 | 100.0 |

(3)

| | | |
|---|---|---|
| 2'-phenyl-6-azido-9α-fluoro-11β,17α,21-trihydroxy-16α-methyl-20-keto-4,6-pregnadieno[3,2-c]pyrazole 21-acetate | 0.3 | 0.15 |
| Lactose USP | 79.2 | 79.35 |
| Sodium Lauryl Sulfate, USP | 5.0 | 5.00 |
| Starch Paste (15% solids) | 5.0 | 5.0 |
| Corn Starch, Food Grade | 10.0 | 10.0 |
| Magnesium Stearate | 0.5 | 0.5 |
| | 100.00 | 100.00 |

C. Capsule Compositions

| | mg/capsule | |
|---|---|---|
| 2'-phenyl-6-azido-9α-fluoro-11β,17α,21-trihydroxy-16α-methyl-20-keto-4,6-pregnadieno[3,2-c]pyrazole 21-acetate | 0.3 | 0.15 |
| Lactose USP | 194.2 | 194.35 |
| Corn Starch, Food Grade | 20.0 | 20.0 |
| Sodium Lauryl Sulfate, USP | 10.0 | 10.0 |
| Magnesium Stearate, USP | 0.5 | 0.5 |
| | 225.00 | 225.00 | in above compositions IVB(1), IVB(2), IVB(3), and IV(C), there may be used 1 mg./tablet or 0.50 mgm./tablet of 2'-phenyl-6-azido-11β,17α,21-trihydroxy-20-keto-4,6-pregnadieno[3,2-c] pyrazole 21-acetate in place of 0.3 mg./tablet or 0.15 mg./tablet, respectively of 2'-phenyl-6-azido-9α-fluoro-11β,17α,21-trihydroxy-16α-methyl-20-keto-4,6-pregnadieno[3,2-c]pyrazole 21-acetate.

V. Topical Compositions

A. Ointment

| | mg/g |
|---|---|
| 2'-phenyl-6-azido-9α-fluoro-11β,17α,21-trihydroxy-16α-methyl-20-keto-4,6-pregnadieno[3,2-c]pyrazole 21-acetate | 0.1 |
| Methylparaben USP | 0.5 |
| Propylparaben USP | 0.1 |
| Mineral Oil USP | 100.0 |
| White Petrolatum USP To Make | 1.0 g. |

B. Ointment

| | |
|---|---|
| 2'-phenyl-6-azido-9α-fluoro-11β,17α,21-trihydroxy-16α-methyl-20-keto-4,6-pregnadieno[3,2-c]pyrazole 21-acetate | 0.1 |
| Stearyl Alcohol USP | 50.0 |
| Polyethylene Glycol 400 USP | 600.0 |
| Polyethylene Glycol 4000 USP To Make | 1.0 g |

C. Cream

| | |
|---|---|
| 2'-phenyl-6-azido-9α-fluoro-11β,17α,21-trihydroxy-16α-methyl-20-keto-4,6-pregnadieno[3,2-c]pyrazole 21-acetate | 0.1 |
| White Petrolatum USP | 150.0 |
| Cetostearyl Alcohol | 72.0 |
| Cetomacrogol 1000 | 22.5 |
| Mineral Oil USP | 60.0 |
| 4-Chloro-m-Cresol | 1.0 |
| Propylene Glycol USP | 50.0 |
| Sodium Biphosphate, Reagent Grade | 3.0 |
| Purified Water USP To Make | 1.0 g. |

28 -continued

D. Cream

| | mg/g |
|---|---|
| 2'-phenyl-6-azido-9α-fluoro-11β,17α,21-trihydroxy-16α-methyl-20-keto-4,6-pregnadieno[3,2-c]pyrazole 21-acetate | 0.1 |
| Stearic Acid USP | 60.0 |
| Glyceryl Monostearate, Pure | 100.0 |
| Propylene Glycol USP | 50.0 |
| Polyoxyethylene Sorbitan Monopalmitate | 50.0 |
| Sorbitol Solution USP | 30.0 |
| Benzyl Alcohol NF | 10.0 |
| Purified Water USP To Make | 1.0 g. |

E. Lotion

| | |
|---|---|
| 2'-phenyl-6-azido-9α-fluoro-11β,17α,21-trihydroxy-16α-methyl-20-keto-4,6-pregnadieno[3,2-c]pyrazole 21-acetate | 0.1 |
| Isopropanol | 400.0 |
| Carbopol 934, P Grade | 3.0 |
| Sodium Hydroxide USP To Adjust to about pH 5 | |
| Purified Water USP To Make | 1.0 g. |

F. Lotion

| | |
|---|---|
| 2'-phenyl-6-azido-9α-fluoro-11β,17α,21-trihydroxy-16α-methyl-20-keto-4,6-pregnadieno[3,2-c]pyrazole 21-acetate | 0.1 |
| Methylparaben USP | 1.5 |
| Glycerin USP | 50.0 |
| Isopropanol | 52.0 |
| Polyethylene Glycol Ether of Fatty Alcohols | 9.3 |
| Diethylene Glycol Monostearate | 6.5 |
| Cetostearyl Alcohol | 6.5 |
| Mineral Oil USP | 19.5 |
| Citric Acid USP To Adjust to about pH 5 | |
| Purified Water USP To Make | 1.0 g. |

In above compositions VA, VB, VC, VD, VE, and VF, there may be used 0.5 mg/g of 2'-phenyl-6-azido-11β,17α,21-trihydroxy-20-keto-4,6-pregnadieno[3,2-c]pyrazole 21-acetate instead of 0.1 mg/g of 2'-phenyl-6-azido-9α-fluoro-11β,17α,21-trihydroxy-16α-methyl-20-keto-4,6-pregnadieno[3,2-c]pyrazole 21-acetate.

PREPARATION 1

Preparation of 2'-Phenyl-9α-Fluoro-11β,17α,21-trihydroxy-16α-Methyl-20-Keto-4,6-Pregnadieno[3,2-c]pyrazole

A.

2-Hydroxymethylene-9α-fluoro-16α-methyl-17α,20;20,21-bis-methylenedioxy-4,6-pregnadiene-11β-ol-3-one To a solution of 9α-fluoro-16α-methyl-17α,20; 20, 21-bis-methylenedioxy-4,6-pregnadiene-11β-ol-3-one (1.58 G.) in a 2:1 mixture of anhydrous tetrahydrofuran/benzene (200 ml.) under nitrogen, add 970 mg. of sodium hydride (51% in mineral oil powder) and 970 mg. of sodium methoxide (previously dried in vacuo at 100°C) and 3 ml. of ethyl formate (freshly distilled). Stir for 2.5 hours, add a saturated aqueous solution of potassium dihydrogen phosphate and distill most of the organic solvent in vacuo. Add water and benzene to the resultant residue, wash the benzene solution with 5% aqueous sodium bicarbonate (3 times), then extract the benzene solution with 2% aqueous sodium hydroxide (3 times). Wash the sodium hydroxide extract with benzene, then acidify with 2% hydrochloric acid. Filter, wash with water and air-dry the resultant precipitate comprising 2-hydroxymethylene-9α-fluoro-16α-methyl-17α,20;20,21-bismethylenedioxy-4,6-pregnadiene-11β-ol-3-one which can be used without further purification for the following procedure in Preparation 1B.

If desired, the compound of this invention may be purified by crystallization from ether/acetone to obtain 2-hydroxymethylene-9α-fluoro-16α-methyl-17α,20;20,21-bismethylenedioxy- 4,6-pregnadiene-11β-ol-3-one as a methanol solvate.

NMR (CDCl$_3$): 0.96 (3H, d), 1.19 (3H), 1.31 (3H), 3.48 (1H), 4.00 (2H), 4.28 (1H, broad), 4.94–5.23 (4H, m), 4.80 (1H), 6.07 (2H, d of d), 7.7 (1H) ppm.

$\lambda_{max}^{methanol}$ 288 mμ (ε17,050);

$\lambda_{max}^{methanol-NaOH}$ 254, 261, 277 (sh), 287, 298 (sh) mμ

B. 2'-Phenyl-9α-fluoro-11β-hydroxy-16α-methyl-17α,,20;20,21-bismethylenedioxy-4,6-pregnadieno[3,2-c]pyrazole To a solution of 1.1 g. of 2-hydroxymethylene-9α-fluoro-16α-methyl-17α,20;20,21-bismethylenedioxy-4,6-pregnadiene-11β-ol-3-one (prepared as described in preparation 1A) in 15 ml. of ethanol under an atmosphere of nitrogen, add 0.6 ml. of phenylhydrazine and heat at reflux temperature under an atmosphere of nitrogen for 1 hour. Distill in vacuo to a residue. Dissolve the residue in ether, wash the ether solution with 2% hydrochloric acid followed by water. Dry the ether solution over sodium sulfate, then concentrate the ether solution to a small volume, chromatograph the ether concentrate over silica gel (2.5 × 25 (m.) eluting with chloroform. Combine the like chloroform eluates as determined by thin layer chromatography and evaporate the combined eluates in vacuo to a residue comprising 2'-phenyl-9α-fluoro-11β-hydroxy-16α-methyl-17α,20;20,21-bismethylenedioxy-4,6-pregnadieno[3,2-c]pyrazole. Further purify by crystallization from acetone/hexane; yield = 539 mg.; M.P. 255°–257°C; [α]$_D^{26°}$ −178.8° (chloroform);

$\lambda_{max}^{methanol}$ 223 mμ (ε10,150), 286 mμ(ε14,600), 314 mμ (ε17,200);

NMR (CDCl$_3$): δ 0.94 (3H,d), 1.18 (3H), 1.27 (3H), 3.96 (2H), 4.25 (1H, br), 4.94–5.22 (4H, m), 5.85 (2H, d of d), 6.23 (1H), 7.37 (1H, broad), 7.46 (5H) ppm.

C. 2'-Phenyl-9α-fluoro-11β,17α,21-trihydroxy-16α-methyl-20-keto-4,6-pregnadieno[3,2-c]pyrazole Dissolve 539 mg. of 2'-phenyl-9α-fluoro-11β-hydroxy-16α-methyl-17α,20:20,21-bismethylenedioxy-4,6-pregnadieno[3,2-c]pyrazole in 60% aqueous formic acid (25 ml.). Heat the solution on a steam bath under an atmosphere of nitrogen for 30 minutes, then concentrate in vacuo to a residue. Dissolve the residue in a mixture of ethyl acetate and ether, wash the organic solution with 10% aqueous sodium bicarbonate, then with water. Concentrate the organic solution in vacuo, then dissolve the residue in a mixture of ethanol (50 ml.) and tetrahydrofuran (25 ml.). Add 3 ml. of 1 N potassium hydroxide, stir under nitrogen for 30 minutes, then add water (200 ml.) and dilute acetic acid until mixture is neutral. Filter, wash with water and air-dry the resultant precipitate comprising 2'-phenyl-9α-fluoro-11β,17α,21-trihydroxy-16α-methyl-20-keto-4,6-pregnadieno[3,2-c]pyrazole. Purify by crystallization from dichloromethane-isopropyl ether (yield 193 mg.); melting point: 260°C, 270°–280°C; [α]$_D^{26°}$ −96.9° (dioxane)

$\lambda_{max}^{methanol}$ 220 mμ (ε13,070), 285 mμ(ε17,800), 313 mμ (ε19,450).

D. 2'-Phenyl-9α-fluoro-11β,17α,21-trihydroxy-16α-methyl-20-keto-4,6-pregnadieno[3,2-c]pyrazole 21-acetate Dissolve 1 g. of 2'-phenyl-9α-fluoro-11β,17α,21-trihydroxy-16α-methyl-20 -keto-4,6-pregnadieno[3,2-c]pyrazole in 10 ml. of pyridine, add 3 ml. of acetic anhydride, and allow the reaction mixture to stand for 5 hours at room temperature. Add the reaction solution to a large volume of water, filter the resultant precipitate wash with water, and chromatograph over 200 g. of silica gel. Elute with chloroform/ethyl acetate (4:1). Combine the eluates and evaporate in vacuo to a residue. Purify the residue by crystallization from ethyl acetate/isopropanol to give 2'-phenyl-9α-fluoro-11β,17α,21-trihydroxy-16α-methyl-20-keto-4,6-pregnadieno[3,2-c]pyrazole 21-acetate; melting point: 275°–282°C; [α]$_D^{26°}$ −55° (chloroform);

$\lambda_{max}^{methanol}$ 220 mμ (ε14,350), 285 mμ (ε19,000), 314 mμ (ε22,400).

PREPARATION 2

2'-Phenyl-11β,17α,21-Trihydroxy-20-Keto-4,6-Pregnadieno[3,2-c]pyrazole 21-acetate

A. 2-Hydroxymethylene-17α,20;20,21-bismethylenedioxy-4,6-pregnadiene-11β-ol-3-one To a solution of 17α,20;20,21-bismethylenedioxy-4,6-pregnadiene-11β-ol-3-one (1005 g.) in benzene (200 ml.) add 2 ml. of ethyl formate (freshly distilled) and 460 mg. of sodium hydride (51% in mineral oil powder) and stir the reaction mixture under an atmosphere of nitrogen for 22.5 hours. Add a saturated aqueous solution of potassium dihydrogen phosphate. Separate the layers and wash the organic layer with 5% aqueous sodium bicarbonate (3 times), then extract with 2% sodium hydroxide solution (3 times). Acidify with 2.5 N hydrochloric acid, then filter, wash with water, and air dry the resultant precipitate comprising 2-hydroxymethylene-17α20;20,21-bismethylenedioxy-4,6-pregnadiene-11G2s-ol-3-one; yield 500 mg. Purify by crystallization from acetone; melting point: 240°–245°C; [α]$_D^{26°}$ −200.3° (chloroform): $\lambda_{max}^{methanol}$ 290 mμ (ε18,550);

$\lambda_{max}^{(methanol-NaOH)}$ 257,263,277 (sh), 289 mμ; NMR (DMSO-d$_6$): δ1.08 (3H), 1.12 (3H), 3.98 (2H,q), 4.22 (1H,broad), 4.88–5.18 (4H, m), 5.63 (1H), 6.21 (2H), 7.91 (1H) ppm.

B. 2'-Phenyl-11β-hydroxy-17α,20;20,21-bismethylenedioxy-4,6-pregnadieno [3,2-c]pyrazole Dissolve 350 mg. of 2-hydroxymethylene-17α,20;20,21-bismethylenedioxy-4,6-pregnadiene-11β-ol-3-one in 50 ml. of ethanol, add 0.5 ml. of phenylhydrazine and heat at reflux temperature under an atmosphere of nitrogen for 2 hours. Concentrate the solution in vacuo and dissolve the resultant residue in ether. Wash the ether solution successively with 1% hydrochloric acid, 5% aqueous sodium hydroxide and water. Dry the ether solution over sodium sulfate and evaporate in vacuo to a residue. Chromatograph the residue on silica gel (10 × 10 cm.) thin layer plates, develop twice with chloroform/ethyl acetate (1:1). Extract the most polar ultraviolet absorbing zone with chloroform/acetone. Evaporate the extracts and purify the residue by crystallization from acetone/isopropyl ether to give 2'-phenyl-11β-hydroxy-17α,20;20,21-bis-methylenedioxy-4,6-pregnadieno[3,2-c]pyrazole; melting point: 245°–250°C; $[\alpha]_D^{26°}$ −155.9° (chloroform);

$\lambda_{max}^{methanol}$ 224 mμ (ε11,400), 283 mμ (ε14,500), 313 mμ (ε16,700); NMR (CDCl$_3$): δ 1.08 (3H), 1.18 (3H), 3.98 (2H), 3.42 (1H,broad), 4.90–5.19 (4H, m), 5.92 (2H, d of d), 6.13 (1H), 7.37 (1H), 7.44 (5H) ppm.

C.

2'-Phenyl-11β,17α,21-trihydroxy-20-keto-4,6-pregnadieno[3,2-c]pyrazole

Prepare a solution of 887 mg. of 2'-phenyl-11β-hydroxy-17α,20;20,21-bismethylenedioxy-4,6-pregnadieno[3,2-c]pyrazole in 60% formic acid (30 ml.), then heat the solution under an atmosphere of nitrogen on a steam bath for 1 hour. Concentrate the solution in vacuo, dissolve the resultant residue in 30 ml. of ethanol, add 4 ml. of 1N aqueous potassium hydroxide and stir under an atmosphere of nitrogen for 1 hour. Neutralize with acetic acid, pour the neutralized solution into water and filter, wash and air-dry the resultant precipitate comprising 2'-phenyl-11β,17α,21-trihydroxy-20-keto-4,6-pregnadieno[3,2-c]pyrazole which is used without further purification in following Preparation 2D.

D.

2'-Phenyl-11β,17α,21-trihydroxy-20-keto-4,6-pregnadieno[3,2-c]pyrazole 21-acetate Dissolve the 2'-phenyl-11β,17α,21-trihydroxy-20-keto-4,6-pregnadieno[3,2-c]pyrazole prepared in Preparation 2C in 2 ml. of pyridine. Add 5 ml. of acetic anhydride and allow the reaction mixture to stand at room temperature for 3 hours. Pour the solution into water, filter, and air-dry the resultant precipitate, then chromatograph the precipitate over silica gel (2.3 × 11 cm.) eluting with dichloromethane/ether (7:3). Combine the like eluates as determined by thin layer chromatography and evaporate to a residue comprising 2'-phenyl-11β,17α,21-trihydroxy-20-keto-4,6-pregnadieno[3,2-c]pyrazole 21-acetate; yield 295 mg. Further purify by crystallization from acetone/hexane; melting point: 235°–240°C; $[\alpha]_D^{26°}$ −6.2° (chloroform);

$\lambda_{max}^{methanol}$ 223 mμ (ε13,050), 288 mμ (ε16,800); 314 mμ (ε20,100).

PREPARATION 3

6-Azido-9α-Fluoro-16α-Methyl-17α,20;20,21-Bismethylenedioxy-4,6-Pregnadiene-3,11-Dione

A.

6β,7β-Dihydroxy-9α-Fluoro-16α-Methyl-17α,20;20,21-Bismethylenedioxy-4-Pregnene-3,11-Dione To 1.74 gm. of 9α-fluoro-16α-methyl-17α,20;20,21-bismethylenedioxy-4,6-pregnadiene-3,11-dione add a solution of 1 gm. osmium tetroxide in 50 ml. of dioxane. Add an additional 30 ml. portion of dioxane and stir the mixture at room temperature for 2 days. Add an additional 0.25 gm. of osmium tetroxide and stir the reaction mixture at room temperature for an additional 2 days. Bubble hydrogen sulphide into the mixture, filter the reaction mixture through Celite, and evaporate the filtrate in vacuo to a residue comprising 6β,7β-dihydroxy-9α-fluoro-16α-methyl-17α,20;20,21-bis-methylenedioxy-4-pregnene-3,11-dione. Purify by chromatography over silica gel eluting with 4:1 methylene chloride/ether. Combine the like fractions as determined by thin layer chromatography and evaporate the combined like fractions in vacuo to a residue. Crystallize the residue from methylene chloride/isopropyl ether to obtain 6β7β-dihydroxy-9α-fluoro-16α-methyl-17α,20;20,21-bismethylenedioxy-4-pregnene-3,11-dione; $[\alpha]_D^{26°}$ = −22° (chloroform);

$\lambda_{max}^{methanol}$ 230 nm (ε−12,700) Mass Spectrum: M$^+$ =466;

NMR: (CHCl$_3$) 0.88 (3H s), 1.01 (3H d); J=6.5 Hz 1.67 (3H s), 3.93 (1H b.s.), 3.98 (2H s), 4.31 (1H t), 5.12 (4H m), and 5.96 (1H s) ppm; IR: 3400, 3350, 1720 and 1660 cm$^{-1}$ (nujol).

B.

6β,7β-Dimethanesulfonyloxy-9α-fluoro-16α-methyl-17α,20;20,21-Bismethylenedioxy-4-Pregnene-3,11-Dione To a solution of 320 mg. of 6β,7β-dihydroxy-9α-fluoro-16α-methyl-17α,20;20,21-bismethylenedioxy-4-pregnene-3,11-dione in 6 ml. of pyridine at 0°C add 0.6 ml. of methanesulfonyl chloride. Allow the reaction mixture to warm to room temperature, stir at room temperature for 3 hours, then pour into water. Separate the resultant precipitate by filtration, wash the precipitate with water, and dissolve in methylene chloride. Dry the solution over magnesium sulfate, filter and evaporate in vacuo to a residue comprising 6β,7β-dimethanesulfonyloxy-9α-fluoro-16α-methyl-17α,20;20,21-bismethylenedioxy-4-pregnene-3,11-dione, which is used without further purification in the procedure of following Preparation 3C.

C.

6-Azido-9α-Fluoro-16α-Methyl-17α,20;20,21-bismethylenedioxy-4,6-Pregnadiene-3,11-Dione To the 6β,7β-dimethanesulfonyloxy-9α-fluoro-16α-methyl-17α,20;20,21-bismethylenedioxy-4-pregnene-3,11-dione prepared in preceding Preparation 3B, in 5 ml. of dimethylformamide add 1.7 gm. of sodium azide and stir at room temperature under an atmosphere of nitrogen in the dark for 24 hours. Pour into water and separate the resultant precipitate by filtration, dry the precipitate in air and chromatograph over silica gel G.F. 254 eluting with chloroform-ethyl acetate (2:1). Combine the like eluates as determined by thin layer chromatography and evaporate the combined eluates to a residue comprising 6-azido-9α-fluoro-16α-methyl-17α,20;20,21-bismethylenedioxy-4,6-pregnadiene-3,11-dione;

$\lambda_{max}^{methanol}$ 251 and 300 nm; NMR: (CHCl$_3$) 0.92 (3H s), 1.03 (3H d); J=7.0Hz, 1.38 (3Hs), 4.0 (2H s), 5.11 (4H m), 5.46 (1H d); J=2.0Hz and 6.23 (1H s) ppm. IR: 2100 cm$^{-1}$, 1725, 1670, 1610 and 1590 cm$^{-1}$ (CH$_2$Cl$_2$)

PREPARATION 4

6-Azido-9α-Fluoro-16α-Methyl-17α,20;20,21-Bismethylenedioxy-4,6-Pregnadiene-11β-ol-3-one

A.
6β,7β-Dihydroxy-9α-Fluoro-16α-Methyl-17α,20;20,21-Bismethylenedioxy-4-Pregnene-11β-ol-3-one To a solution of 6 gm. of osmium tetroxide in 200 ml. of dioxane add a solution of 9.53 gm. of 9α-fluoro-16α-methyl-17α,20;20,21-bismethylenedioxy-4,6-pregnadiene-11β-ol-3-one in 20 ml. of pyridine and 200 ml. of dioxane. Stir the reaction mixture at room temperature in the dark for 3 days then bubble hydrogen sulphide through the reaction for 10 minutes. Filter the reaction mixture through Celite then allow the filtrate to evaporate at room temperature to a residue comprising 6β,7β-dihydroxy-9α-fluoro-16α-methyl-17α,20;20,21-bismethylenedioxy-4-pregnene-11β-ol-3-one. Purify by chromatographying over Florisil, eluting with ether. Evaporate the combined, like eluates to a residue, crystallize residue from acetone-hexane to give 6β,7β-dihydroxy-9α-fluoro-16α-methyl-17α,20;20,21-bismethylenedioxy-4-pregnene-11β-ol-3-one.

(Yield=1.84 gms.):
UV (MeOH) λmax 238 nm ($\epsilon$=11,700); m.p. 245°–250°C; Mass Spectrum M$^+$= 468; NMR (DMSO) 0.88 (3H $d$) J=6.5Hz, 1.12 (3H $s$), 1.62 (3H $s$), 3.85–4.53 (6H unresolved), 4.85–5.30 (6H unresolved), 5.87 ppm (1H $s$); $[\alpha]_D^{26}$ = −42.2° (dioxane); I/R (nujol) 3400, 3340, 1700, 1650, 1610 cm$^{-1}$.

B. 6β,6β-Dimethanesulfonyloxy-9α-Fluoro-16α-Methyl-17α,20;20,21-Bismethylenedioxy-4-Pregnene-11β-ol-3-one.

To a solution of 1.84 gm. of 6β,7β-dihydroxy-9α-fluoro-16α-methyl-17α,20;20,21-bismethylenedioxy-4-pregnene-11β-ol-3-one in 25 ml. of pyridine at 0°C, add 2 ml. of methanesulfonyl chloride, allow the reaction mixture to warm to room temperature, stir at room temperature for 3 hours, then pour into water. Separate the resultant precipitate by filtration, wash the precipitate with water and dissolve in methylene chloride. Dry the methylene chloride solution over magnesium sulfate and evaporate in vacuo to a residue comprising 6β,7β-dimethanesulfonyloxy-9α-fluoro-16α-methyl-17α,20;20,21-bismethylenedioxy-4-pregnene-11β-ol-3-one, which is used without further purification in the following Preparation 4C.

C.
6-Azido-9α-Fluoro-16α-Methyl-17α,20;20,21-Bismethylenedioxy-4,6-pregnadiene-11β-ol-3-one To the 6β,7β-dimethanesulfonyloxy-9α-fluoro-16α-methyl-17α,20;20,21-bismethylenedioxy-4-pregnene-11β-ol-3-one prepared in above Preparation 4B in 15 ml. of dimethyl formamide add 8 gm. of sodium azide. Stir the reaction mixture at room temperature under an atmosphere of nitrogen in the dark for 24 hours, then pour into water. Separate the resultant precipitate by filtration, dry the precipitate in air then chromatograph over silica gel G.F. 254 eluting with chloroform/ethylacetate (2:1). Combine the like fractions as determined by thin layer chromatography and evaporate the combined eluates to a residue comprising 6-azido-9α-fluoro-16α-methyl-17α,20;20,21-bismethylenedioxy-4,6-pregnadiene-11β-ol-3-one.

(Yield=485 mg); m.p. 225°–235°C; U.V. (MeOH) λmax 250 ($\epsilon$=13,600) and 298 nm ($\epsilon$=12,200); $[\alpha]_D^{26}$ (CHCl$_3$) + 29°; NMR (CDCl$_3$) 0.99 (3H $d$); J=6.5Hz, 1.22 (3H $s$), 1.47 (3H $s$), 4.0 (2H $s$), 5.10 (4H $m$), 5.55 (1H $d$); J=2Hz 6.17 ppm (1H $s$); I/R (nujol) 3350, 2100, 1640 and 1620 cm$^{-1}$.

EXAMPLE 1

2′-Phenyl-6-Azido-9α-Fluoro-11β,17α,21-Trihydroxy-16α-Methyl-20-Keto-4,6-Pregnadieno[3,2-c]Pyrazole 21-Acetate

A. 2′-Phenyl-6-Azido-7-Bromo-9α-Fluoro-11β,17α,21-Trihydroxy-16α-Methyl-20-keto-4-Pregneno[3,2-c]Pyrazole 21-acetate To a suspension of sodium azide (163 mg., 2.5 mmoles) in dichloromethane (20 ml.) add dropwise 3 N hydrochloric acid (0.8 ml., 1.1 equivalents). Add the resulting mixture containing hydrazoic acid to a solution of 2′-phenyl-9α-fluoro-11β,17α,21-trihydroxy-16α-methyl-20-keto-4,6-pregnadieno[3,2-c]pyrazole 21-acetate (543.6 mg.,1 mmole) and N-bromosuccinimide (196 mg., 1.1 mmole) in a mixture of dichloromethane (30 ml.) and tertiary butanol (0.1 ml.). Stir the reaction mixture at room temperature for 40 minutes then pour into water and extract with dichloromethane. Wash the combined organic extract successively with 5% aqueous sodium thiosulfate, 5% sodium bicarbonate, then water. Dry the organic solution over sodium sulfate and evaporate in vacuo to a residue comprising 2′-phenyl-6-azido-7-bromo-9α-fluoro-11β,17α,21-trihydroxy-16α-methyl-20-keto-4-pregneno[3,2-c]pyrazole 21-acetate which is used without further purification in Example 1 B following.

B.
2′-Phenyl-6-Azido-9α-Fluoro-11β,17α,21-Trihydroxy-16α-Methyl-20-Keto-4,6-Pregnadieno[3,2-c]Pyrazole 21-Acetate Dissolve the 2′-phenyl-6-azido-7-bromo-9α-fluoro-11β,17α,21-trihydroxy-16α-methyl-20-keto-4-pregneno[3,2-c]pyrazole (prepared as described in above Example 1A) in acetonitrile (40 ml.). Add tetramethylammonium fluoride pentahydrate (1 g.) and stir the reaction mixture under an atmosphere of nitrogen at room temperature for 5 days. Remove the solids by filtration, then evaporate the solution in vacuo to a residue. Partition the residue between dichloromethane and water, separate the organic extract, wash the organic extract with water, dry over magnesium sulfate and evaporate in vacuo to a residue. Chromatograph the residue over silica gel with gradient elution with petroleum ether/ether 7:3→4:6. Combine the like eluates as determined by thin layer chromatography and evaporate the combined eluates to a residue comprising 2′-phenyl-6-azido-9α-fluoro-11β,17α,21-trihydroxy-16α-methyl-20 keto-4,6-pregnadieno[3,2-c]pyrazole 21-acetate; yield=182 mg. Purify by crystallization from ether/petroleum ether; yield=132 mg. of 2′-phenyl-6-azido-9α -fluoro-11β,17α,21-trihydroxy-16α-methyl-20 keto-4,6-pregnadieno[3,2-c]pyrazole 21-acetate; m.p. =230°C (dec.); $[\alpha]_D^{26°}$ + 22.7° (chloroform);
$\lambda_{max}^{methanol}$ 222 mμ ($\epsilon$18,130), 290 mμ(sh) ($\epsilon$22,380), 317 mμ ($\epsilon$24,680);

NMR (DMSO-d$_6$): δ0.87 (3H, d) 0.98 (3H), 1.27 (3H), 2.13 (3H), 4.97 (2H, q), 5.38 (1H), 6.66 (1H), 7.55 (5H), 7.63 (1H), ppm.

C. Other
2′-Phenyl-6-Azido-9α-Halogeno-17α,21-Dihydroxy-20-Keto-4,6-Pregnadieno[3,2-c]Pyrazoles 1. In a manner similar to that described in Example 1A or in Example 2A, treat each of the following 6-unsubstituted-9α-halogeno-4,6-pregnadieno[3,2-c]pyrazoles with hydrazoic acid in dichloromethane and by N-bromosuccinimide in dichloromethane and tertiary butanol:

1. 2′-phenyl-9α-fluoro-11β,17α,21-trihydroxy-16β-methyl-20-keto-4,6-pregnadiono[3,2-c]pyrazole 21-acetate,
2. 2′-phenyl-9α-fluoro-11β,17α,21-trihydroxy-20-keto-4,6-pregnadieno[3,2-c]pyrazole 21-acetate,
3. 2′-phenyl-9α-chloro-11β,17α,21-trihydroxy-16α-methyl-20-keto-4,6-pregnadieno[3,2-c]pyrazole 21-acetate,
4. 2′-phenyl-9α-chloro-11β,17α,21-trihydroxy-16β-methyl-20-keto-4,6-pregnadieno[3,2-c]pyrazole 21-acetate,
5. 2′-phenyl-9α-chloro-11β,17α,21-trihydroxy-20-keto-4,6-pregnadieno[3,2-c]pyrazole 21-acetate,
6. 2′-phenyl-9α-bromo-11β,17α,21-trihydroxy-16α-methyl-20-keto-4,6-pregnadieno[3,2-c]pyrazole 21-acetate,
7. 2′-phenyl-9α-bromo-11β,17α,21-trihydroxy-16β-methyl-20-keto-4,6-pregnadieno[3,2-c]pyrazole 21-acetate,
8. 2′-phenyl-9α-bromo-11β,17α,21-trihydroxy-20-keto-4,6-pregnadieno[3,2-c]pyrazole 21-acetate,
9. 2′-phenyl-9α-fluoro-11,20-diketo-16α-methyl-17α,21-dihydroxy-4,6-pregnadieno[3,2-c]pyrazole 21-acetate,
10. 2′-phenyl-9α-fluoro-11,20-diketo-16β-methyl-17α,21-dihydroxy-4,6-pregnadieno[3,2-c]pyrazole 21-acetate,
11. 2′-phenyl-9α-fluoro-11,20-diketo-17α,21-dihydroxy-4,6-pregnadieno[3,2-c]pyrazole 21-acetate,
12. 2′-phenyl-9α-chloro-11,20-diketo-16α-methyl-17α,21-dihydroxy-4,6-pregnadieno[3,2-c]pyrazole 21-acetate,
13. 2′-phenyl-9α-chloro-11,20-diketo-16β-methyl-17α,21-dihydroxy-4,6-pregnadieno[3,2-c]pyrazole 21-acetate,
14. 2′-phenyl-9α-chloro-11,20-diketo-17α,21-dihydroxy-4,6-pregnadieno[3,2-c]pyrazole 21-acetate,
15. 2′-phenyl-9α-bromo-11,20-diketo-16α-methyl-17α,21-dihydroxy-4,6-pregnadieno[3,2-c]pyrazole 21acetate,
16. 2′-phenyl-9α-bromo-11,20-diketo-16β-methyl-17β,21-dihydroxy-4,6-pregnadieno[3,2-c]pyrazole 21-acetate,
17. 2′-phenyl-9α-bromo-11,20-diketo-17α,21-dihydroxy-4,6-pregnadieno[3,2-c]pyrazole 21-acetate.

Isolate and purify each of the resultant products in a manner similar to that described in Example 1A or 1B to obtain, respectively, 1. 2′-phenyl-6-azido-7-bromo-9α-fluoro-11β,17α,21-trihydroxy-16β-methyl-20-keto-4-pregneno[3,2-c]pyrazole 21acetate,
2. 2′-phenyl-6-azido-7-bromo-9α-fluoro-11β,17α,21-trihydroxy-20-keto-4-pregneno[3,2-c]pyrazole 21-acetate,
3. 2′-phenyl-6-azido-7-bromo-9α-chloro-11β,17α,21-trihydroxy-16α-methyl-20-keto-4-pregneno[3,2-c]pyrazole 21-acetate,
4. 2′-phenyl-6-azido-7-bromo-9α-chloro-11β,17α,21-trihydroxy-16β-methyl-20-keto-4-pregneno[3,2-C]pyrazole 21-acetate,
5. 2′-phenyl-6-azido-7-bromo-9α-chloro-11β,17α,21-trihydroxy-20-keto-4-pregneno[3,2-c]pyrazole 21-acetate,
6. 2′-phenyl-6-azido-7,9α-dibromo-11β,17α,21-trihydroxy-16α-methyl-20-keto-4-pregneno[3,2-c]pyrazole 21-acetate,
7. 2′-phenyl-6-azido-7,9α-dibromo-11β,17α,21-trihydroxy-16β-methyl-20-keto-4-pregneno[3,2-c]pyrazole 21-acetate,
8. 2′-phenyl-6-azido-7,9α-dibromo-11β,17α,21-trihydroxy-20-keto-4-pregneno[3,2-c]pyrazole 21-acetate,
9. 2′-phenyl-6-azido-7-bromo-9α-fluoro-11,20-diketo-17α,21-dihydroxy-16α-methyl-4-pregneno[3,2-c]pyrazole 21-acetate,
10. 2′-phenyl-6-azido-7-bromo-9α-fluoro-11,20-diketo-17α,21-dihydroxy-16β-methyl-4-pregneno[3,2-c]pyrazole 21-acetate,
11. 2′-phenyl-6-azido-7-bromo-9α-fluoro-11,20-diketo-17,21-dihydroxy-4-pregneno[3,2-c]pyrazole 21-acetate,
12. 2′-phenyl-6-azido-7-bromo-9α-chloro-11,20-diketo-16α-methyl-17α,21-dihydroxy-4-pregneno[3,2-c]pyrazole 21-acetate,
13. 2′-phenyl-6-azido-7-bromo-9α-chloro-11,20-diketo-16β-methyl-17α,21-dihydroxy-4-pregneno[3,2-c]pyrazole 21-acetate,
14. 2′-phenyl-6-azido-7-bromo-9α-chloro-11,20-diketo-17α,21-dihydroxy-4-pregneno[3,2-c]pyrazole 21acetate,
15. 2′-phenyl-6-azido-7,9α-dibromo-11,20-diketo-16α-methyl-17α,21-dihydroxy-4-pregneno[3,2-c]pyrazole 21-acetate,
16. 2′-phenyl-6-azido-7,9α-dibromo-11,20-diketo-16β-methyl-17α,21-dihydroxy-4-pregneno[3,2-c]pyrazole 21-acetate,
17. 2′-phenyl-6-azido-7,9α-dibromo-11,20-diketo-17α,21-dihydroxy-4-pregneno[3,2-c]pyrazole 21-acetate.

2. In a manner similar to that described in above Example 1B treat each of the 6-azido-7-bromo-4-pregneno[3,2-c]pyrazoles prepared in above Example 1C(1) with tetramethylammoniumfluoride in acetonitrile. Isolate and purify each of the resultant products to obtain, respectively, 1. 2′-phenyl-6-azido-9α-fluoro-11β,17α,21-trihydroxy-16β-methyl-20-keto-4,6-pregnadieno[3,2-c]pyrazole 21-acetate.
2. 2′-phenyl-6-azido-9α-fluoro-11β,17α,21-trihydroxy-20-keto-4,6-pregnadieno[3,2-c]pyrazole 21-acetate,
3. 2′-phenyl-6-azido-9α-chloro-11β,17α,21-trihydroxy-16α-methyl-20-keto-4,6-pregnadieno[3,2-c]pyrazole 21-acetate,
4. 2′-phenyl-6-azido-9α-chloro-11β,17α,21-trihydroxy-16β-methyl-20-keto-4,6-pregnadieno[3,2-c]pyrazole 21-acetate, 5. 2'-phenyl-6-azido-9α-chloro-11β,17α,21-trihydroxy-20-keto-4,6-pregnadieno[3,2-c]pyrazole 21-acetate,
6. 2'-phenyl-6-azido-9α-bromo-11β,17α,21-trihydroxy-16α-methyl-20-keto-4,6-pregnadieno[3,2-c]pyrazole 21-acetate,
7. 2'-phenyl-6-azido-9α-bromo-11β,17α,21-trihydroxy-16β-methyl-20-keto-4,6-pregnadieno[3,2-c]pyrazole 21-acetate,
8. 2'-phenyl-6-azido-9α-bromo-11β,17α,21-trihydroxy-20-keto-4,6-pregnadieno[3,2-c]pyrazole 21-acetate,
9. 2'-phenyl-6-azido-9α-fluoro-11,20-diketo-16α-methyl-17α,21-dihydroxy-4,6-pregnadieno[3,2-c]pyrazole 21-acetate,
10. 2'-phenyl-6-azido-9α-fluoro-11,20-diketo-16β-methyl-17α,21-dihydroxy-4,6-pregnadieno[3,2-c]pyrazole 21-acetate,
11. 2'-phenyl-6-azido-9α-fluoro-11,20-diketo-17α21-dihydroxy-4,6-pregnadieno[3,2-c]pyrazole 21-acetate,
12. 2'-phenyl-6-azido-9α-chloro-11,20-diketo-16α-methyl-17α,21-dihydroxy-4,6-pregnadieno[3,2-c]pyrazole 21-acetate,
13. 2'-phenyl-6-azido-9α-chloro-11,20-diketo-16β-methyl-17α,21-dihydroxy-4,6-pregnadieno[3,2-c]pyrazole 21-acetate,
14. 2'-phenyl-6-azido-9α-chloro-11,20-diketo-17α,21-dihydroxy-4,6-pregnadieno[3,2-c]pyrazole 21-acetate,
15. 2'-phenyl-6-azido-9α-bromo-11,20-diketo-16α-methyl-17α,21-dihydroxy-4,6-pregnadieno[3,2-c]pyrazole 21-acetate,
16. 2'-phenyl-6-azido-9α-bromo-11,20-diketo-16β-methyl-17α,21-dihydroxy-4,6-pregnadieno[3,2-c]pyrazole 21-acetate,
17. 2'-phenyl-6-azido-9α-bromo-11,20-diketo-17α,21-dihydroxy-4,6-pregnadieno[3,2-c]pyrazole 21-acetate.

EXAMPLE 2

2'-Phenyl-6-Azido-11β,17α,21-Trihydroxy-20-Keto-4,6-Pregnadieno/3.2-c/pyrazole 21-Acetate 2'-Phenyl-6-azido-7-bromo-11β,17α,21-trihydroxy-20-keto-4-pregneno/3,2-c/pyrazole 21-acetate Prepare a solution of hydrazoic acid in dichloromethane by adding sodium azide (65 mg., 1mmole) to 1 N hydrochloric acid (1 ml., 1 mmole), then extracting with dichloromethane (12 ml.). Add the freshly prepared solution of hydrazoic acid in dichloromethane to a solution of 2'-phenyl-11β,17α,21-trihydroxy-20-keto-4,6-pregnadieno[3,2-c]pyrazole 21-acetate (251 mg., 0.5 mmoles) and N-bromosuccinimide(100 mg., 0.55 mmoles) in dichloromethane (30 ml.) containing 2 drops of tertiary butanol. Stir at room temperature under an atmosphere of nitrogen for 2 ¼ hours. Evaporate the solvent in vacuo to a residue comprising 2'-phenyl-6-azido-7-bromo-11β,17α,21-trihydroxy-20-keto-4-pregneno[3,2-c]-pyrazole 21-acetate which is used without further purification in the procedure of Example 2B following.

2'-Phenyl-6-azido-11β,17α,21-trihydroxy-20-keto-4,6-pregnadieno/3,2-c/pyrazole 21-acetate Dissolve the 2'-phenyl-6-azido-7-bromo-11β,17α,21-trihydroxy-20-keto-4-pregneno[3,2-c]pyrazole 21-acetate prepared in above Example 2A in acetonitrile (10 ml.), add tetramethylammonium fluoride pentahydrate (500 mg.) and stir under an atmosphere of nitrogen for 5 days at room temperature. Pour the reaction mixture into water, extract the aqueous mixture with ether, combine the ether extracts, wash the combined ether extracts with water, dry the ether extracts over magnesium sulfate, filter and evaporate in vacuo to a residue. Chromatograph the residue over silica gel using gradient elution with petroleum ether/ether (7:3 → 4:6). Combine the like eluates as determined by thin layer chromatography and evaporate the combined eluates in vacuo to a residue comprising 2'-phenyl-6-azido-11β,17α,21-trihydroxy-20-keto-4,6-pregnadieno[3,2-c]pyrazole 21-acetate;

$\lambda_{max}^{methanol}$ 223 mμ, 228 mμ, 319 mμ; Mass Spectrum: M+ 543; I.R. (methylene chloride) 2110, 1748, 1725, 1600, 1275 cm$^{-1}$.

C. Other

2'-Phenyl-6-azido-17α,21-dihydroxy-20-keto-4,6-pregnadieno/3,2-c/pyrazoles

1. In a manner similar to that described in Example 2A treat each of the following 2'-phenyl-4,6-pregnadieno[3,2-c]-pyrazoles with hydrazoic acid in dichloromethane and N-bromosuccinimide in the presence of tertiary butanol:

1. 2'-phenyl-11,20-diketo-17α,21-dihydroxy-4,6-pregnadieno[3,2-c]pyrazole 21-acetate,
2. 2'-phenyl-11β,17α, 21-trihydroxy-16α-methyl-20-keto-4,6-pregnadieno[3,2-c]pyrazole 21-acetate,
3. 2'-phenyl-11β,17α,21-trihydroxy-16β-methyl-20-keto-4,6-pregnadieno[3,2-c]pyrazole 21-acetate,
4. 2'-phenyl-11,20-diketo-16α-methyl-17α,21-dihydroxy-4,6-pregnadieno[3,2-c]pyrazole 21-acetate.
5. 2'-phenyl-11,20-diketo-16β-methyl-17α,21-dihydroxy-4,6-pregnadieno[3,2-c]pyrazole 21-acetate.

Isolate and purify each of the resultant products in a manner similar to that described in Example 2A to obtain, respectively.

1. 2'-phenyl-6-azido-7-bromo-11,20-diketo-17α,21-dihydroxy-4-pregneno[3,2-c]pyrazole 21-acetate,
2. 2'-phenyl-6-azido-7-bromo-11β,17α,21-trihydroxy-16α-methyl-20-keto-4-pregneno[3,2-c]pyrazole 21-acetate,
3. 2'-phenyl-6-azido-7-bromo-11β,17α,21-trihydroxy-16β-methyl-20-keto-4-pregneno[3,2-c]pyrazole 21-acetate,
4. 2'-phenyl-6-azido-7-bromo-11,20-diketo-16α-methyl-17α,21-dihydroxy-4-pregneno[3,2-c]pyrazole 21-acetate,
5. 2'-phenyl-6-azido-7-bromo-11,20-diketo-16β-methyl-17α, 21-dihydroxy-4-pregneno [3,2-c]pyrazole 21-acetate.

2. In a manner similar to that described in Examples 2B treat each of the 2'-phenyl-6-azido-7bromo-4-pregneno[3,2-c]-pyrazoles prepared in Example 2C(1) with tetramethylammoniumfluoride in acetonitrile and isolate and purify each of the resultant products to obtain, respectively, 1. 2'-phenyl-6-azido-11,20-diketo-17α,21-dihydroxy-4,6-pregnadieno[3,2-c]pyrazole 21-acetate,
2. 2'-phenyl-6-azido-11β,17α,21-trihydroxy-16α-methyl-20-keto-4,6-pregnadieno[3,2-c]pyrazole 21-acetate,
3. 2'-phenyl-6-azido-11β,17α,21-trihydroxy-16β-methyl-20-keto-4,6-pregnadieno[3,2-c]pyrazole 21-acetate,
4. 2'-phenyl-6-azido-11,20-diketo-16α-methyl-17α,21-dihydroxy-4,6pregnadieno[3,2-c]pyrazole 21-acetate,
5. 2'-phenyl-6-azido-11,20-diketo-16β-methyl-17α,21-dihydroxy-4,6-pregnadieno[3,2-c]pyrazole 21-acetate.

EXAMPLE 3

2'-Phenyl-6-Azido-9α-Fluoro-11,20-Diketo-16α-Methyl-17α,21-Dihydroxy-4,6-Pregnadieno/3,2-c/Pyrazole-21-Acetate

A.

2-Hydroxymethylene-6-Azido-9α-Fluoro-16α-Methyl-17α,20;20,21-Bismethylenedioxy-4,6-Pregnadiene-3,11-Dione Dissolve 110 mg. of 6-azido-9α-fluoro-16α-methyl-17α,20; 20,21-bismethylenedioxy-4,6-pregnadiene-3,11-dione in 15 ml. of benzene, then remove 10 ml. of the benzene by distillation. Cool the residue in an ice bath. Then, under an atmosphere of nitrogen, add 55 mg. of sodium hydride (50% dispersion in mineral oil) and 50 mg. of sodium methoxide followed by 0.2 ml. of freshly distilled ethyl formate. Stir the reaction mixture for 2 hours slowly allowing the mixture to warm to room temperature, then add an aqueous solution of potassium dihydrogen phosphate. Extract the reaction mixture with benzene, wash the combined benzene extracts twice with dilute aqueous sodium bicarbonate solution, then extract with dilute aqueous sodium hydroxide solution. Extract the resulting sodium hydroxide solution with benzene then acidify with 2% hydrochloric acid. Extract the acidified aqueous solution with benzene. Wash the combined benzene extracts with water, dry over magnesium sulphate and evaporate to a residue comprising 2-hydroxymethylene-6-azido-9α-fluoro-16α-methyl-17α,20;20,21-bismethylenedioxy-4,6-pregnadiene-3,11-dione;

UV (MeOH), λmax. 261 nm, (ε12,600); 296 nm (ε8,700) and 390 nm, (ε5,200).

NMR (CDCl₃) 0.91 (3H s); 1.05 (3H d); J=7.5Hz, 1.25 (3H s), 4.0 (2H s), 5.13 (4H m), 5.44 (1H s), 6.35 (1H s) and 8.0 (1H s) ppm.

B.

2'-Phenyl-6-azido-9α-fluoro-11-keto-16α-methyl-17α,20; 20,21-Bismethylenedioxy-4,6-pregnadieno/3,2-c /pyrazole To a solution of 55 mg. of 2-hydroxymethylene-9α-fluoro-16α-methyl-17α,20;20,21-bismethylenedioxy-4,6-pregnadiene-3,11-dione in 2 ml. of methanol add 3 drops of phenylhydrazine. Heat the mixture on a steam bath under an atmosphere of nitrogen for 30 minutes, cool and pour into water. Separate the resultant precipitate by filtration, wash the precipitate with water, dry, then chromatograph on a preparative plate of silica gel using ethyl acetate-hexane (1:1). Identify each of the bands by ultraviolet spectrum, then extract with ethyl acetate the band exhibiting the ultraviolet spectrum of the desired product. Combine the ethylacetate extracts and evaporate to a residue comprising 2'-phenyl-6-azido-9α-fluoro-11-keto-16α-methyl-17α,20;20,21-bismethylenedioxy-4,6-pregnadieno[3,2-c]pyrazole;

Mass Spectrum M⁺ 573; UV $\lambda_{max}^{methanol}$ 222, 285 sh, and 315 nm; IR 2100 cm⁻¹(methylene chloride).

C.

2'-Phenyl-6-Azido-9α-Fluoro-11,20-Diketo-16α-Methyl-17α,21-Dihydroxy-4,6-Pregnadieno/3,2-c/Pyrazole 21-Acetate 1. To a solution of 100 mg. of 2'-phenyl-6-azido-9α-fluoro-11-keto-16α-methyl-17α,20;20,21-bismethylenedioxy-4,6-pregnadieno-[3,2-c]pyrazole in 25 ml. of anhydrous methylene chloride, add 120 mg. (2.1 equivalents) of triphenylcarbenium tetrafluoroborate. Allow the reaction mixture to stand at room temperature for 16 hours. Wash the reaction mixture with 10% aqueous sodium bicarbonate, then with water and dry the solution over magnesium sulfate. Evaporate the methylene chloride and chromatograph the resultant residue over silica gel eluting with ethyl ether. Combine the like eluates as determined by thin layer chromatography and evaporate the combined eluates to a residue comprising 2'-phenyl-6-azido-9α-fluoro-11,20-diketo-16α-methyl-17α-21-dihydroxy-4,6-pregnadieno[3,2-c]pyrazole (yield=35 mg.). Re-esterify by treating the foregoing product with 0.5 ml. acetic anhydride in 0.5 ml. of pyridine and allowing the mixture to stand overnight at room temperature. Pour the reaction mixture into dilute hydrochloric acid, filter off the resultant precipitate, wash with water then dry to give 2'-phenyl-6-azido-9α-fluoro-11,20-diketo-16α-methyl-17α,21-dihydroxy-4,6-pregnadieneo[3,2-c] pyrazole 21-acetate.

2. Alternatively, the compound of this example is prepared as follows:

Add 3 ml. of 60% aqueous formic acid to 98 mg. of 2'-phenyl-6-azido-9α-fluoro-11keto-16α-methyl-17α,20;20,21-bismethylenedioxy-4,6-pregnadieno[3,2-c]pyrazole. Heat the solution on a steam bath under nitrogen for 30 minutes. Concentrate the solution in vacuo, dissolve the resultant residue in ethyl acetate, wash with 10% aqueous sodium bicarbonate, then with water. Evaporate the ethyl acetate in vacuo, dissolve the resultant residue in a mixture of 5.0 ml. of ethanol and 1.0 ml. of 1 N aqueous potassium hydroxide. Stir under nitrogen at room temperature for 30 minutes, add 100 ml. of water, acidify with dilute acetic acid, then separate the resultant precipitate by filtration, wash with water, and air dry to give 2'-phenyl-6-azido-9α-fluoro-11,20-diketo-16α-methyl-17α,21-dihydroxy-4,6-pregnadieno[3,2-c]-pyrazole. Purify by chromatographing on Florisil eluting with ether-petroleum ether. Re-esterify in the manner described in Example 3C(1).

EXAMPLE 4

Alternate Procedure for the Preparation of 2'-Phenyl-6-Azido-9α-Fluoro-11β,17α,21-Trihydroxy-16α-Methyl-20-Keto-4,6-Pregnadieno/3,2-c/Pyrazole 21-Acetate

A.

2-Hydroxymethylene-6-Azido-9α-Fluoro-16α-Methyl-17α,20;20,21-Bismethylenedioxy-4,6-Pregnadiene-11β-ol-3-one To a solution of 480 mg. of 6-azido-9α-fluoro-16α-methyl-17α,20;20,21-bismethylenedioxy-4,6-pregnadiene-11β-ol-3-one in 25 ml. of dry benzene at 0°C under an atmosphere of nitrogen, add 246 mg. of sodium hydride (50% dispersion in mineral oil) and 30 mg. of sodium methoxide followed by 1.0 ml. of freshly distilled ethyl formate. Stir the reaction mixture overnight allowing it to slowly warm to room temperature. Add a saturated solution of potassium dihydrogen phosphate, extract the mixture with benzene, wash the combined benzene extracts twice with 2% sodium bicarbonate solution, then with 2% sodium hydroxide solution. Wash the sodium hydroxide extracts with benzene, acidify with 2% hydrochloric acid, then re-extract with benzene. Wash the combined benzene extracts with water, dry over magnesium sulfate and evaporate in vacuo to a residue comprising 2-hydroxymethylene-6-azido-9αfluoro-16α-methyl-17α,20;20,21-bismethylenedioxy-4,6-pregnadiene-11β-ol-3-one, (Yield 400 mg.); NMR (CDCl$_3$) 1.00 (3H d), J=6.5Hz, 1.21 (3H s), 1.33 (3H s), 4.0 (2H s), 4.28 (1H unresolved), 5.08 (4H m), 5.55 (1H d) J=2.5Hz, 6.27 (1H s), 7.91 ppm (1H s); Mass Spectrum: M$^+$ 503; I/R (nujol) 3400, 2100 and 1640 cm$^{-1}$; U.V. (MeOH) λmax 260 (ϵ12,300) 298 nm (ϵ9,400).

B.

2'-Phenyl-6-Azido-9αFluoro-11β-Hydroxy-16α-Methyl-17α,20;20,21-Bismethylenedioxy-4,6-Pregnadieno/3,2-c/Pyrazole To a solution of the 400 mg. of 2-hydroxymethylene-6-azido-9α-fluoro-16α-methyl-17α,20;20,21-bismethylenedioxy-4,6-pregnadiene-11β-ol-3-one in 10 ml. of ethanol, add 1.0 ml. of phenylhydrazine Heat the mixture on a stream bath under an atmosphere of nitrogen for 30 minutes, cool and pour into water. Isolate the resultant precipitate by filtration, wash and dry, then chromatograph over silica gel eluting with chloroform. Combine the like eluates and evaporate in vacuo to a residue comprising 2'-phenyl-6-azido-9α-fluoro-11β-hydroxy-16α-methyl-17α,20;21-bismethylenedioxy-4,6-pregnadieno[3,2-c]pyrazole. (Yield 138 mg.). Purify by crystallization from ether.

(Yield 40 mg.); M.P. 230°–237°c; [α]$_D^{26}$ (CHCl$_3$) −73.1°; Mass Spectrum: M.$^+$ = 575; IR (nujol) 3300, 2100, 1600 and 1510 cm$^{-1}$; UV (MeOH) λmax 224 (ϵ=12,800), 295 sh (ϵ=16,500) and 318 nm (ϵ=19,000); NMR (CDCl$_3$) 1.00 (3H d) J=7Hz, 1.23 ( 3H s), 1.30 (3H s), 4.00 (2H s), 4.32 (1H bs), 5.08 (4H m), 5.26 (1H s), 6.78 (1H s), and 7.48 ppm (6H s).

C.

2'-Phenyl-6-Azido-9α-Fluoro-11β,17α,21-Trihydroxy-16α-Methyl-20-Keto-4,6-Pregnadieno/3,2-c/Pyrazole 21-Acetate Treat 2'-phenyl-6-azido-9α-fluoro-11β-hydroxy-16α-methyl-17α,20;20,21-bismethylenedioxy-4,6-pregnadieno[3,2-c]pyrazole in a manner similar to that described in Example 3C(1) or 3C (2) and isolate the resultant product as described to obtain 2'-phenyl-6-azido-9α-fluoro-11β,17α,21-trihydroxy-16α-methyl-20-keto-4,6-pregnadieno[3,2-c]pyrazole 21-acetate.

EXAMPLE 5

2'-Phenyl-6-Azido-17α,21-Dihydroxy-20-Keto-4,6-Pregnadieno/3,2-c/Pyrazole 21-Lower Alkanoates

A.

2'-Phenyl-6-Azido-7-Bromo-17α,21-Dihydroxy-20-Keto-4-Pregneno-/3,2-c/Pyrazole 21-Lower Alkanoates In a manner similar to that described in Example 1A or 2A treat each of the following 2'-phenyl-17α,21-dihydroxy-20-keto-4,6-pregnadieno[3,2-c]pyrazole 21-lower alkanoates with hydrazoic acid and N-bromosuccinimide in dichloromethane in the presence of t-butanol:

1. 2'-phenyl-11β,16α,17α,21-tetrahydroxy-20-keto-4,6-pregnadieno[3,2-c]pyrazole 16,21-diacetate,
2. 2'-phenyl-11β,21-dihydroxy-16α,17α-isopropylidenedioxy-20-keto-4,6-pregnadieno[3,2-c]pyrazole 21-acetate,
3. 2'-phenyl-9α-floro-11β,16α,17α,21-tetrahydroxy-20-keto-4,6-pregnadieno[3,2-c]pyrazole 16,21-diacetate,
4. 2'-phenyl-9α-fluoro-11,20-diketo-16α,17α,21-trihydroxy-4,6-pregnadieno[3,2-c]pyrazole 16,21-dipropionate,
5. 2'-phenyl-9α-fluoro-11β,17α,21-trihydroxy-16-methylene-20keto-4,6-pregnadieno[3,2-c]-pyrazole 21-acetate,
6. 2'-phenyl-9α-fluoro-11,20-diketo-16-methylene-17α,21-dihydroxy-4,6-pregnadieno[3,2-c]pyrazole 21-acetate,
7. 2'-phenyl-9α,11β-dichloro-17α,21-dihydroxy-20-keto-4,6-pregnadieno[3,2-c]pyrazole 21-acetate,
8. 2'-phenyl-9α,11β-dichloro-17α,21-dihydroxy-20-keto-4,6-pregnadieno[3,2-c]pyrazole 17-valerate,
9. 2'-phenyl-9α,11β-dichloro-17α,21-dihydroxy-20-keto-4,6-pregnadieno[3,2-c]pyrazole 17,21-dipropionate,
10. 2'-phenyl-9α,11β-dichloro-17α,21-isopropylidenedioxy-20-keto-4,6-pregnadieno[3,2-c]pyrazole,
11. 2'-phenyl-9α,11β-dichloro-16α,17α,21-trihydroxy-20-keto-4,6-pregnadieno[3,2-c]pyrazole 16,21-diacetate,
12. 2'-phenyl-9α,11β-dichloro-16α,17α-isopropylidenedioxy-20-keto-21-hydroxy-4,6-pregnadieno[3,2-c]pyrazole 21-acetate,
13. 2'-phenyl-9α,11β-dichloro-16α-methyl-17α,21-dihydroxy-20-keto-4,6-pregnadieno[3,2-c]pyrazole 17,21-dipropionate,
14. 2'-phenyl-9α,11β-dichloro-16β-methyl-17α,21-dihydroxy-20-keto-4,6-pregnadieno[3,2-c]pyrazole 21-acetate,
15. 2'-phenyl-9α,11β-dichloro-16β-methyl-17α,21-dihydroxy-20keto-4,6-pregnadieno[3,2-c]pyrazole 17,21-dipropionate,
16. 2'-phenyl-9α,11β-dichloro-16-methylene-17α,21-dihydroxy-20-keto-4,6-pregnadieno[3,2-c]pyrazole 21-acetate,
17. 2'-phenyl-9α-bromo-11β-chloro-17α,21-dihydroxy-20-keto-4,6-pregnadieno[3,2-c]pyrazole 21-acetate,
18. 2'-phenyl-9α-bromo-11β-chloro-16α-methyl-17α,21-dihydroxy-20-keto-4,6-pregnadieno[3,2-c]pyrazole 21-acetate,
19. 2'-phenyl-9α-bromo-11β-chloro-16β-methyl-17α,21-dihydroxy-20-keto-4,6-pregnadieno[3,2-c]pyrazole 21-acetate,
20. 2'-phenyl-9α-bromo-11β-chloro-16-methylene-17α,21-dihydroxy-20-keto-4,6-pregnadieno[3,2-c]pyrazole 21-acetate.

Isolate and purify each of the resultant products in a manner similar to that described in Example 1A to obtain, respectively, 1. 2'-phenyl-6-azido-7-bromo-11β,16α,17α,21-tetrahydroxy-20-keto-4-pregneno[3,2-c]pyrazole 16,21-diacetate,
2. 2'-phenyl-6-azido-7-bromo-11β,21-dihydroxy-16α,17α-isopropylidenedioxy-20-keto-4-pregneno[3,2-c]-pyrazole 21-acetate,
3. 2'-phenyl-6-azido-7-bromo-9α-fluoro-11β,16α,17α,21-tetrahydroxy-20-keto-4-pregneno[3,2-c]pyrazole 16,21-diacetate,
4. 2'-phenyl-6-azido-7-bromo-9α-fluoro-11,20-diketo-16α,17α,21-trihydroxy-4-pregneno[3,2-c]pyrazole 16,21-dipropionate,
5. 2'-phenyl-6-azido-7-bromo-9α-fluoro-11β,17α,21-trihydroxy-16-methylene-20-keto-4-pregneno[3,2-c]-pyrazole 21-acetate,
6. 2'-phenyl-6-azido-7-bromo-9α-fluoro-11,20-diketo-16-methylene-17α,21-dihydroxy-4-pregneno[3,2-c]-pyrazole 21-acetate,
7. 2'-phenyl-6-azido-7-bromo-9α,11β-dichloro-17α,21-dihydroxy-20-keto-4-pregneno[3,2-c]pyrazole 21-acetate,
8. 2'-phenyl-6-azido-7-bromo-9α,11β-dichloro-17α,21-dihydroxy-20-keto-4-pregneno[3,2-c]pyrazole 17 valerate,
9. 2'-phenyl-6-azido-7-bromo-9α,11β-dichloro-17α,21-dihydroxy-20-keto-4-pregneno[3,2-c]pyrazole 17,21-dipropionate,
10. 2'-phenyl-6-azido-7-bromo-9α,11β-dichloro-17α,21-isopropylidenedioxy-20-keto-4-pregneno[3,2-c]-pyrazole,
11. 2'-phenyl-6-azido-7-bromo-9α,11β-dichloro-16α,17α,21-trihydroxy-20-keto-4-pregneno[3,2-c]pyrazole 16,21-diacetate,
12. 2'-phenyl-6-azido-7-bromo-9α,11β-dichloro-16α,17α-isopropylidenedioxy-20-keto-21-hydroxy-4-pregneno-[3,2-c]pyrazole 21-acetate,
13. 2'-phenyl-6-azido-7-bromo-9α,11β-dichloro-16α-methyl-17α,21-dihydroxy-20-keto-4-pregneno[3,2-c]pyrazole-17,21-dipropionate,
14. 2'-phenyl-6-azido-7-bromo-9α,11β-dichloro-16β-methyl-17α,21-dihydroxy-20-keto-4-pregneno[3,2-c]pyrazole 21-acetate,
15. 2'-phenyl-6-azido-7-bromo-9α,11β-dichloro-16β-methyl-17α,21-dihydroxy-20-keto-4-pregneno[3,2-c]pyrazole 17,21-dipropionate,
16. 2'-phenyl-6-azido-7-bromo-9α,11β-dichloro-16-methylene-17α,21-dihydroxy-20-keto-4-pregneno[3,2-c]pyrazole 21-acetate,
17. 2'-phenyl-6-azido-7,9α-dibromo-11β-chloro-17α,21-dihydroxy-20-keto-4-pregneno[3,2-c]pyrazole 21-acetate,
18. 2'-phenyl-6-azido-7,9α-dibromo-11β-chloro-16α-methyl-17α,21-dihydroxy-20-keto-4-pregneno[3,2-c]pyrazole 21-acetate,
19. 2'-phenyl-6-azido-7,9α-dibromo-11β-chloro-16β-methyl-17α,21-dihydroxy-20-keto-4-pregneno[3,2-c]pyrazole 21-acetate,
20. 2'-phenyl-6-azido-7,9α-dibromo-11β-chloro-16-methylene-17α,21-dihydroxy-20-keto-4-pregneno[3,2-c]pyrazole 21-acetate.

B.
2'-Phenyl-6-Azido-17α,21-Dihydroxy-20-Keto-4,6-Pregnadieno[3,2-c]Pyrazole 21-Lower Alkanoates In a manner similar to that described in Example 1B treat each of the 2'-phenyl-6-azido-7-bromo-17α,21-dihydroxy-20-keto-4-pregneno[3,2-c]pyrazole 21-lower alkanoates obtained as described in Example 5A with tetramethylammonium fluoride in acetonitrile at room temperature. Isolate and purify each of the resultant products to obtain, respectively, 1. 2'-phenyl-6-azido-11β,16α,17α,21-tetrahydroxy-20-keto-4,6-pregnadieno[3,2-c]pyrazole 16,21-diacetate,
2. 2'-phenyl-6-azido-11β,21-dihydroxy-16α,17α-isopropylidenedioxy-20-keto-4,6-pregnadieno[3,2-c]pyrazole 21-acetate,
3. 2'-phenyl-6-azido-9α-fluoro-11β,16α,17α,21-tetrahydroxy-20-keto-4,6-pregnadieno[3,2-c]pyrazole 16,21-diacetate,
4. 2'-phenyl-6-azido-9α-fluoro-11,20-diketo-16α,17α,21 trihydroxy-4,6-pregnadieno[3,2-c]pyrazole 16,21dipropionate,
5. 2'-phenyl-6-azido-9α-fluoro-11β,17α,21-trihydroxy-16-methylene-20-keto-4,6-pregnadieno[3,2-c]pyrazole 21-acetate,
6. 2'-phenyl-6-azido-9α-fluoro-11,20-diketo-16-methylene-17α,21-dihydroxy-4,6-pregnadieno[3,2-c]pyrazole 21-acetate,
7. 2'-phenyl-6-azido-9α,11β-dichloro-17α,21-dihydroxy-20-keto-4,6-pregnadieno[3,2-c]pyrazole 21-acetate,
8. 2'-phenyl-6-azido-9α,11β-dichloro-17α,21-dihydroxy20-keto-4,6-pregnadieno[3,2-c]pyrazole 17-valerate,
9. 2'-phenyl-6-azido-9α,11β-dichloro-17α,21-dihydroxy 20-keto-4,6-pregnadieno[3,2-c]pyrazole 17,21-dipropionate,
10. 2'-phenyl-6-azido-9α,11β-dichloro-17α,21-isopropylidene-dioxy-20-keto-4,6-pregnadieno[3,2-c]pyrazole
11. 2'-phenyl-6-azido-9α,11β-dichloro-16α17α,21-trihydroxy-20-keto-4,6-pregnadieno[3,2-c]pyrazole 16,21-diacetate,
12. 2'-phenyl-6-azido-9α,11β-dichloro-16α,17α-isopropylidene-dioxy-20-keto-21-hydroxy-4,6-pregnadieno[3,2-c]pyrazole 21-acetate,
13. 2'-phenyl-6-azido-9α,11β-dichloro-16β-methyl-17α,21-dihydroxy-20-keto-4,6-pregnadieno[3,2-c]pyrazole 17,21-dipropionate,
14. 2'-phenyl-6-azido-9α,11β-dichloro-16β-methyl-17α,21-dihydroxy-20-keto-4,6-pregnadieno[3,2-c]pyrazole 21-acetate,
15. 2'-phenyl-6-azido-9α,11β-dichloro-16β-methyl-17α,21-dihydroxy-20-keto-4,6-pregnadieno[3,2-c]pyrazole 17,21-dipropionate,
16. 2'-phenyl-6-azido-9α,11β-dichloro-16-methylene-17α,21-dihydroxy-20-keto-4,6-pregnadieno[3,2-c]pyrazole 21-acetate,
17. 2'-phenyl-6-azido-9α-bromo-11β-chloro-17α,21-dihydroxy-20-keto-4,6-pregnadieno[3,2-c]pyrazole 21-acetate,
18. 2'-phenyl-6-azido-9α-bromo-11β-chloro-16α-methyl-17α,21-dihydroxy-20-keto-4,6-pregnadieno[3,2-c]pyrazole 21-acetate,
19. 2'-phenyl-6-azido-9α-bromo-11β-chloro-16β-methyl-17α,21-dihydroxy-20-keto-4,6-pregnadieno[3,2-c]pyrazole 21-acetate,
20. 2'-phenyl-6-azido-9α-bromo-11β-chloro-16-methylene-17α,21-dihydroxy-20-keto-4,6-pregnadieno[3,2-c]pyrazole 21-acetate.

EXAMPLE 6

2'-Phenyl-6-Azido-20-Keto-21-Desoxy 4,6-Pregnadieno/3,2-c/Pyrazoles

A.
2'-Phenyl-6-Azido-7-Bromo-20-Keto-21-Desoxy-4-Pregneneo 3,2-c/Pyrazoles

In a manner similar to that described in Example 1A or 2A treat each of the following 2'-phenyl-20-keto-21-desoxy-4,6-pregnadieno [3,2-c]pyrazoles with hydrazoic acid and N-bromosuccinimide in dichloromethane in the presence of t-butanol: ps 1. 2'-phenyl-9α,11β-dichloro-16-methylene-17α-acetoxy-20-keto-4,6-pregnadieno[3,2-c]pyrazole,
2. 2'-phenyl-9α,11β-dichloro-16-ethylidene-17α-acetoxy-20-keto-4,6-pregnadieno[3,2-c]pyrazole,
3. 2'-phenyl-9α-bromo-11β-fluoro-16-methylene-17α-acetoxy-20-keto-4,6-pregnadieno[3,2-c]pyrazole,
4. 2'-phenyl-9α-fluoro-11β-hydroxy-16-methylene-17α-acetoxy-20-keto-4,6-pregnadieno[3,2-c]pyrazole,
5. 2'-phenyl-9α-fluoro-11,20-diketo-16-methylene-17αacetoxy-4,6-pregnadieno[3,2-c]pyrazole,
6. 2'-phenyl-9α,11β-dichloro-21-fluoro-16-methylene-17α-acetoxy-20-keto-4,6-pregnadieno[3,2-c]pyrazole,
7. 2'-phenyl-9α,11β, 21-trichloro-16-methylene-17α-acetoxy-20-keto-4,6-pregnadieno[3,2-c]pyrazole,
8. 2'-phenyl-9α-fluoro-11β-hydroxy-16-chloromethylene-17α-acetoxy-20-keto-4,6-pregnadieno[3,2-c]pyrazole,
9. 2'-phenyl-9α-fluoro-11β-hydroxy-16-fluoromethylene-17α-acetoxy-20-keto-4,6-pregnadieno[3,2-c]pyrazole,
10. 2'-phenyl-16α,17α-isopropylidenedioxy-20-keto-4,6-pregnadieno[3,2-c]pyrazole,
11. 2'-phenyl-9α,11β-dichloro-16α,17α-isopropylidenedioxy-20-keto-4,6-pregnadieno[3,2-c]pyrazole,
12. 2'-phenyl-9α-fluoro-11β-hydroxy-16α,17α-isopropylidenedioxy-20-keto-4,6-pregnadieno[3,2-c]pyrazole,
13. 2'-phenyl-9α,11β-dichloro-16β-methyl-17α-acetoxy-20-keto-4,6-pregnadieno[3,2-c]pyrazole,
14. 2'-phenyl-9α,11β-dichloro-16α-methyl-17α-acetoxy 20-keto-4,6-pregnadieno[3,2-c]pyrazole,
15. 2'-phenyl-9α-fluoro-11,20-diketo-16β-methyl-17α-acetoxy-4,6-pregnadieno[3,2-c]pyrazole,
16. 2'-phenyl-9α-fluoro-11,20-diketo-16α-methyl-17αacetoxy-20-keto-4,6-pregnadieno[3,2-c]pyrazole,
17. 2'-phenyl-9α-fluoro-11β-hydroxy-16β-methyl-17αacetoxy-20-keto-4,6-pregnadieno[3,2-c]pyrazole,
18. 2'-phenyl-9α-fluoro-11β-hydroxy-16α-methyl-17α-acetoxy-20-keto-4,6-pregnadieno[3,2-c]pyrazole,
19. 2'-phenyl-9α,21-difluoro-11,20 -diketo-17α-hydroxy-4,6-pregnadieno[3,2-c]pyrazole,
20. 2'-phenyl-9α,21-difluoro-11,20-diketo-16α-methyl 17α-hydroxy-4,6-pregnadieno[3,2-c]pyrazole,
21. 2'-phenyl-9α,21-difluoro-11,20-diketo-16β-methyl-17α-hydroxy-4,6-pregnadieno[3,2-c]pyrazole,
22. 2'-phenyl-9α,21-difluoro-11β,17α-dihydroxy-20-keto-4,6-pregnadieno[3,2-c]pyrazole,
23. 2'-phenyl-9α,21-difluoro-11β,17α-dihydroxy-16α-methyl-20-keto-4,6-pregnadieno[3,2-c]pyrazole,
24. 2'-phenyl-9α,21-difluoro-11β,17α-dihydroxy-16βmethyl-20-keto-4,6-pregnadieno[3,2-c]pyrazole,
25. 2'-phenyl-9α-fluoro-11β-hydroxy-20-keto-4,6-pregnadieno[3,2-c]pyrazole,
26. 2'-phenyl-9α-fluoro-11β-hydroxy-16α-methyl-20-keto-4,6-pregnadieno[3,2-c]pyrazole,
27. 2'-phenyl-9α-fluoro-11β-hydroxy-16β-methyl-20-keto-4,6-pregnadieno[3,2-c]pyrazole,
28. 2'-phenyl-9α,11β-dichloro-20-keto-4,6-pregnadieno[3,2-c]pyrazole,
29. 2'-phenyl-9α,11β-dichloro-16α-methyl-20-keto-4,6-pregnadieno[3,2-c]pyrazole,
30. 2'-phenyl-9α,11β-dichloro-16β-methyl-20-keto-4,6-pregnadieno[3,2-c]pyrazole,
31. 2'-phenyl-9α-bromo-11β-chloro-20-keto-4,6-pregnadieno[3,2-c]pyrazole,
32. 2'-phenyl-9α-bromo-11β-chloro-16α-methyl-20-keto-4,6-pregnadieno[3,2-c]pyrazole,
33. 2'-phenyl-9α-bromo-11β-chloro-16β-methyl-20-keto-4,6-pregnadieno[3,2-c]pyrazole,
34. 2'-phenyl-9α,11β,21-trichloro-20-keto-4,6-pregnadieno[3,2-c]pyrazole,
35. 2'-phenyl-9α,11β,21-trichloro-16α-methyl-20-keto-4,6-pregnadieno[3,2-c]pyrazole,
36. 2'-phenyl-9α,11β,21-trichloro-16β-methyl-20-keto-4,6-pregnadieno[3,2-c]pyrazole,
37. 2'-phenyl-9α,11β-dichloro-21-fluoro-20-keto-4,6-pregnadieno[3,2-c]pyrazole,
38. 2'-phenyl-9α,11β-dichloro-21-fluoro-16β-methyl 20-keto-4,6-pregnadieno[3,2-c]pyrazole,
39. 2'-phenyl-9α,11β-dichloro-21-fluoro-16β-methyl-20-keto-4,6-pregnadieno[3,2-c]pyrazole,
40. 2'-phenyl-16-methylene-17α-acetoxy-20-keto-4,6-pregnadieno[3,2-c]pyrazole,
41. 2'-phenyl-16-(n-butylidene)-17α-acetoxy-20-keto-4,6-pregnadieno[3,2-c]pyrazole,
42. 2'-phenyl-16-methylene-17α-propionoxy-20-keto-4,6-pregnadieno [3,2-c]pyrazole,
43. 2'-phenyl-11α-hydroxy-16-methylene-17α-acetoxy 20-keto-4,6-pregnadieno[3,2-c]pyrazole,
44. 2'-phenyl-11,20-diketo-16-methylene-17α-acetoxy 4,6-pregnadieno[3,2-c]pyrazole,
45. 2'-phenyl-16-methylene-17α-acetoxy-20-keto-21-fluoro-4,6-pregnadieno[3,2-c]pyrazole,
46. 2'-phenyl-16-methylene-17α-acetoxy-20-keto-21-chloro-4,6-pregnadieno[3,2-c]pyrazole,
47. 2'-phenyl-16-chloromethylene-17α-acetoxy-20-keto-4,6-pregnadieno[3,2-c]pyrazole,
48. 2'-phenyl-16-fluoromethylene-17α-acetoxy-20-keto-4,6-pregnadieno[3,2-c]pyrazole,
49. 2'-phenyl-11β-hydroxy-16-chloromethylene-17α-acetoxy-20-keto-4,6-pregnadieno[3,2-c]pyrazole,
50. 2'-phenyl-16β-methyl-17α-acetoxy-20-keto-4,6-pregnadieno[3,2-c]pyrazole,
51. 2'-phenyl-16α-methyl-17α-acetoxy-20-keto-4,6-pregnadieno[3,2-c]pyrazole,
52. 2'-phenyl-11,20-diketo-16β-methyl-17α-acetoxy 4,6-pregnadieno[3,2-c]pyrazole,
53. 2'-phenyl-11,20-diketo-16α-methyl-17α-acetoxy 4,6-pregnadieno[3,2-c]pyrazole, 54. 2'-phenyl-11β-hydroxy-16β-methyl-17α-acetoxy 20-keto-4,6-pregnadieno[3,2-c]pyrazole,
55. 2'-phenyl-11β-hydroxy-16α-methyl-17α-acetoxy 20-keto-4,6-pregnadieno[3,2-c]pyrazole,
56. 2'-phenyl-16β-methyl-17α-acetoxy-20-keto-21-fluoro-4,6-pregnadieno[3,2-c]pyrazole,
57. 2'-phenyl-16α-methyl-17α-acetoxy-20-keto-21fluoro-4,6-pregnadieno[3,2-c]pyrazole,
58. 2'-phenyl-11,20-diketo-17α-hydroxy-21-fluoro-4,6-pregnadieno[3,2-c]pyrazole,
59. 2'-phenyl-11,20-diketo-16α-methyl-17α-hydroxy21-fluoro-4,6-pregnadieno[3,2-c]pyrazole,
60. 2'-phenyl-11,20-diketo-16β-methyl-17α-hydroxy 21-fluoro-4,6-pregnadieno[3,2-c]pyrazole,
61. 2'-phenyl-17α-hydroxy-20-keto-21-fluoro-4,6-pregnadieno[3,2-c]pyrazole,
62. 2'-phenyl-16α-methyl-17α-hydroxy-20-keto 21-fluoro-4,6-pregnadieno[3,2-c]pyrazole,
63. 2'-phenyl-16β-methyl-17α-hydroxy-20-keto21-fluoro-4,6-pregnadieno[3,2-c]pyrazole,
64. 2'-phenyl-20-keto-4,6-pregnadieno[3,2-c]pyrazole,
65. 2'-phenyl-16α-methyl-20-keto-4,6-pregnadieno[3,2-c]pyrazole,
66. 2'-phenyl-16β-methyl-20-keto-4,6-pregnadieno[3,2-c]pyrazole,
67. 2'-phenyl-20-keto-21-fluoro-4,6-pregnadieno[3,2-c]pyrazole,
68. 2'-phenyl-16α-methyl-20-keto-21-fluoro-4,6-pregnadieno[3,2-c]pyrazole,
69. 2'-phenyl-16β-methyl-20-keto-21-fluoro-4,6-pregnadieno[3,2-c[pyrazole,
70. 2'-phenyl-11,20-diketo-4,6-pregnadieno[3,2-c]pyrazole,
71. 2'-phenyl-11,20-diketo-16α-methyl-4,6-pregnadieno [3,2-c]pyrazole,
72. 2'-phenyl-11,20-diketo-16β-methyl-4,6-pregnadieno [3,2-c]pyrazole,
73. 2'-phenyl-11β-hydroxy-20-keto-4,6-pregnadieno [3,2-c]pyrazole,
74. 2'-phenyl-11β-hydroxy-16α-methyl-20-keto-4,6-pregnadieno[3,2-c]pyrazole,
75. 2'-phenyl-11α-hydroxy-16β-methyl-20-keto-4,6-pregnadieno[3,2-c]pyrazole.

Isolate and purify each of the resultant products in a manner similar to that described in Example 1A or 2A to obtain, respectively, 1. 2'-phenyl-6-azido-7-bromo-9α,11β-dichloro-16-methylene-17α-acetoxy-20-keto-4-pregneno[3,2-c]pyrazole,
2. 2'-phenyl-6-azido-7-bromo-9α,11β-dichloro-16-ethylidene-17α-acetoxy-20-keto-4-pregneno[3,2-c]pyrazole,
3. 2'-phenyl-6-azido-7,9α-dibromo-11β-fluoro-16-methylene-17α-acetoxy-20-keto-4-pregneno[3,2-c]pyrazole,
4. 2'-phenyl-6-azido-7-bromo-9α-fluoro-11β-hydroxy-16-methylene-17α-acetoxy-20-keto-4-pregneno[3,2-c]pyrazole,
5. 2'-phenyl-6-azido-7-bromo-9α-fluoro-11,20-diketo-16-methylene-17α-acetoxy-4-pregneno[3,2-c]pyrazole,
6. 2'-phenyl-6-azido-7-bromo-9α,11β-dichloro-21-fluoro-16-methylene-17α-acetoxy-20-keto-4-pregneno[3,2-c]pyrazole,
7. 2'-phenyl-6-azido-7-bromo-9α,11β,21-trichloro-16-methylene-17α-acetoxy-20-keto-4-pregneno[3,2-c]pyrazole,
8. 2'-phenyl-6-azido-7-bromo-9α-fluoro-11β-hydroxy-16-chloromethylene-17α-acetoxy-20-keto-4-pregneno[3,2-c]pyrazole,
9. 2'-phenyl-6-azido-7-bromo-9α-fluoro-11β-hydroxy-16-fluoromethylene-17α-acetoxy-20-keto-4-pregneno[3,2-c]pyrazole,
10. 2'-phenyl-6-azido-7-bromo-16α,17α-isopropylidenedioxy-20-keto-4-pregneno[3,2-c]pyrazole,
11. 2'-phenyl-6-azido-7-bromo-9α,11β-dichloro-16α,17α-isopropylidenedioxy-20-keto-4-pregneno[3,2-c]pyrazole,
12. 2'-phenyl-6-azido-7-bromo-9α-fluoro-11β-hydroxy-16α,17α-isopropylidenedioxy-20-keto-4-pregneno[3,2-c]pyrazole,
13. 2'-azido-6-azide-7-bromo-9α,11β-dichloro-16β-methyl-17α-acetoxy-20-keto-4-pregneno[3,2-c]pyrazole,
14. 2'-phenyl-6-azido-7-bromo-9α,11β-dichloro-16α-methyl-17α-acetoxy-4-pregneno[3,2-c]pyrazole,
15. 2'-phenyl-6-azido-7-bromo-9α-fluoro-11,20-diketo-16β-methyl-17α-acetoxy-4-pregneno[3,2-c]pyrazole,
16. 2'-phenyl-6-azido-7-bromo-9α-fluoro-11,20-diketo-16α-methyl-17α-acetoxy-4-pregneno[3,2-c]pyrazole,
17. 2'-phenyl-6-azido-7-bromo-9α-fluoro-11β-hydroxy-16β-methyl-17α-acetoxy-20-keto-4-pregneno[3,2-c]pyrazole,
18. 2'-phenyl-6-azido-7-bromo-9α-fluoro-11β-hydroxy-16α-methyl-17α-acetoxy-20-keto-4-pregneno[3,2-c]pyrazole,
19. 2'-phenyl-6-azido-7-bromo-9α,21-difluoro-11,20-diketo-17α-hydroxy-4-pregneno[3,2-c]pyrazole,
20. 2'-phenyl-6-azido-7-bromo-9α,21-difluoro-11,20-diketo-16α-methyl-17α-hydroxy-4-pregneno[3,2-c]pyrazole,
21. 2'-phenyl-6-azido-7-bromo-9α,21-difluoro-11,20-diketo-16β-methyl-17α-hydroxy-4-pregneno[3,2-c]pyrazole,
22. 2'-phenyl-6-azido-7-bromo-9α,21-difluoro-11β,17α-dihydroxy-20-keto-4-pregneno[3,2-c]pyrazole,
23. 2'-phenyl-6-azido-7-bromo-9α,21-difluoro-11β,17α-dihydroxy-16α-methyl-20-keto-4-pregneno[3,2-c]pyrazole,
24. 2'-phenyl-6-azido-7-bromo-9α,21-difluoro-11β,17α-dihydroxy-16β-methyl-20-keto-4-pregneno[3,2-c]pyrazole,
25. 2'-phenyl-6-azido-7-bromo-9α-fluoro-11β-hydroxy-20-keto-4-pregneno[3,2-c]pyrazole,
26. 2'-phenyl-6-azido-7-bromo-9α-fluoro-11β-hydroxy-16α-methyl-20-keto-4-pregneno[3,2-c]pyrazole,
27. 2'-phenyl-6-azido-7-bromo-9α-fluoro-11β-hydroxy-16β-methyl-20-keto-4-pregneno[3,2-c]pyrazole,
28. 2'-phenyl-6-azido-7-bromo-9α,11β-dichloro-20-keto-4-pregneno[3,2-c]pyrazole,
29. 2'-phenyl-6-azido-7-bromo-9α,11β-dichloro-16α-methyl-20-keto-4-pregneno[3,2-c]pyrazole,
30. 2'-phenyl-6-azido-7-bromo-9α,11β-dichloro-16β-methyl-20-keto-4-pregneno[3,2-c]pyrazole, 31. 2'-phenyl-6-azido-7,9α-dibromo-11α-chloro-20-keto-4-pregneno[3,2-c]pyrazole,
32. 2'-phenyl-6-azido-7,9α-dibromo-11β-chloro-16α-methyl-20-keto-4-pregneno[3,2-c]pyrazole,
33. 2'-phenyl-6-azido-7,9α-dibromo-11β-chloro-16β-methyl-20-keto-4-pregneno[3,2-c]pyrazole,
34. 2'-phenyl-6-azido-7-bromo-9α,11β,21-trichloro-20-keto-4-pregneno[3,2-c]pyrazole,
35. 2'-phenyl-6-azido-7-bromo-9α,11β,21-trichloro-16α-methyl-20-keto-4-pregneno[3,2-c]pyrazole,
36. 2'-phenyl-6-azido-7-bromo-9α,11β,21-trichloro-16β-methyl-20-keto-4-pregneno[3,2-c]pyrazole,
37. 2'-phenyl-6-azido-7-bromo-9α,11β-dichloro-21-fluoro-20-keto-4-pregneno[3,2-c]pyrazole,
38. 2'-phenyl-6-azido-7-bromo-9α,11β-dichloro-21-fluoro-16α-methyl-20-keto-4-pregneno[3,2-c]pyrazole,
39. 2'-phenyl-6-azido-7-bromo-9α,11β-dichloro-21-fluoro-16β-methyl-20-keto-4-pregneno[3,2-c]pyrazole,
40. 2'-phenyl-6-azido-7-bromo-16-methylene-17α-acetoxy-20-keto-4-pregneno[3,2-c]pyrazole,
41. 2'-phenyl-6-azido-7-bromo-16-(n-butylidene)-17α-acetoxy-20-keto-4-pregneno[3,2-c]pyrazole,
42. 2'-phenyl-6-azido-7-bromo-16-methylene-17α-propionoxy-20-keto-4-pregneno[3,2-c]pyrazole,
43. 2'-phenyl-6-azido-7-bromo-11β-hydroxy-16-methylene-17α-acetoxy-20-keto-4-pregneno[3,2-c]pyrazole,
44. 2'-phenyl-6-azido-7-bromo-11,20-diketo-16-methylene-17α-acetoxy-4-pregneno[3,2-c]pyrazole,
45. 2'-phenyl-6-azido-7-bromo-16-methylene-17α-acetoxy-20-keto-21-fluoro-4-pregneno[3,2-c]pyrazole,
46. 2'-phenyl-6-azido-7-bromo-16-methylene-17α-acetoxy-20-keto-21-chloro-4-pregneno[3,2-c]pyrazole,
47. 2'-phenyl-6-azido-7-bromo-16-chloromethylene-17α-acetoxy-20-keto-4-pregneno[3,2-c]pyrazole,
48. 2'-phenyl-6-azido-7-bromo-16-fluoromethylene-17α-actoxy-20-keto-4-pregneno[3,2-c]pyrazole,
49. 2'-phenyl-6-azido-7-bromo-11β-hydroxy-16-chloromethylene-17α-acetoxy-20-keto-4-pregneno[3,2-c]pyrazole,
50. 2'-phenyl-6-azido-7-bromo-16β-methyl-17α-acetoxy-20-keto-4-pregneno[3,2-c]pyrazole,
51. 2'-phenyl-6-azido-7-bromo-16α-methyl-17α-acetoxy-20-keto-4-pregneno[3,2-c]pyrazole,
52. 2'-phenyl-6-azido-7-bromo-11,20-diketo-16β-methyl-17α-acetoxy-4-pregneno[3,2-c]pyrazole,
53. 2'-phenyl-6-azido-7-bromo-11,20-diketo-16α-methyl-17α-acetoxy-4-pregneno[3,2-c]pyrazole,
54. 2'-phenyl-6-azido-7-bromo-11β-hydroxy-16β-methyl-17α-acetoxy-20-keto-4-pregneno[3,2-c]pyrazole,
55. 2'-phenyl-6-azido-7-bromo-11β-hydroxy-16α-methyl-17α-acetoxy-20-keto-4-pregneno[3,2-c]pyrazole,
56. 2'-phenyl-6-azido-7-bromo-16α-methyl-17α-acetoxy-20-keto-21-fluoro-4-pregneno[3,2-c]pyrazole,
57. 2'-phenyl-6-azido-7-bromo-16α-methyl-17α-acetoxy-20-keto-21-fluoro-4-pregneno[3,2-c]pyrazole,
58. 2'-phenyl-6-azido-7-bromo-11,20-diketo-17α-hydroxy-21-fluoro-4-pregneno[3,2-c]pyrazole,
59. 2'-phenyl-6-azido-7-bromo-11,20-diketo-16α-methyl-17α-hydroxy-21-fluoro-4-pregneno[3,2-c]pyrazole,
60. 2'-phenyl-6-azido-7-bromo-11,20-diketo-16β-methyl-17α-hydroxy-21-fluoro-4-pregneno[3,2-c]pyrazole,
61. 2'-phenyl-6-azido-7-bromo-17α-hydroxy-20-keto-21-fluoro-4-pregneno[3,2-c]pyrazole,
62. 2'-phenyl-6-azido-7-bromo-16α-methyl-17α-hydroxy-20-keto-21-fluoro-4-pregneno[3,2-c]pyrazole,
63. 2'-phenyl-6-azido-7-bromo-16β-methyl-17α-hydroxy-20-keto-21-fluoro-4-pregneno[3,2-c]pyrazole,
64. 2'-phenyl-6-azido-7-bromo-20-keto-4-pregneno[3,2-c]pyrazole,
65. 2'-phenyl-6-azido-7-bromo-16α-methyl-20-keto-4-pregneno[3,2-c]pyrazole,
66. 2'-phenyl-6-azido-7-bromo-16β-methyl-20-keto-4-pregneno[3,2-c]pyrazole,
67. 2'-phenyl-6-azido-7-bromo-20-keto-21-fluoro-4-pregneno[3,2-c]pyrazole,
68. 2'phenyl-6azido-7-bromo-16α-methyl-20-keto-21-fluoro-4-pregneno[3,2-c]pyrazole,
69. 2'-phenyl-6-azido-7-bromo-16β-methyl-20-keto-21-fluoro-4-pregneno[3,2-c]pyrazole,
70. 2'-phenyl-6-azido-7-bromo-11,20-diketo-4-pregneno[3,2-c]pyrazole,
71. 2'-phenyl-6-azido-7-bromo-11,20-diketo-16α-methyl-4-pregneno[3,2-c]pyrazole,
72. 2'-phenyl-6-azido-7-bromo-11,20-diketo-16β-methyl-4-pregneno[3,2-c]pyrazole,
73. 2'-phenyl-6-azido-7-bromo-11β-hydroxy-20-keto-4-pregneno[3,2-c]pyrazole,
74. 2'-phenyl-6-azido-7-bromo-11β-hydroxy-16α-methyl-20-keto-4-pregneno[3,2-c]pyrazole,
75. 2'-phenyl-6-azido-7-bromo-11β-hydroxy-16β-methyl-20-keto-4-pregneno[3,2-c]pyrazole.

B.
2'-Phenyl-6-Azido-20-Keto-21-Desoxy-4,6-Pregnadieno[3,2-c]Pyrazoles

In a manner similar to that described in Example 1B treat each of the 2'-phenyl-6-azido-7-bromo-20-keto-4-pregneno[3,2-c]pyrazoles obtained in Example 6A with tetramethylammonium fluoride in acetonitrile under nitrogen at room temperature. Isolate and purify each of the resultant products in a manner similar to that described to obtain, respectively, 1. 2'-phenyl-6-azido-9α,11β-dichloro-16-methylene-17α-acetoxy-20-keto-4,6-pregnadieno[3,2-c]pyrazole,
2. 2'-phenyl-6-azido-9α,11β-dichloro-16-ethylidene-17α-acetoxy-20-keto-4,6-pregnadieno[3,2-c]pyrazole,
3. 2'-phenyl-6-azido-9α-bromo-11β-fluoro-16-methylene-17α-acetoxy-20-keto-4,6-pregnadieno[3,2-c]pyrazole,
4. 2'-phenyl-6-azido-9α-fluoro-11β-hydroxy-16-methylene-17α-acetoxy-20-keto-4,6-pregnadieno[3,2-c]pyrazole,
5. 2'-phenyl-6-azido-9α-fluoro-11,20-diketo-16-methylene-17α-acetoxy-4,6-pregnadieno[3,2-c]pyrazole, 6. 2'-phenyl-6-azido-9α,11β-dichloro-21-fluoro-16-methylene-17α-acetoxy-20-keto-4,6-pregnadieno[3,2-c]pyrazole,
7. 2'-phenyl-6-azido-9α,11β,21-trichloro-16-methylene-17α-acetoxy-20-keto-4,6-pregnadieno[3,2-c]pyrazole,
8. 2'-phenyl-6-azido-9α-fluoro-11β-hydroxy-16-chloromethylene-17α-acetoxy-20-keto-4,6-pregnadieno[3,2-c]pyrazole,
9. 2'-phenyl-6-azido-9α-fluoro-11β-hydroxy-16-fluoromethylene-17α-acetoxy-20-keto-4,6-pregnadieno[3,2-c]pyrazole,
10. 2'-phenyl-6-azido-16α,17α-isopropylidenedioxy-20-keto-4,6-pregnadieno[3,2-c]pyrazole,
11. 2'-phenyl-6-azido-9α,11β-dichloro-16α,17α-isopropylidenedioxy-20-keto-4,6-pregnadieno[3,2-c]pyrazole,
12. 2'-phenyl-6-azido-9α-fluoro-11β-hydroxy-16α,17α-isopropylidenedioxy-20-keto-4,6-pregnadieno[3,2-c]pyrazole,
13. 2'-phenyl-6-azido-9α,11β-dichloro-16β-methyl-17α-acetoxy-20-keto-4,6-pregnadieno[3,2-c]pyrazole,
14. 2'-phenyl-6-azido-9α,11β-dichloro-16α-methyl-17α-acetoxy-20-keto-4,6-pregnadieno[3,2-]-c]
15. 2'-phenyl-6-azido-9α-fluoro-11,20-diketo-16β-methyl-17α-acetoxy-4,6-pregnadieno[3,2-c]pyrazole,
16. 2'-phenyl-6-azido-9α-fluoro-11,20-diketo-16α-methyl-17α-acetoxy-20-keto-4,6-pregnadieno[3,2-c]pyrazole,
17. 2'-phenyl-6-azido-9α-fluoro-11β-hydroxy-16β-methyl-17α-acetoxy-20-keto-4,6-pregnadieno[3,2-c]pyrazole,
18. 2'-phenyl-6-azido-9α-fluoro-11β-hydroxy-16α-methyl-17α-acetoxy-20-keto-4,6-pregnadieno[3,2-c]pyrazole,
19. 2'-phenyl-6-azido-9α,21-difluoro-11,20-diketo-17α-hydroxy-4,6-pregnadieno[3,2-c]pyrazole,
20. 2'-phenyl-6-azido-9α,21-difluoro-11,20-diketo-16α-methyl-17α-hydroxy-4,6-pregnadieno[3,2-c]pyrazole,
21. 2'-phenyl-6-azido-9α,21-difluoro-11,20-diketo-16β-methyl-17β-hydroxy-4,6-pregnadieno[3,2-c]pyrazole,
22. 2'-phenyl-6-azido-9α,21-difluoro-11β,17α-dihydroxy-20-keto-4,6-pregnadieno[3,2-c]pyrazole,
23. 2'-phenyl-6-azido-9α,21-difluoro-11β,17α-dihydroxy-16α-methyl-20-keto-4,6-pregnadieno[3,2-c]pyrazole,
24. 2'-phenyl-6-azido-9α,21-difluoro-11β,17α-dihydroxy-16β-methyl-20-keto-4,6-pregnadieno[3,2-c]pyrazole,
25. 2'-phenyl-6-azido-9α-fluoro-11β-hydroxy-20-keto-4,6-pregnadieno[3,2-c]pyrazole,
26. 2'-phenyl-6-azido-9α-fluoro-11β-hydroxy-16α-methyl-20-keto-4,6-pregnadieno[3,2-c]pyrazole,
27. 2'-phenyl-6-azido-9α-fluoro-11β-hydroxy-16β-methyl-20-keto-4,6-pregnadieno[3,2-c]pyrazole,
28. 2'-phenyl-6-azido-9α,11β-dichloro-20-keto-4,6-pregnadieno[3,2-c]pyrazole,
29. 2'-phenyl-6-azido-9α,11β-dichloro-16α-methyl-20-keto-4,6-pregnadieno[3,2-c]pyrazole,
30. 2'-phenyl-6-azido-9α,11β-dichloro-16β-methyl-20-keto-4,6-pregnadieno[3,2-c]pyrazole,
31. 2'-phenyl-6-azido-9α-bromo-11β-chloro-20-keto-4,6-pregnadieno[3,2-c]pyrazole,
32. 2'-phenyl-6-azido-9α-bromo-11β-chloro-16α-methyl-20-keto-4,6-pregnadieno[3,2-c]pyrazole,
33. 2'-phenyl-6-azido-9α-bromo-11β-chloro-16β-methyl-20-keto-4,6-pregnadieno[3,2-c]pyrazole,
34. 2'-phenyl-6-azido-9α,11β,21-trichloro-20-keto-4,6-pregnadieno[3,2-c]pyrazole,
35. 2'-phenyl-6-azido-9α,11β,21-trichloro-16α-methyl-20-keto-4,6-pregnadieno[3,2-c]pyrazole,
36. 2'-phenyl-6-azido-9α,11β,21-trichloro-16β-methyl-20-keto-4,6-pregnadieno[3,2-c]pyrazole,
37. 2'-phenyl-6-azido-9α,11β-dichloro-21-fluoro-20-keto-4,6-pregnadieno[3,2-c]pyrazole,
38. 2'-phenyl-6-azido-9α,11β-dichloro-21-fluoro-16α-methyl-20-keto-4,6-pregnadieno[3,2-c]pyrazole,
39. 2'-phenyl-6-azido-9α,11β-dichloro-21-fluoro-16β-methyl-20-keto-4,6-pregnadieno[3,2-c]pyrazole.
40. 2'-phenyl-6-azido-16-methylene-17α-acetoxy-20-keto-4,6-pregnadieno[3,2-c]pyrazole,
41. 2'-phenyl-6-azido-16-(n-butylidene)-17α-acetoxy-20-keto-4,6-pregnadieno[3,2-c]pyrazole,
42. 2'-phenyl-6-azido-16-methylene-17α-propionyloxy-20-keto-4,6-pregnadieno[3,2-c]pyrazole,
43. 2'-phenyl-6-azido-11β-hydroxy-16-methylene-17α-acetoxy-20-keto-4,6-pregnadieno[3,2-c]pyrazole,
44. 2'-phenyl-6-azido-11,20-diketo-16-methylene-17α-acetoxy-4,6-pregnadieno[3,2-c]pyrazole,
45. 2'-phenyl-6-azido-16-methylene-17α-acetoxy-20-keto-21-fluoro-4,6-pregnadieno[3,2-c]pyrazole,
46. 2'-phenyl-6-azido-16-methylene-17α-acetoxy-20-keto-21-chloro-4,6-pregnadieno[3,2-c]pyrazole,
47. 2'-phenyl-6-azido-16-chloromethylene-17α-acetoxy-20-keto-4,6-pregnadieno[3,2-c]pyrazole,
48. 2'-phenyl-6-azido-16-fluoromethylene-17α-acetoxy-20-keto-4,6-pregnadieno[3,2-c]pyrazole,
49. 2'-phenyl-6-azido-11β-hydroxy-16-chloromethylene-17α-acetoxy-20-keto-4,6-pregnadieno[3,2-c]pyrazole,
50. 2'-phenyl-6-azido-16β-methyl-17α-acetoxy-20-keto-4,6-pregnadieno[3,2-c]pyrazole,
51. 2'-phenyl-6-azido-16α-methyl-17α-acetoxy-20-keto-4,6-pregnadieno[3,2-c]pyrazole,
52. 2'-phenyl-6-azido-11,20-diketo-16β-methyl-17α-acetoxy-4,6-pregnadieno[3,2-c]pyrazole,
53. 2'-phenyl-6-azido-11,20-diketo-16α-methyl-17α-acetoxy-4,6-pregnadieno[3,2-c]pyrazole,
54. 2'-phenyl-6-azido-11β-hydroxy-16β-methyl-17G2a-acetoxy-20-keto-4,6-pregnadieno[3,2-c]pyrazole,
55. 2'-phenyl-6-azido-11β-hydroxy-16α-methyl-17α-acetoxy-20-keto-4,6-pregnadieno[3,2-c]pyrazole,
56. 2'-phenyl-6-azido-16β-methyl-17α-acetoxy-20-keto-21-fluoro-4,6-pregnadieno[3,2-c]pyrazole,
57. 2'-phenyl-6-azido-16α-methyl-17α-acetoxy-20-keto-21-fluoro-4,6-pregnadieno[3,2-c]pyrazole,
58. 2'-phenyl-6-azido-11,20-diketo-17α-hydroxy-21-fluoro-4,6-pregnadieno[3,2-c]pyrazole,
59. 2'-phenyl-6-azido-11,20-diketo-16α-methyl-17α-hydroxy-21-fluoro-4,6-pregnadieno[3,2-c]pyrazole,
60. 2'-phenyl-6-azido-11,20-diketo-16β-methyl-17α-hydroxy-21-fluoro-4,6-pregnadieno[3,2-c]pyrazole, 61. 2'-phenyl-6-azido-17α-hydroxy-20-keto-21-fluoro-4,6-pregnadieno[3,2-c]pyrazole,
62. 2'-phenyl-6-azido-16α-methyl-17α-hydroxy-20-keto-21-fluoro-4,6-pregnadieno[3,2-c]pyrazole,
63. 2'-phenyl-6-azido-16β-methyl-17α-hydroxy-20-keto-21-fluoro-4,6-pregnadieno[3,2-c]pyrazole,
64. 2'-phenyl-6-azido-20-keto-4,6-pregnadieno[3,2-c]pyrazole,
65. 2'-phenyl-6-azido-16α-methyl-20-keto-4,6-pregnadieno[3,2-c]pyrazole,
66. 2'-phenyl-6-azido-16β-methyl-20-keto-4,6-pregnadieno[3,2-c]pyrazole,
67. 2'-phenyl-6-azido-20-keto-21-fluoro-4,6-pregnadieno[3,2-c]pyrazole,
68. 2'-phenyl-6-azido-16α-methyl-20-keto-21-fluoro-4,6-pregnadieno[3,2-c]pyrazole,
69. 2'-phenyl-6-azido-16β-methyl-20-keto-21-fluoro-4,6-pregnadieno[3,2-c]pyrazole,
70. 2'-phenyl-6-azido-11,20-diketo-4,6-pregnadieno[3,2-c]pyrazole,
71. 2'-phenyl-6-azido-11,20-diketo-16α-methyl-4,6-pregnadieno[3,2-c]pyrazole,
72. 2'-phenyl-6-azido-11,20-diketo-16β-methyl-4,6-pregnadieno[3,2-c]pyrazole,
73. 2'-phenyl-6-azido-11β-hydroxy-20-keto-4,6-pregnadieno[3,2-c]pyrazole,
74. 2'-phenyl-6-azido-11β-hydroxy-16α-methyl-20-keto-4,6-pregnadieno[3,2-c]pyrazole,
75. 2'-phenyl-6-azido-11β-hydroxy-16β-methyl-20-keto-4,6-pregnadieno[3,2-c]pyrazole.

EXAMPLE 7

Alternate Procedure for the Preparation of 2'-Phenyl-6-Azido-17α,21-Dihydroxy-20-Keto 4,6-Pregnadieno[3,2-c]Pyrazoles A.
2'-Hydroxymethylene-3-Keto-6-Azido-17α,20;20,21-Bismethylenedioxy-4,6-Pregnadienes In a manner similar to that described in Example 3A treat each of the following 3-keto-6-azido-4,6-pregnadienes with sodium hydride, sodium methoxide, and ethyl formate in benzene under an atmosphere of nitrogen:

1. 6-azido-17α,20;20,21-bismethylenedioxy-4,6-pregnadiene-11β-ol-3-one,
2. 6-azido-16α-methyl-17α,20;20,21-bismethylenedioxy-4,6-pregnadiene-11β-ol-3-one,
3. 6-azido-16β-methyl-17α,20;20,21-bismethylenedioxy-4,6-pregnadiene-11β-ol-3-one,
4. 6-azido-17α,20;20,21-bismethylenedioxy-4,6-pregnadiene-3,11-dione,
5. 6-azido-16α-methyl-17α,20;20,21-bismethylenedioxy-4,6-pregnadiene-3,11-dione,
6. 6-azido-16β-methyl-17α,20;20,21-bismethylenedioxy-4,6-pregnadiene-3,11-dione,
7. 6-azido-16-methylene-17α,20;20,21-bismethylenedioxy-4,6-pregnadiene-11β-ol-3-one,
8. 6-azido-16-methylene-17α,20;20,21-bismethylenedioxy-4,6-pregnadiene-3,11-dione,
9. 6-azido-9α,11β-dichloro-17α,20;20,21-bismethylenedioxy-4,6-pregnadiene-3-one.

Isolate and purify each of the resultant products in a manner similar to that described in Example 3A to obtain, respectively, 1. 2-hydroxymethylene-6-azido-17α,20;20,21-bismethylenedioxy-4,6-pregnadiene-11β-ol-3-one,
2. 2-hydroxymethylene-6-azido-16α-methyl-17α,20;20,21-bismethylenedioxy-4,6-pregnadiene-11β-ol-3-one,
3. 2-hydroxymethylene-6-azido-16β-methyl-17α,20;20,21-bismethylenedioxy-4,6-pregnadiene-11β-ol-3-one,
4. 2-hydroxymethylene-6-azido-17α,20;20,21-bismethylenedioxy-4,6-pregnadiene-3,11-dione,
5. 2-hydroxymethylene-6-azido-16α-methyl-17α,20;20,21-bismethylenedioxy-4,6-pregnadiene-3,11-dione,
6. 2-hydroxymethylene-6-azido-16β-methyl-17α,20;20,21-bismethylenedioxy-4,6-pregnadiene-3,11-dione,
7. 2-hydroxymethylene-6-azido-16-methylene-17α,20;20,21-bismethylenedioxy-4,6-pregnadiene-11β-ol-3-one,
8. 2-hydroxymethylene-6-azido-16-methylene-17α,20;20,21bismethylenedioxy-4,6-pregnadiene-3,11-dione,
9. 2-hydroxymethylene-6-azido-9α,11β-dichloro-17α,20;20,21-bismethylenedioxy-4,6-pregnadiene-3-one.

B.
2'-Phenyl-6-Azido-17α,20;20,21-Bismethylenedioxy-4,6-Pregnadieno[3,2-c]Pyrazoles In a manner similar to that described in Example 3B treat each of the 2-hydroxymethylene-6-azido-4,6-pregnadienes prepared as described in Example 3A with phenylhydrazine in ethanol. Isolate and purify each of the resultant products in a manner similar to that described to obtain, respectively, 1. 2'-phenyl-6-azido-11β-hydroxy-17α,20;20,21-bismethylenedioxy-4,6-pregnadieno[3,2-c]pyrazole,
2. 2'-phenyl-6-azido-11β-hydroxy-16α-methyl-17α,20;20,21-bismethylenedioxy-4,6-pregnadieno[3,2-c]pyrazole,
3. 2'-phenyl-6-azido-11β-hydroxy-16β-methyl-17α,20;20,21-bismethylenedioxy-4,6-pregnadieno[3,2-c]pyrazole,
4. 2'-phenyl-6-azido-11-keto-17α,20;20,21-bismethylenedioxy-4,6-pregnadieno[3,2-c]pyrazole,
5. 2'-phenyl-6-azido-11-keto-16α-methyl-17α,20;20,21-bismethylenedioxy-4,6-pregnadieno[3,2-c]pyrazole,
6. 2'-phenyl-6-azido-11-keto-16β-methyl-17α,20;20,21-bismethylenedioxy-4,6-pregnadieno[3,2-c]pyrazole,
7. 2'-phenyl-6-azido-11β-hydroxy-16-methylene-17α,20;20,21-bismethylenedioxy-4,6-pregnadieno[3,2-c]pyrazole,
8. 2'-phenyl-6-azido-11-keto-16-methylene-17α,20;20,21-bismethylenedioxy-4,6-pregnadieno[3,2-c]pyrazole,
9. 2'-phenyl-6-azido-9α,11β-dichloro-17α,20;20,21-bismethylenedioxy-4,6-pregnadieno[3,2-c]pyrazole.

C. In a manner similar to that described in Example 3C treat each of the 2'-phenyl-6-azido-17α,20;20,21-bismethylenedioxy-4,6-pregnadieno[3,2-c]pyrazoles prepared in above Example 7B with triphenylcarbenium tetrafluoroborate followed by aqueous bicarbonate or with 60% aqueous formic acid followed by aqueous potassium hydroxide to obtain, respectively, 1. 2'-phenyl-6-azido-11β,17α,21-trihydroxy-20-keto-4,6-pregnadieno[3,2-c]pyrazole,
2. 2'-phenyl-6-azido-11β,17α,21-trihydroxy-16α-methyl-20-keto-4,6-pregnadieno[3,2-c]pyrazole,
3. 2'-phenyl-6-azido-11β,17α,21-trihydroxy-16β-methyl-20-keto-4,6-pregnadieno[3,2-c]pyrazole,
4. 2'-phenyl-6-azido-11,20-diketo-17α,21-dihydroxy-4,6-pregnadieno[3,2-c]pyrazole,
5. 2'-phenyl-6-azido-11,20-diketo-16α-methyl-17α,21-dihydroxy-4,6-pregnadieno[3,2-c]pyrazole,
6. 2'-phenyl-6-azido-11,20-diketo-16β-methyl-17α,21-dihydroxy-4,6-pregnadieno[3,2-c]pyrazole,
7. 2'-phenyl-6-azido-11β,17α,21-trihydroxy-16-methylene-20-keto-4,6-pregnadieno[3,2-c]pyrazole,
8. 2'-phenyl-6-azido-11,20-diketo-16-methylene-17α,21-dihydroxy-4,6-pregnadieno[3,2-c]pyrazole,
9. 2'-phenyl-6-azido-9α,11β-dichloro-17α,21-dihydroxy-20-keto-4,6-pregnadieno[3,2-c]pyrazole.

D.
2'-Phenyl-6-Azido-17α,21-Dihydroxy-20-Keto-4,6-Pregnadieno[3,2-c]Pyrazole 21-Acetates Dissolve 1 gm. of each of the 6-azido-21-hydroxy-4,6-pregnadieno[3,2-c]pyrazoles prepared in Example 7C in 10 ml. of pyridine and 3 ml. of acetic anhydride. Allow each of the reaction solutions to stand at room temperature, pour into dilute hydrochloric acid, separate by filtration each of the resultant precipitates, wash with water and air dry to yield, respectively, 1. 2'-phenyl-6-azido-11β,17α,21-trihydroxy-20-keto-4,6-pregnadieno[3,2-c]pyrazole 21-acetate,
2. 2'-phenyl-6-azido-11β,17α,21-trihydroxy-16α-methyl-20-keto-4,6-pregnadieno[3,2-c]pyrazole 21-acetate,
3. 2'-phenyl-6-azido-11β,17α,21-trihydroxy-16β-methyl-20-keto-4,6-pregnadieno[3,2-c]pyrazole 21-acetate,
4. 2'-phenyl-6-azido-11,20-diketo-17α,21-dihydroxy-4,6-pregnadieno[3,2-c]pyrazole 21-acetate,
5. 2'-phenyl-6-azido-11,20-diketo-16α-methyl-17α,21-dihydroxy-4,6-pregnadieno[3,2-c]pyrazole 21-acetate,
6. 2'-phenyl-6-azido-11,20-diketo-16β-methyl-17α,21-dihydroxy-4,6-pregnadieno[3,2-c]pyrazole 21-acetate,
7. 2'-phenyl-6-azido-11β,17α,21-trihydroxy-16-methylene-20-keto-4,6-pregnadieno[3,2-c]pyrazole 21-acetate,
8. 2'-phenyl-6-azido-11,20-diketo-16-methylene-17α,21-dihydroxy-4,6-pregnadieno[3,2-c]pyrazole 21-acetate,
9. 2'-phenyl-6-azido-9α,11β-dichloro-17α,21-dihydroxy-20-keto-4,6-pregnadieno[3,2-c]pyrazole 21-acetate.

We claim:
1. A compound selected from the group consisting of a 6-azido-4,6-pregnadieno [3,2-c]pyrazole of the following formula:

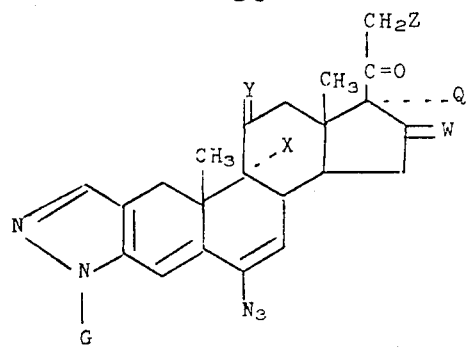

wherein G is a member selected from the group consisting of hydrogen, lower alkyl, cycloalkyl, aralkyl, aryl and lower hydrocarbon carboxylic acyl;

Q is a member selected from the group consisting of hydroxy, OR wherein R is an acyl radical of a hydrocarbon carboxylic acid having up to 12 carbon atoms, and hydrogen provided W is a member selected from the group consisting of hydrogen and (H, lower alkyl);

W is a member selected from the group consisting of

(H, lower alkyl), (H,α-hydroxy) and (H,α-OR₁), wherein R₁ is an acyl radical of a hydrocarbon carboxylic acid having up to 12 carbon atoms, =CHT wherein T is a member selected from the group consisting of hydrogen, lower alkyl, fluorine and chlorine and W and Q taken together is 16α,17α-lower alkylidenedioxy;

X is a member selected from the group consisting of hydrogen and halogen having an atomic weight less than 100;

Y is a member selected from the group consisting of

provided X is hydrogen, oxygen, (H,βOH), (H,βO-COH), and (H,β-halogen of atomic weight less than 100) providing X is halogen;

Z is a member selected from the group consisting of hydrogen, hydroxy, halogen having an atomic weight up to 40, OR₂ wherein R₂ is an acyl radical of an acid selected from the group consisting of a hydrocarbon carboxylic acid having up to 12 carbon atoms, phosphoric acid and the mono- and di-alkali and alkaline earth metal salts thereof, and Z together with Q is a member selected from the group consisting of alkylidenedioxy and alkyl orthoalkanoate.

2. A compound of claim 1 wherein G is a member selected from the group consisting of hydrogen, lower alkyl, phenyl, and phenyl substituted in the para position by a member selected from the group consisting of fluoro, trifluoromethyl, and nitro.

3. A compound of claim 1 wherein G is phenyl or p-fluorophenyl; W is (H,methyl); and Y is (H,βOH).

4. A compound of claim 1 wherein G is phenyl or p-fluorophenyl; W is (H,α-methyl); X is a halogen having an atomic weight less than 40; Y is (H,βOH), and Q and Z are each members selected from the group consisting of hydroxy or lower alkanoyloxy.

5. A compound of claim 1 wherein G is phenyl, W is (H,α-methyl), X is fluorine, Y is (H,βOH) and Q and Z are each members selected from the group consisting of hydroxy or lower alkanoyloxy.

6. A compound of claim 1 wherein G is phenyl, W is (H,α-methyl); X is fluorine; Y is (H,βOH); Q is hydroxy and Z is acetoxy, said compound being 2'-phenyl-6-azido-9α-fluoro-11β,17α,21-trihydroxy-16α-methyl-20-keto-4,6-pregnadieno[3,2-c]pyrazole 21-acetate.

7. A compound of claim 1 wherein G is phenyl, W is

X is hydrogen, Y is (H,βOH); Q is hydroxy and Z is acetoxy, said compound being 2'-phenyl-6-azido-11β,17α,21-trihydroxy-20-keto-4,6-pregnadieno [3,2-c]pyrazole 21-acetate.

8. A compound of claim 1 wherein G is phenyl; W is (H,α-methyl); Q is hydroxy; X is hydrogen; Y is (H,βOH), and Z is acetoxy, said compound being 2'-phenyl-6-azido-11β,17α,21-trihydroxy-16α-methyl-20-keto-4,6-pregnadieno-[3,2-c]pyrazole 21-acetate.

9. The process for the preparation of 6-azido-4,6-pregnadieno [3,2-c]pyrazoles of the following formula I:

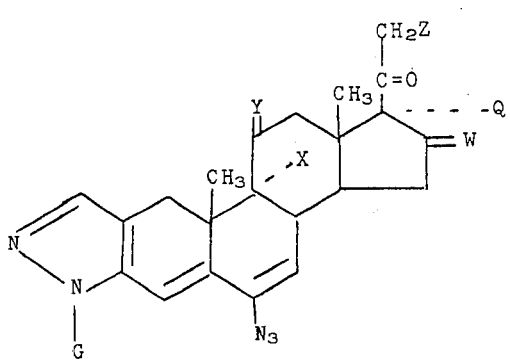

wherein G is a member selected from the group consisting of hydrogen, lower alkyl, cycloalkyl, aralkyl, aryl, and lower hydrocarbon carboxylic acid;

Q is a member selected from the group consisting of hydroxy, OR wherein R is an acyl radical or a hydrocarboncarboxylic acid having up to 12 carbon atoms, and hydrogen provided W is a member selected from the group consisting of hydrogen and (H,lower alkyl);

W is a member selected from the group consisting of

(H,lower alkyl), (H,α-hydroxy), (H,α-OR₁) wherein R₁ is an acyl radical of a hydrocarbon carboxylic acid having up to 12 carbon atoms, =CHT wherein T is a member selected from the group consisting of hydrogen, lower alkyl, fluorine and chlorine and W and Q taken together is 16α,17α-lower alkylidenedioxy;

X is a member selected from the group consisting of hydrogen and halogen having an atomic weight less than 100;

Y is a member selected from the group consisting of hydrogen provided X is hydrogen, oxygen, (H,βOH), and (H,β-halogen of atomic weight less than 100) providing X is halogen;

Z is a member selected from the group consisting of hydrogen, hydroxy, halogen having an atomic weight up to 40, OR₂ wherein R₂ is an acyl radical of an acid selected from the group consisting of a hydrocarbon carboxylic acid having up to 12 carbon atoms, and Z taken together with Q is alkylidenedioxy; and when Z and Q are hydroxy and W is other than (HαOH), the 17α,20;20,21-bisalkylidenedioxy derivatives thereof, which comprises treating a 6-azido-7-halogeno-4-pregneno-[3,2-c]pyrazole of following formula II:

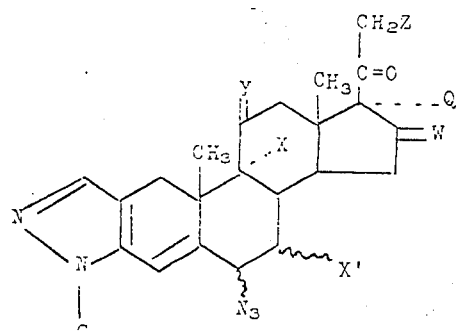

wherein G, Q, W, X, Y and Z are as hereinabove defined, and X₁ is a halogen of atomic weight greater than 20, with a dehydrohalogenating agent in an aprotic solvent.

10. The process of claim 9 wherein said dehydrohalogenating agent is a tetraalkylammonium halide.

11. The process of claim 9 wherein said dehydrohalogenating agent in an aprotic solvent is tetramethylammonium fluoride in acetonitrile.

12. The process of claim 9 wherein said 6-azido-7-halogeno-4-pregneno[3,2-c]pyrazole is a compound of formula II wherein X is halogen.

13. The process of claim 9 wherein said 6-azido-7-halogeno-4-pregneno[3,2-c]pyrazole is a compound of formula II wherein X is halogen, X' is bromine, and said dehydrohalogenating agent in an aprotic solvent is tetramethylammonium fluoride in acetonitrile.

14. The process of claim 9 wherein said 6-azido-7-halogeno-4-pregneno[3,2-c]pyrazole is a compound of formula II wherein X is fluorine, X' is bromine, Y is (H,βOH), W is (H,methyl), Z is lower alkanoyl, and said dehydrohalogenating agent is an aprotic solvent is tetramethylammonium fluoride in acetonitrile.

15. The process of claim 9 wherein said 6-azido-7-halogeno-4-pregneno[3,2-c]pyrazole of formula II is prepared by treating a 6-unsubstituted-4,6-pregnadieno[3,2-c]pyrazole of following formula III:

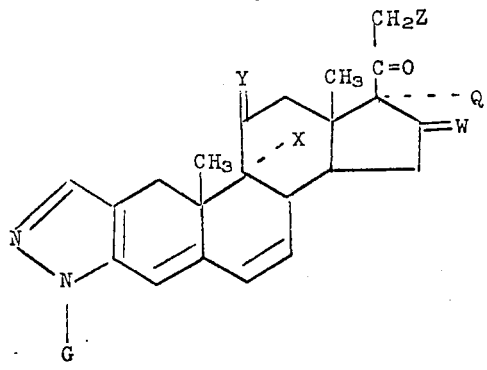

III wherein G, Q, W, X, Y and Z are as defined for formula I, claim 9, with a halogen azide, wherein said halogen has an atomic weight greater than 20.

16. The process of claim 15 wherein said halogen azide is bromine azide whereby is obtained a 6-azido-7-bromo derivative of formula II.

17. A 6-azido-7-halogeno-4-pregneno[3,2-c]pyrazole of the following formula:

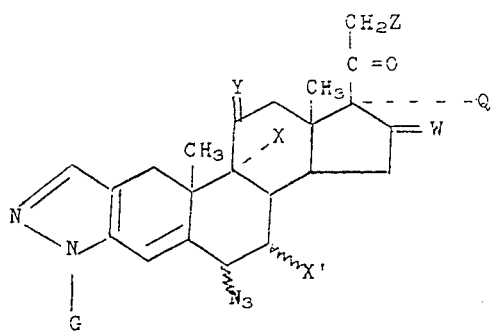

wherein X' is a halogen of atomic weight greater than 20;

wherein G is a member selected from the group consisting of hydrogen, lower alkyl, cycloalkyl, aralkyl, aryl, and lower hydrocarbon carboxylic acyl;

Q is a member selected from the group consisting of hydroxy, OR wherein R is an acyl radical of a hydrocarboncarboxylic acid having up to 12 carbon atoms, and hydrogen provided W is a member selected from the group consisting of hydrogen and (H,lower alkyl);

W is a member selected from the group consisting of hydrogen, (H,lower alkyl), (H,α-hydroxy) and (H,α-$OR_1$), wherein $R_1$ is an acyl radical of a hydrocarbon carboxylic acid having up to 12 carbon atoms, =CHT wherein T is a member selected from the group consisting of hydrogen, lower alkyl, fluorine and chlorine and W and Q together is 16α,17α-lower alkylidenedioxy;

X is a member selected from the group consisting of hydrogen and halogen having an atomic weight less than 100;

Y is a member selected from the group consisting of hydrogen provided X is hydrogen, oxygen, (H,βOH), and (H,β-halogen of atomic weight less than 100) providing X is halogen;

Z is a member selected from the group consisting of hydrogen, hydroxy, halogen having an atomic weight up to 40, $OR_2$ wherein $R_2$ is an acyl radical of an acid selected from the group consisting of a hydrocarbon carboxylic acid having up to 12 carbon atoms, and Z together with Q is alkylidenedioxy, and when Q and Z are hydroxy and W is other than (H,αOH), the (17α, 20;20,21)-bisalkylidenedioxy derivatives thereof.

18. A compound of claim 17 wherein X' is bromine and X is a halogen of atomic weight less than 100.

19. A compound of claim 17 wherein G is phenyl, Q is hydroxyl, W is (H,α-methyl), X is fluorine, X' is bromine, Y is (H,βOH), and Z is acetoxy, said compound being 2'-phenyl-6-azido-7-bromo-9α-fluoro-11β, 17α,21-trihydroxy-16α-methyl-20-keto-4,6-pregnadieno [3,2-c]pyrazole 21acetate.

20. A compound of claim 17 wherein G is phenyl, Q is hydroxyl, Y is (H,βOH), W and X are hydrogen, X' is bromine, Z is acetoxy, said compound being 2'-phenyl-6-azido-7-bromo-11β,17α,21-trihydroxy-20-keto-4,6-pregnadieno[3,2-c]pyrazole 21-acetate.

21. The process for the preparation of a 6-azido-4,6-pregnadieno[3,2-c]pyrazole of the following formula I:

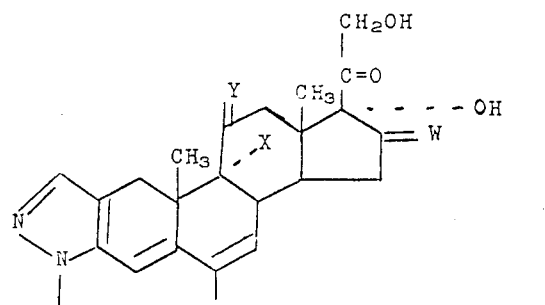

I wherein G is a member selected from the group consisting of hydrogen, lower alkyl, cycloalkyl, aralkyl, aryl, and lower hydrocarbon carboxylic acyl;

W is a member selected from the group consisting of

(H,lower alkyl), (H,α-$OR_1$) wherein $R_1$ is an acyl radical of a hydrocarbon carboxylic acid having up to 12 carbon atoms, =CHT wherein T is a member selected from the group consisting of hydrogen, lower alkyl, fluorine and chlorine;

X is a member selected from the group consisting of hydrogen and halogen having an atomic weight less than 100;

Y is a member selected from the group consisting of

provided X is hydrogen, oxygen, (H,βOH), and (H,β-halogen of atomic weight less than 100) providing X is halogen;

which comprises treating a 3-keto-6-azido-4,6-pregnadiene of the following formula II:

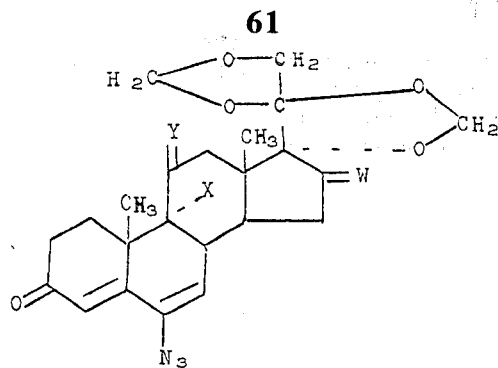

wherein W, X and Y are as hereinabove defined; with an alkyl formate in the presence of a strong base under an inert atmosphere, followed by treatment of the thereby formed 2-hydroxymethylene derivative of formula II either with a hydrazine derivative of formula III:

GNHNH$_2$                      (III)

wherein G is as hereinabove defined, whereby is formed a 17α, 20;20,21-bismethylenedioxy derivative of formula I; or with a lower alkanol in the presence of acid followed by treatment of the resulting 2-alkoxymethylene derivative of formula II with a hydrazine of formula III wherein G is as hereinabove defined, whereby is formed a 17α,20;20,21-bismethylenedioxy derivative of formula I; and treating the thereby formed 17α,20;20,21-bismethylenedioxy derivative of a compound of formula I with acid.

22. The process of claim 21 including the step of isolating the compound of formula I thereby formed.

23. The process of claim 9 including the step of isolating the compound of formula I thereby formed.

24. A 6-azido-17α,20;20,21-bismethylenedioxy-4,6-pregnadieno[3,2-c]pyrazole of the following formula:

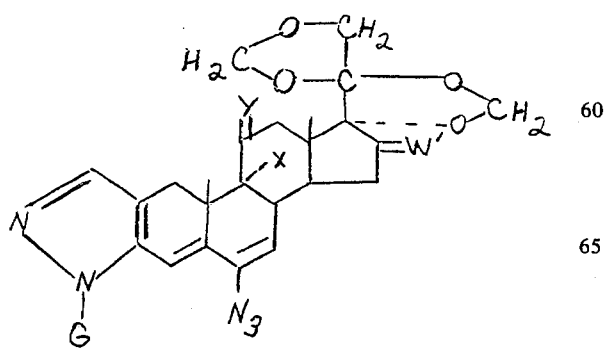

wherein G is a member selected from the group consisting of hydrogen, lower alkyl, cycloalkyl, aralkyl, aryl and lower hydrocarbon carboxylic acyl;

X is a member selected from the group consisting of hydrogen and halogen having an atomic weight less than 100;

Y is a member selected from the group consisting of

provided X is hydrogen, oxygen, (H,βOH), and (H,β-halogen of atomic weight less than 100) providing X is halogen; and W' is a member selected from the group consisting of

(H,lower alkyl), =CHT wherein T is a member selected from the group consisting of hydrogen, lower alkyl, fluorine and chlorine.

25. A 6-azido-21-substituted-4,6-pregnadieno[3,2-c]pyrazole of the following formula:

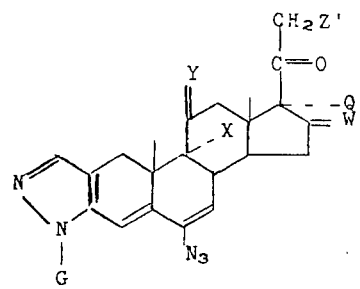

wherein G is a member selected from the group consisting of hydrogen, lower alkyl, cycloalkyl, aralkyl, aryl and lower hydrocarbon carboxylic acyl;

Q is a member selected from the group consisting of hydroxy, OR wherein R is an acyl radical of a hydrocarbon carboxylic acid having up to 12 carbon atoms, and hydrogen provided W is a member selected from the group consisting of hydrogen and (H, lower alkyl);

W is a member selected from the group consisting of

(H, lower alkyl), (H, α-hydroxy) and (H,α-OR$_1$), wherein R$_1$ is an acyl radical of a hydrocarbon carboxylic acid having up to 12 carbon atoms, =CHT wherein T is a member selected from the group consisting of hydrogen, lower alkyl, fluorine and chlorine and W and Q taken together is 16α,17α-lower alkylidenedioxy;

X is a member selected from the group consisting of hydrogen and halogen having an atomic weight less than 100;

Y is a member selected from the group consisting of

provided X is hydrogen, oxygen, (H,βOH), and (H,β-halogen of atomic weight less than 100) providing X is halogen; and Z' is a member selected from the group consisting of iodine, bromine and hydrocarbonsulfonyloxy having up to 7 carbon atoms.

26. A 2-hydroxymethylene-6-azido-17α,20;20,21-bismethylenedioxy-4,6-pregnadien-3-one of the following formula:

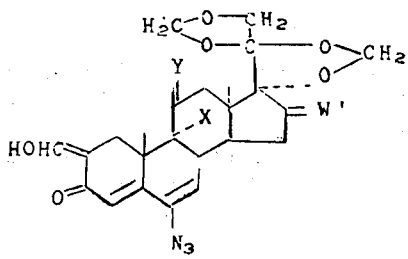

wherein X is a member selected from the group consisting of hydrogen and halogen having an atomic weight less than 100;

Y is a member selected from the group consisting of

provided X is hydrogen, oxygen, (H,βOH), and (H,β-halogen of atomic weight less than 100) providing X is halogen; and W' is a member selected from the group

(H, lower alkyl), =CHT wherein T is a member selected from the group consisting of hydrogen, lower alkyl, fluorine and chlorine.

* * * * *

UNITED STATES PATENT OFFICE
CERTIFICATE OF CORRECTION

Patent No. 3,932,388　　　　　　　　　Dated January 13, 1976

Inventor(s) Thomas L. Popper et al　　　　Page 1 of 3

It is certified that error appears in the above-identified patent and that said Letters Patent are hereby corrected as shown below:

In the title, "-AZIDO-4,6-" should read ---6-AZIDO-4,6---. Column 1, line 1, the title, "-AZIDO-4,6-PREGNADIENO-" should read ---6-AZIDO-4,6-PREGNADIENO---. Column 4, line 13, "in about Formula I" should read ---in above Formula I---; line 34, "4,6-pregadieno-" should read ---4,6-pregnadieno---. Column 7, lines 37 and 38, "-$[$3,2-c$]$/pyrazole-" should read ---$[$3,2-c$]$/pyrazole---.

Column 12, line 23, "-11$^\alpha$,21-trihy-" should read ---11$^\beta$,17$^\alpha$,21-trihy---; line 27, "2'-phenyl-67-azido-" should read ---2'-phenyl-6-azido---. Column 13, line 23, "actone," should read ---acetone,---. Column 15, line 6, "intermediates or" should read ---intermediates of---; line 41, "(e.g. 2G2-phenyl-6-azido-7-bromo-9G2a-" should read ---(e.g. 2'-phenyl-6-azido-7-bromo-9$^\alpha$---. Column 16, lines 2 and 3, "(e.g. 2G2-phenyl-6-azido-7-bromo-9G2a-2-fluoro-11$^\beta$,17$^\alpha$,21-trihydroxy-16G2a-methyl-" should read ---(2'-phenyl-6-azido-7-bromo-9$^\alpha$-fluoro-11$^\beta$,17$^\alpha$,21-trihydroxy-16$^\alpha$-methyl---; lines 16 and 17, "(e.g. 2G2-phenyl-6-azido-9G2a-fluoro-11$^\beta$,17$^\alpha$,21-trihydroxy-16G2a-methyl-" should read ---(e.g. 2'-phenyl-6-azido-9$^\alpha$-fluoro-11$^\beta$,17$^\alpha$,21-trihydroxy-16$^\alpha$-methyl---; lines 24 and 25, "(e.g. 2G2-phenyl-6-azido-9G2a-fluoro-11$^\beta$,17$^\alpha$,21-trihydroxy-16G2a-methyl-" should read ---(e.g. 2'-phenyl-6-azido-9$^\alpha$-fluoro-11$^\beta$,17$^\alpha$,21-trihydroxy-16$^\alpha$-methyl---. Column 17, line 6, "a 17G2a-acetoxy-" should read ---a 17$^\alpha$-acetoxy---; line 14, "at c-11 by" should read ---at C-11 by---; line 16, "halogenoalkylidene, halogen," should read ---halogenoalkylidene, hydroxy,---; line 18, "or 17G2a-substituted-" should read ---or 17$^\alpha$-substituted-"; lines 26 and 27, "a 9G2a-halogeno-11G2s-hydroxyl function since the desired 6-azido-9G2a-halogeno-11G2s-hydroxy-" should read ---a 9$^\alpha$-halogeno-11$^\beta$-hydroxyl function since the desired 6-azido-9$^\alpha$-halogeno-11$^\beta$-hydroxy---; lines 39-41, "corresponding 6$^\alpha$,7G2a-oxido derivative, thence to a 6G2s-azido-7G2a-acyloxy derivative" should read ---corresponding 6$^\alpha$,7$^\alpha$-oxido derivative, thence to a 6$^\beta$-azido-7$^\alpha$-acyloxy derivative---.

UNITED STATES PATENT OFFICE
CERTIFICATE OF CORRECTION

Patent No. 3,932,388　　　　　　　　　Dated January 13, 1976

Inventor(s) Thomas L. Popper et al　　　Page 2 of 3

It is certified that error appears in the above-identified patent and that said Letters Patent are hereby corrected as shown below:

Column 18, lines 2 and 3, "-9G2a-fluoro-16G2a-methyl-$17^{\alpha},20;20,21$-bismethylenedioxy-4,6-pregnadiene-11G2s-" should read ---$9^{\alpha}$-fluoro-$16^{\alpha}$-methyl-$17^{\alpha},20;20,21$-bismethylenedioxy-4,6-pregnadiene-$11^{\beta}$---; lines 9 and 10, "a 2G2-phenylpyrazole derivative, namely 2G2-phenyl-9G2a-fluoro-11G2s-hydroxy-16G2a-" should read ---a 2'-phenylpyrazole derivative, namely 2'-phenyl-$9^{\alpha}$-fluoro-$11^{\beta}$-hydroxy-$16^{\alpha}$---; line 15, "namely 2G2-phenyl-9G2a-fluoro-" should read ---namely 2'-phenyl-$9^{\alpha}$-fluoro---; line 27, "a 2G2-substituted-" should read ---a 2'-substituted---; line 35, "a 2G2-substituted-" should read ---a 2'-substituted---; line 50, "-2G2-substituted-" should read ---2'-substituted---; lines 52-55, "-2G2-alkyls such as 2G2-methyl-, 2G2-ethyl-, 2G2-butyl-, 2G2-propyl-, 2G2($\beta$-hydroxyethyl)-; 2G2-cycloalkyl-; 2G2-aryl-" should read ---2'-alkyls such as 2'-methyl-, 2'-ethyl-, 2'-butyl-, 2'-propyl-, 2'-($\beta$-hydroxyethyl)-; 2'-cycloalkyl-; 2'-aryl---; line 56, "-2G2-phenyl- and the 2G2-" should read ---2'-phenyl- and the 2'---; lines 58-63, "-2G2-(1G2-naphthyl)-, 2G2-(2G2-pyridyl)-, 2G2-(3G2-pyridyl)-, 2G2-(4G2-pyridyl)-, 2G2-(4G2-pyridyloxide)-, 2G2-(2G2-pyrimidyl)-; 2G2-aralkyl-, such as 2G2-benzyl- and 2G2-phenylethenyl-" should read ---2'-(1"-naphthyl)-, 2'-(2"-pyridyl)-, 2'-(3"-pyridyl)-, 2'-(4"-pyridyl)-, 2'-(4"-pyridyloxide)-, 2'-(2"-pyrimidyl)-; 2'-aralkyl-, such as 2'-benzyl- and 2'-phenylethenyl---; lines 67 and 68, "-2G2-phenyl-6-azido-4,6-pregnadieno-$\underline{/}3,2$-c$\underline{\phantom{/}}$/-pyrazoles and 2G2-" should read ---2'-phenyl-6-azido-4,6-pregnadieno-$\underline{/}3,2$-c$\underline{\phantom{/}}$/-pyrazoles and 2'---. Column 19, line 3, "the 2G2-alkyl-" should read ---the 2'-alkyl---; line 11, "and an 11G2s-" should read ---and an $11^{\beta}$---; line 12, "a 9G2a-halogeno-" should read ---a $9^{\alpha}$-halogeno---; line 17, "-azido-9G2a-" should read ---azido-$9^{\alpha}$---; line 23, "-azido-9G2a-" should read ---azido-$9^{\alpha}$---; line 28, "-11G2a-hydroxyl-" should read ---$11^{\beta}$-hydroxyl---; line 30, "an 11G2s-hydroxyl-" should read ---an $11^{\beta}$-hydroxyl---; line 31, "-11G2a-hydroxy-" should read ---$11^{\beta}$-hydroxy---; lines 32 and 33, "-2G2-phenyl-6-azido-9G2a-fluoro-

UNITED STATES PATENT OFFICE
CERTIFICATE OF CORRECTION

Patent No. 3,932,388  Dated January 13, 1976

Inventor(s) Thomas L. Popper et al   Page 3 of 3

It is certified that error appears in the above-identified patent and that said Letters Patent are hereby corrected as shown below:

11β,17α,21-trihydroxy-16G2a-" should read ---2'-phenyl-6-azido-9α-fluoro-11β,17α,21-trihydroxy-16α---; lines 37-39, "-9G2a-fluoro-16G2a-methyl-17α,20;20,21-bismethylenedioxy-4,6-pregnadiene-11G2s-" should read ---9α-fluoro-16α-methyl-17α,20;20,21-bis-methylenedioxy-4,6-pregnadiene-11β---; lines 42 and 43, "-2G2-phenyl-6-azido-9G2a-fluoro-11G2s-hydroxy-16G2a-" should read ---2'-phenyl-6-azido-9α-fluoro-11β-hydroxy-16α---; line 47, "a 9G2a-" should read ----a 9α---; lines 49 and 50, "-2G2-phenyl-6-azido-9G2a-fluoro-11β,17α,21-trihydroxy-16G2a-" should read ---2'-phenyl-6-azido-9α-fluoro-11β,17α,21-trihydroxy-16α---; line 52, "The 2G2-" should read ---The 2'---; line 68, "-[3,23,2]-" should read ---[3,2-c]---. Column 20, line 5, "the 2G2-" should read ---the 2'---; line 15, "21-acrylate-" should read ---21-acylate---; line 23, "a 2G2-acyl-" should read ---a 2'-acyl---; line 28, "the 2G2-" should read ---the 2'---; line 56, "-2G2-acyl-" should read ---2'-acyl---; line 62, "-17G2a-hydroxy-" should read ---17α-hydroxy---. Column 21, lines 44 and 45, "-2G2-phenyl-6-azido-9G2a-fluoro-11β,17α,21-trihydroxy-16G2a-" should read ---2'-phenyl-6-azido-9α-fluoro-11β,17α,21-trihydroxy-16α---. Column 22, line 6, "or 17G2a-" should read ---or 17α---; lines 23 and 24, "a 17G2a-hydroxyl group, any 11G2s-" should read ---a 17α-hydroxyl group, any 11β---; line 25, "the 11G2s-" should read ---the 11β---; line 31, "-17G2a-" should read ---17α---; line 39, "The 17G2a-" should read ---The 17α---. Column 33, line 34, Title, "B. 6β,6β-Dimethanesulfonyloxy-" should read ---B. 6β,7β-Dimethanesulfonyloxy---. Column 35, line 17, "-4,6-pregnadiono-" should read ---4,6-pregnadieno---.

Signed and Sealed this

Fifteenth Day of March 1977

[SEAL]

Attest:

RUTH C. MASON
Attesting Officer

C. MARSHALL DANN
Commissioner of Patents and Trademarks